US007078184B2

(12) United States Patent
Curtis

(10) Patent No.: US 7,078,184 B2
(45) Date of Patent: Jul. 18, 2006

(54) 52906 POTASSIUM CHANNEL NUCLEIC ACIDS AND USES THEREFOR

(75) Inventor: Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 495 days.

(21) Appl. No.: 09/875,321

(22) Filed: Jun. 6, 2001

(65) Prior Publication Data

US 2003/0049724 A1 Mar. 13, 2003

Related U.S. Application Data

(60) Provisional application No. 60/209,845, filed on Jun. 6, 2000.

(51) Int. Cl.
*C12N 15/12* (2006.01)
*C12N 15/62* (2006.01)
*C12N 5/10* (2006.01)

(52) U.S. Cl. .................. 435/69.1; 435/320.1; 435/325; 536/23.5

(58) Field of Classification Search ................ 435/69.1, 435/320.1, 325; 536/23.5
See application file for complete search history.

(56) References Cited

FOREIGN PATENT DOCUMENTS

| WO | WO 98/11139 A1 | 3/1998 |
|---|---|---|
| WO | WO 98/11139 | 3/1998 |
| WO | WO 99/03882 | 1/1999 |
| WO | WO 99/47923 | 9/1999 |
| WO | WO 00/12711 A2 | 3/2000 |
| WO | WO 00/12711 | 3/2000 |
| WO | WO 01/04133 | 1/2001 |
| WO | WO 01/29068 | 4/2001 |
| WO | WO 01/75067 A2 | 10/2001 |

OTHER PUBLICATIONS

Desai, R., et al., "Ca2+–Activated K+ Channels in Human Leukemic Jurkat T Cells", J. Biol. Chem. 275(51):39954–39963 (2000).
Xia, X. M., et al., "Mechanism of Calcium Gating in Small–Conductance Calcium–Activated Potassium Channels", Nature (395):503–507 (1998).
Desai, R., et al., "*Homo Sapiens* Apamin–Sensitive Small–Conductance Ca2+–Activated Potassium Channel (KCNN2) mRNA, complete cds." Dec. 18, 2000 (sequence) GenBank [online] Bethesda, MD, USA : National Center for Biotechnology Information [retrieved on Aug. 17, 2002]. Retrieved from the Internet: URL: http://www.ncbi.nlm.gov/>. GenBank Accession No. AF239613.

Kohler, M., et al., "Small–conductance, Calcium–Activated Potassium Channels from Mammalian Brain", Science 273 (5282):1709 [retrieved on Oct. 28, 2003]. Retrieved from the Internet: URL: http://www.sciencemag.org/>.
Strausberg, Robert, Ph.D., Nov. 17, 1998 (sequence) GenBank [online] Bethesda, MD, USA: National Center for Biotechnology Information [retrieved on Oct. 28, 2003]. Retrieved from the Internet: URL: http://www.ncbi.nlm.nih.gov/>, GenBank Accession No. AI271784.
Jager, H., et al., "SK2 Encodes the Apamin–Sensitive Ca2+–Activated K+ Channels in the Human Leukemic T Cell Line, Jurkat", FEBS Letter 469 :196–202 (2000).
Blast 1.4 Nucleotide Alignment of SEQ ID No.:7463 disclosed in WO 01/75067 (cited as B3) with SEQ ID No.:1 of present application, do not publish.
Blast 1.4 Nucleotide Alignment of SEQ ID No.:15580 disclosed in WO 01/75067 (cited as B3) with SEQ ID No.:1 of present application, do not publish.
Atscuhl et al., *J. Mol. Biol.*, 1990, 215:403–410.
Atschul et al., *Nucleic Acids Res.*, 1997, 25(17):3389–3402.
International Human Genome Sequencing Consortium, *Initial sequencing and analysis of the human genome*, Nature 1, vol. 409, Feb. 15, 2001.
Chanda (ed.), *Current Protocols in Molecular Biology*, 2000, vol. 4, John Wiley & Sons, Inc. (Table of Contents only).
Desai et al., *The Journal of Biological Chemistry*, vol. 275, No. 51, (2000) pp. 39954–39963.
Jäger et al., *FEBS Letters*, 469 (2000) 196–202.
Karlin et al., *Proc. Natl. Acad. Sci. USA*, 1990, 87(6):2264–2268.
Karlin et al., *Proc. Natl. Acad. Sci. USA*, 1993, 90(12):5873–5877.
*Molecular Cloning–A Laboratory Manual*, 1989, $2^{nd}$ Edition, Sambrook et al. (eds.), Cold Spring Harbor Laboratory Press (Table of Contents only).
Myers et al., *CABIOS*, 1988, 4:11–17.
The Human Genome *The Sequencing of the Human Genome*, Science, vol. 291, Feb. 16, 2001.
Sonnhammer et al., *Proteins*, 1997, 28(3):405–420.
Weintraub et al., *Trends in Genetics*, Jan. 1985.

(Continued)

*Primary Examiner*—Michael Pak
(74) *Attorney, Agent, or Firm*—Millennium Pharmaceuticals, Inc.

(57) ABSTRACT

The invention provides isolated nucleic acids molecules, designated 52906, 33408, or 12189 nucleic acid molecules, which encode novel potassium channel members. The invention also provides antisense nucleic acid molecules, recombinant expression vectors containing 52906, 33408, or 12189 nucleic acid molecules, host cells into which the expression vectors have been introduced, and nonhuman transgenic animals in which a 52906, 33408, or 12189 gene has been introduced or disrupted. The invention still further provides isolated 52906, 33408, or 12189 proteins, fusion proteins, antigenic peptides and anti-52906, 33408, or 12189 antibodies. Diagnostic methods utilizing compositions of the invention are also provided.

30 Claims, 9 Drawing Sheets

OTHER PUBLICATIONS

GenBank Accession No. AF032099 (Mar. 21, 2000).
GenBank Accession No. AF032101 (Apr. 6, 1995).
GenBank Accession No. 3004907 (Apr. 2, 1998).
GenBank Accession No. U69185 (Oct. 27, 1999).
GenBank Accession No. AW628656 (Mar. 31, 2000).
GenBank Accession No. F05455 (Feb . 15, 1995).
GenBank Accession No. F05456 (Feb. 19, 1995).
GenBank Accession No. Z38438 (Oct. 27, 1994).
GenBank Accession No. 6625694 (Dec. 22, 1999).
GenBank Accession No. AL355101 (Sep. 17,2001).
GenBank Accession No. AL560989 (Oct. 31, 1994).
GenBank Accession No. AI810558 (Sep. 7, 1999).
GenBank Accession No. AA418096 (Feb. 5, 1999).
GenBank Accession No. U69882 (May 30, 1997).
GenBank Accession No. AF079372 (Jun. 18, 1993).
GenBank Accession No. V35457 (Oct. 1, 1998).
GenBank Accession No. V35446 (Oct. 1, 1998).
GenBank Accession No. Z51630 (Jun. 21, 2000).
GenBank Accession No. 1575663 (Oct. 2, 1996).
GenBank Accession No. 6650274 (Jan. 1, 2000).
GenBank Accession No. W63707 (Oct. 1, 1998).
GenBank Accession No. W63702 (Oct. 1, 1998).
GenBank Accession No. AI271784 (Nov. 19, 1998).

```
ion_trans: domain 1 of 1, from 472 to 661: score 0.1, E = 1.2
   (SEQ ID NO:9)   *->ilfildllfvllflleivlkfiayglkstsniaakylksifnildll
                     ++ i  +   ++f++ ++l    ++++        ++ y +++         +
     52906     472   DWRIAMTYERIFFICLEILVCAIHPI------PGNYTFTWTA-RLAF 511 ailpllllllvlflsgteqvakkrlrerfslelsqwyyrilrflrlLrllR
                     ++ p+   +    +   +                     l++  +Lrl+
     52906     512  SYAPS--TTTADVDII---------------------LSIPMFLRLYL 536 lLrllrllrrletlf.e.....fe.lgtlaWslqslgralksilrfllll
                     + r++ ++ +lf+ +++++++ l ++            +k+++ ++  +
     52906     537  ---IARVMLLHSKLFtDtssrsIGaLNKI---NFNTRFVMKTLMTICPGT 580 llllligfsvigyllfkgyedlsenevdgnsefssyfdafyflfvtlttvG
                    +ll++  s+ ++++  +  + +e+   d+ +  s++  a++   +t++++G
     52906     581  VLLVF--SISLWIIAAWTVRACERYHDQQDVTSNFLGAMWLISITFLSIG 628 fGdlvpvwlgiiffvlffiivgllllnlliavi<-*
                    +Gd+vp++++   ++l+  i+g   ++l +av+
     52906     629  YGDMVPNTYCGKGVCLLTGIMGAGCTALVVAVV         661
```

Figure 2

```
ion_trans: domain 1 of 1, from 247 to 467: score 94.8, E = 1.7e-24
   (SEQ ID NO:9) *->ilfildllfvllflleivlkfiayglkstsn............iaak
                    +1   ld + +++fl++ivl+f+  +   + +++++  ++++ i++
       33408  247   WLV-LDSVVDVIFLVDIVLNFH-TT----FVgpggevisdpklIRMN 287 ylksifnildllailpllllllvlflsgteqvakkrlrerfslelsqwyyr
                    ylk++f  +dll++lp++++ ++   +++                    +
       33408  288   YLKTWFV-IDLLSCLPYDIINAFENVDE--------------------G 315 ilrflrlLrllRlLrllrllrrletlfefelgtlaWslqslg.ralksil
                    i +++++L+ +R   llrl r+ ++    1 +   1   +++   ++
       33408  316   ISSLFSSLKVVR---LLRLGRVARK-----LDHY---LEYGAaVLVLLVC 354 rflllllllligfsvigyllfkgyedlse..................
                    f+l++++l ++++ ig + + ++ +     +++    + +++   ++
       33408  355   VFGLVAHWLACIWYSIGDYEVIDEVTNTIqidswlyqlalsigtpyrynt 404

...nevdgnsefssyfdafyflfvtlttvGfGdlvpv.wlgiiffvlffi
                    + + +++g+s+  s y  ++yf++++ltt+GfG++ p++  +++f v++++
       33408  405   sagIWEGGPSKDSLYVSSLYFTMTSLTTIGFGNIAPTtDVEKMFSVAMMM 454 ivgllllnlliavi<-*
                    +++ ll +++++++
       33408  455   VGS-LLYATIFGNV    467
```

Figure 4A

```
cNMP_binding: domain 1 of 1, from 565 to 655: score 78.3, E = 1.5e-19
   (SEQ ID NO:10) *->aleersypaGeviirqGdpgdsfYivlsGevevykltedGartpevs
                     ++ + ++G+ i++ G+  d + +v+sG++ev++
       33408  565    EFQTIHCAPGDLIYHAGESVDALCFVVSGSLEVIQ----------- 599 qkqdtreqvvatlgpGdfFGElalltndgnknavlpsldqgaprtatvrA
                     +++vva+lg+Gd+FG++ +         + +a+   a+vrA
       33408  600    -----DDEVVAILGKGDVFGDIFW-KE----------TTLAHACANVRA 632 ltdsellrldredFrrllqkype<-*
                     lt+++l+ + re+++ +l+ y +
       33408  633    LTYCDLHIIKREALLKVLDFYTA    655
```

Figure 4B

```
33408           MPGGKRGLVA  PQNTFLENIV  RRSSESSFLL  GNAQIVDWPV  VYSNDGFCKL
rat EAG2        MPGGKRGLVA  PQNTFLENIV  RRSSESSFLL  GNAQIVDWPV  VYSNDGFCKL
(SEQ ID NO:12)

SGYHRADVMQ  KSSTCSFMYG  ELTDKKTIEK  VRQTFDNYES  NCFEVLLYKK
                SGYHRADVMQ  KSSTCSFMYG  ELTDKKTIEK  VRQTFDNYES  NCFEVLLYKK

NRTPVWFYMQ  IAPIRNEHEK  VVLFLCTFKD  ITLFKQPIED  DSTKGWTKFA
                NRTPVWFYMQ  IAPIRNEHEK  VVLFLCTFKD  ITLFKQPIED  DSTKGWTKFA

RLTRALTNSR  SVLQQLTPMN  KTEVVHKHSR  LAEVLQLGSD  ILPQYKQEAP
                RLTRALTNSR  SVLQQLTPMN  KTETVHKHSR  LAEVLQLGSD  ILPQYKQEAP

KTPPHIILHY  CAFKTTWDWV  ILILTFYTAI  MVPYNVSFKT  KQNNIAWLVL
                KTPPHIILHY  CAFKTTWDWV  ILILTFYTAI  MVPYNVSFKT  KQNNIAWLVL

DSVVDVIFLV  DIVLNFHTTF  VGPGGEVISD  PKLIRMNYLK  TWFVIDLLSC
                DSVVDVIFLV  DIVLNFHTTF  VGPGGEVISD  PKLIRMNYLK  TWFVIDLLSC

LPYDIINAFE  NVDEGISSLF  SSLKVVRLLR  LGRVARKLDH  YLEYGAAVLV
                LPYDIINAFE  NVDEGISSLF  SSLKVVRLLR  LGRVARKLDH  YLEYGAAVLV

LLVCVFGLVA  HWLACIWYSI  GDYEVIDEVT  NTIQIDSWLY  QLALSIGTPY
                LLVCVFGLVA  HWLACIWYSI  GDYEVIDEVT  NTIQIDSWLY  QLALSIRTPY

RYNTSAGIWE  GGPSKDSLYV  SSLYFTMTSL  TTIGFGNIAP  TTDVEKMFSV
                RYNTSAGIWE  GGPSKDSLYV  SSLYFTMTSL  TTIGFGNIAP  TTDVEKMFSV

AMMMVGSLLY  ATIFGNVTTI  FQQMYANTNR  YHEMLNNVRD  FLKLYQVPKG
                AMMMVGSLLY  ATIFGNVTTI  FQQMYANTNR  YHEMLNNVRD  FLKLYQVPKG

LSERVMDYIV  STWSMSKGID  TEKVLSICPK  DMRADICVHL  NRKVFNEHPA
                LSERVMDYIV  STWSMSKGID  TEKVLSICPK  DMRADICVHL  NRKVFNEHPA

FRLASDGCLR  ALAVEFQTIH  CAPGDLIYHA  GESVDALCFV  VSGSLEVIQD
                FRLASDGCLR  ALAVEFQTIH  CAPGDLIYHA  GESVDALCFV  VSGSLEVIQD

DEVVAILGKG  DVFGDIFWKE  TTLAHACANV  RALTYCDLHI  IKREALLKVL
                EEVVAILGKG  DVFGDIFWKE  TTLAHACANV  RALTYCDLHI  IKREALLKVL
```

Figure 4C

```
DFYTAFANSF  SRNLTLTCNL  RKRIIFRKIS  DVKKEEEERL  RQKNEVTLSI
DFYTAFANSF  SRNLTLTCNL  RKRIIFRKIS  DVKKEEEERL  RQKNEVTLSI

PVDHPVRKLF  QKFKQQKELR  NQGSTQGDPE  RNQLQVESRS  LQNGTSITGT
PVDHPVRKLF  QKFKQQKELR  NQGSAQSDPE  RSQLQVESRP  LQNGASITGT

SVVTVSQITP  IQTSLAYVKT  SESLKQNNRD  AMELKPNGGA  DQKCLKVNSP
SVVTVSQITP  IQTSLAYVKT  SETLKQNNRD  AMELKPNGGA  EPKCLKVNSP

IRMKNGNGKG  WLRLKNNMGA  HEEKKEDWNN  VTKAESMGLL  SEDPKSSDSE
IRMKNGNGKG  WLRLKNNMGA  HEEKKEEWNN  VTKAESMGLL  SEDPKGSDSE

NSVTKNPLRK  TDSCDSGITK  SDLRLDKAGE  ARSPLEHSPI  QADAKHPFYP
NSVTKNPLRK  TDSCDSGITK  SDLRLDKAGE  ARSPLEHSPS  QADAKHPFYP

IPEQALQTTL  QEVKHELKED  IQLLSCRMTA  LEKQVAEILK  ILSEKSVPQA
IPEQALQTTL  QEVKHELKED  IQLLSCRMTA  LEKQVAEILK  LLSEKSVPQT

SSPKSQMPLQ  VPPQIPCQDI  FSVSRPESPE  SDKDEIHF
SSPKPQIPLQ  VPPQIPCQDI  FSVSRPESPE  SDKDEINF
```

Figure 4D

```
K_tetra: domain 1 of 1, from 3 to 101: score 169.0, E = 7.9e-47
   (SEQ ID NO:11)  *->ErvrLNVGGkrFeTsksTLtrfkpdTlLgrllktdsdvhearlrlcd
                      Er++LNV G+rFeT+++TL rf pdTlLg++++        r ++
      12189         3 ERLVLNVAGLRFETRARTLGRF-PDTLLGDPAR----------R-GR 37 fyddetgEyFFDRsPkhFetILnfYRtGdGkLhrp.evcldsfleEleFy
                      fydd++ EyFFDR++++F+++L++Y++G G+L+rp +v+ld+fleE +Fy
      12189        38 FYDDARREYFFDRHRPSFDAVLYYYQSG-GRLRRPaHVPLDVFLEEVAFY 86 gldelaiesCcedeY<-*
                      gl+  a++  +ede+
      12189        87 GLGAAALARLREDEG      101
```

Figure 6A

```
ion_trans: domain 1 of 1, from 198 to 383: score 144.8, E = 1.5e-39
   (SEQ ID NO:9)   *->ilfildllfvllflleivlkfiayglkstsniaakylksifnildll
                      ++f++++l++ +f +e+++++ ++ k      a ++k+++n++d+
      12189       198 PFFVVETLCICWFSFELLVRLLVCPSK------AIFFKNVMNLIDFV 238 ailplllllvlflsgteqvakkrlrerfslelsqwyyrilrflrlLrllR
                      ailp+++ l+ l+++                   ++++ + +L +lR
      12189       239 AILPYFVALGTELARQ-------------------RGVGQQAMSLAILR 268 lLrllrllrrletlfefelgtlaWslqslg.ralksilrfllllllllig
                      ++rl+r++r ++ +    +++    lq+lg+++ +s+ ++ll+++l+ig
      12189       269 VIRLVRVFRIFKLSR---HSKG---LQILGqTLRASMRELGLLIFFLFIG 312 fsvigyllfkgyedlsenevdgnsefssyfdafyflfvtlttvGfGdlvp
                      + +++ ++++ + d+      +s f+s++++f++++vt+ttvG+Gd+ p
      12189       313 VVLFSSAVYFAEVDRV------DSHFTSIPESFWWAVVTMTTVGYGDMAP 356 v.wlgiiffvlffiivglllllnlliavi<-*
                      v+++g+i++ ++++i+g+l+++l+++vi
      12189       357 VtVGGKIVG-SLCAIAGVLTISLPVPVI    383
```

Figure 6B

```
Mouse Kv1.7      MTTRKAQEIH GKAPGGSVST GVGTAEGAPS PAGVTPPPPP RPGRTFHAIF
(SEQ ID NO:13)
12189            .......... .......... .......... .......... ..........

TRRHRTPDWG GCGVGATRPF TGRPGCARHG ATVPAALRCC ERLVLNVAGL
                 .......... .......... .......... ........CC ERLVLNVAGL

RFETRARTLG RFPDTLLGDP VRRSRFYDGA RAEYFFDRHR PSFDAVLYYY
                 RFETRARTLG RFPDTLLGDP ARRGRFYDDA RREYFFDRHR PSFDAVLYYY

QSGGRLRRPA HVPLDVFLEE VSFYGLG.RR LARLREDEGC AVA.ERPLPP
                 QSGGRLRRPA HVPLDVFLEE VAFYGLGAAA LARLREDEGC PVPPERPLPR

.PFARQLWLL FEFPESSQAA RVLAVVSVLV ILVSIVVFCL ETLPDFRDDR
                 RAFARQLCLL FEFPESSQAA RVLAVVSVLV ILVSIVVFCL ETLPDFRDDR

DDPGLAPVAA ATGSFLARLN GSSPMPGAPP RQPFNDPFFV VETLCICWFS
                 DGTGLA.AAA AAGPFPAPLN GSSQMPGNPP RLPFNDPFFV VETLCICWFS

FELLVHLVAC PSKAVFFKNV MNLIDFVAIL PYFVALGTEL ARQRGVGQPA
                 FELLVRLLVC PSKAIFFKNV MNLIDFVAIL PYFVALGTEL ARQRGVGQQA

MSLAILRVIR LVRVFRIFKL SRHSKGLQIL GQTLRASMRE LGLLIFFLFI
                 MSLAILRVIR LVRVFRIFKL SRHSKGLQIL GQTLRASMRE LGLLIFFLFI

GVVLFSSAVY FAEVDRVDTH FTSIPESFWW AVVTMTTVGY GDMAPVTVGG
                 GVVLFSSAVY FAEVDRVDSH FTSIPESFWW AVVTMTTVGY GDMAPVTVGG

KIVGSLCAIA GVLTISLPVP VIVSNFSYFY HRETEGEEAG MYSHVDTQPC
                 KIVGSLCAIA GVLTISLPVP VIVSNFSYFY HRETEGEEAG MFSHVDMQPC

GTLEGKANGG LVDSEVPELL PPLWPPAGKH MVTEV
                 GPLEGKANGG LVDGEVPELP PPLWAPPGKH LVTEV
```

Figure 6C

```
                             SEQUENCE LISTING

<160> NUMBER OF SEQ ID NOS: 13

<210> SEQ ID NO 1
<211> LENGTH: 3525
<212> TYPE: DNA
<213> ORGANISM: Homo sapiens
<220> FEATURE:
<221> NAME/KEY: CDS
<222> LOCATION: (638)...(3178)

<400> SEQUENCE: 1
gcgtccgcag attccagagc ctgccggctg ggaaagatcc ggtctcgggg tcggctatga      60
tcccgcagcg gccaaggcag ggctcaggcc ccgggattct ccccacacgc tgctgcactg     120
gcgcagccgg tcgccaaact ttttctcccc aaagccagtg cccccgcagt tacttggcgg     180
gcagccggca gcccactctc ggcgggatga tctgggagaa gcgggcgtgg gacgaggggg     240
ctgctgtttt gcagccctgc gaggcgtgca gtcggagaag tggtcggggt tccacaccgt     300
ccctgagcct gcccctggc caaggtggcc cgacgtgctg cagtggctgg cgcaggtgat     360
ccgggcagcg cgtccggcac tagtcaaggg ggcagcggca cgggagggag gggcgccttt     420
ctcttttctc ctcccctgc agcccagctg cactgcgtgg gggctctcca tctccacgca     480
atcagcaggc ggaatccctg ccctggagcg ccctggctct ggactgcacc cccctagggt     540
ttgtcctgca gattctcctc cccatctttc tctgccacac acgcttccct aagccgcgcg     600
cgccgcaaac tcagtctcgg tccccgcagg tgatgtc atg ccc att gtt ttg gtg      655
                                        Met Pro Ile Val Leu Val
                                         1               5 cgc cca acc aat cgg act cgc cgc ctg gat tct acc gga gcc ggc atg       703
Arg Pro Thr Asn Arg Thr Arg Arg Leu Asp Ser Thr Gly Ala Gly Met
             10                  15                  20 ggc cct tcc tcg cac cag cag cag gag tcc ccg ctc ccg acc ata acg       751
Gly Pro Ser Ser His Gln Gln Gln Glu Ser Pro Leu Pro Thr Ile Thr
         25                  30                  35 cat tgc gca ggg tgc acc acc gct tgg tct ccc tgc agc ttt aac agc       799
His Cys Ala Gly Cys Thr Thr Ala Trp Ser Pro Cys Ser Phe Asn Ser
     40                  45                  50 cct gac atg gaa acc cca ttg cag ttc cag cgc ggc ttc ttc cca gag       847
Pro Asp Met Glu Thr Pro Leu Gln Phe Gln Arg Gly Phe Phe Pro Glu
 55                  60                  65                  70 cag ccg ccg ccg ccg ccg cgc tcc tca cac ctg cat tgc cag cag cag       895
Gln Pro Pro Pro Pro Pro Arg Ser Ser His Leu His Cys Gln Gln Gln
                 75                  80                  85 caa cag agc cag gac aag ccg tgc ccg ccc ttc gcg ccc ctc ccg cac       943
Gln Gln Ser Gln Asp Lys Pro Cys Pro Pro Phe Ala Pro Leu Pro His
             90                  95                 100 cct cac cac cac ccg cac ctc gcg cac cag cag ccg gcc agc ggc ggc       991
Pro His His His Pro His Leu Ala His Gln Gln Pro Ala Ser Gly Gly
```

-continued

|     |     |     |     | 105 |     |     |     |     | 110 |     |     |     |     | 115 |     |      |
|-----|-----|-----|-----|-----|-----|-----|-----|-----|-----|-----|-----|-----|-----|-----|-----|------|
| agc | agc | cca | tgc | ctc | cgg | tgc | aac | agc | tgc | gcc | tcc | tcc | ggt | gcc | ccg | 1039 |
| Ser | Ser | Pro | Cys | Leu | Arg | Cys | Asn | Ser | Cys | Ala | Ser | Ser | Gly | Ala | Pro |      |
|     | 120 |     |     |     |     | 125 |     |     |     |     | 130 |     |     |     |     |      | gcg gcg ggg gcg gga gat aac ctg tcc ctg ctg ctc cgc acc tcc tcg    1087
Ala Ala Gly Ala Gly Asp Asn Leu Ser Leu Leu Leu Arg Thr Ser Ser
135                 140                 145                 150 ccc ggc ggc gcc ttc cgg acc cgc acc tcc tcg ccg ctg tcg ggc tcg    1135
Pro Gly Gly Ala Phe Arg Thr Arg Thr Ser Ser Pro Leu Ser Gly Ser
            155                 160                 165 tcc tgc tgc tgc tgc tgc tcg tcg cgc cgg ggc agc cag ctc aat        1183
Ser Cys Cys Cys Cys Cys Ser Ser Arg Arg Gly Ser Gln Leu Asn
                170                 175                 180 gtg agc gag ctg acg ccg tcc agc cat gcc agt gcg ctc cgg cag cag    1231
Val Ser Glu Leu Thr Pro Ser Ser His Ala Ser Ala Leu Arg Gln Gln
        185                 190                 195 tac gcg cag cag tcc gcg cag cag tcg gcg tcc gcc tcc cag tac cac    1279
Tyr Ala Gln Gln Ser Ala Gln Gln Ser Ala Ser Ala Ser Gln Tyr His
    200                 205                 210 cag tgc cac agc ctg cag ccc gcc gcc agc ccc acg ggc agc ctc ggc    1327
Gln Cys His Ser Leu Gln Pro Ala Ala Ser Pro Thr Gly Ser Leu Gly
215                 220                 225                 230 agt ctg ggc tcc ggg ccc ccg ctc tcg cac cac cac cac cac ccg cac    1375
Ser Leu Gly Ser Gly Pro Pro Leu Ser His His His His His Pro His
            235                 240                 245 ccg gcg cac cac cag cac cac cag ccc cag gcg cgc cgc gag agc aac    1423
Pro Ala His His Gln His His Gln Pro Gln Ala Arg Arg Glu Ser Asn
        250                 255                 260 ccc ttc acc gaa ata gcc atg agc agc tgc agg tac aac ggg ggc gtc    1471
Pro Phe Thr Glu Ile Ala Met Ser Ser Cys Arg Tyr Asn Gly Gly Val
    265                 270                 275 atg cgg ccg ctc agc aac ttg agc gcg tcc cgc cgg aac ctg cac gag    1519
Met Arg Pro Leu Ser Asn Leu Ser Ala Ser Arg Arg Asn Leu His Glu
280                 285                 290 atg gac tca gag gcg cag ccc ctg cag ccc ccg gcg tct gtc gga gga    1567
Met Asp Ser Glu Ala Gln Pro Leu Gln Pro Pro Ala Ser Val Gly Gly
295                 300                 305                 310 ggt ggc ggc gcg tcc tcc ccg tct gca gcc gct gcc gcc gcc gcc gct    1615
Gly Gly Gly Ala Ser Ser Pro Ser Ala Ala Ala Ala Ala Ala Ala Ala
            315                 320                 325 gtt tcg tcc tca gcc ccc gag atc gtg gtg tct aag ccc gag cac aac    1663
Val Ser Ser Ser Ala Pro Glu Ile Val Val Ser Lys Pro Glu His Asn
        330                 335                 340 aac tcc aac aac ctg gcg ctc tat gga acc ggc ggc gga ggc agc act    1711
Asn Ser Asn Asn Leu Ala Leu Tyr Gly Thr Gly Gly Gly Gly Ser Thr
    345                 350                 355 gga gga ggc ggc ggc ggt ggc ggg agc ggg cac ggc agc agc agt ggc    1759
Gly Gly Gly Gly Gly Gly Gly Ser Gly His Gly Ser Ser Ser Gly
360                 365                 370 acc aag tcc agc aaa aag aaa aac cag aac atc ggc tac aag ctg ggc    1807
Thr Lys Ser Ser Lys Lys Lys Asn Gln Asn Ile Gly Tyr Lys Leu Gly
375                 380                 385                 390 cac cgg cgc gcc ctg ttc gaa aag cgc aag cgg ctc agc gac tac gcg    1855
His Arg Arg Ala Leu Phe Glu Lys Arg Lys Arg Leu Ser Asp Tyr Ala
            395                 400                 405 ctc atc ttc ggc atg ttc ggc atc gtg gtc atg gtc atc gag acc gag    1903
Leu Ile Phe Gly Met Phe Gly Ile Val Val Met Val Ile Glu Thr Glu
        410                 415                 420 ctg tcg tgg ggc gcc tac gac aag gcg tcg ctg tat tcc tta gct ctg    1951

```
                                                                 -continued

Leu Ser Trp Gly Ala Tyr Asp Lys Ala Ser Leu Tyr Ser Leu Ala Leu
        425                 430                 435 aaa tgc ctt atc agt ctc tcc acg atc atc ctg ctc ggt ctg atc atc    1999
Lys Cys Leu Ile Ser Leu Ser Thr Ile Ile Leu Leu Gly Leu Ile Ile
    440                 445                 450 gtg tac cac gcc agg gaa ata cag ttg ttc atg gtg gac aat gga gca    2047
Val Tyr His Ala Arg Glu Ile Gln Leu Phe Met Val Asp Asn Gly Ala
455                 460                 465                 470 gat gac tgg aga ata gcc atg act tat gag cgt att ttc ttc atc tgc    2095
Asp Asp Trp Arg Ile Ala Met Thr Tyr Glu Arg Ile Phe Phe Ile Cys
                475                 480                 485 ttg gaa ata ctg gtg tgt gct att cat ccc ata cct ggg aat tat aca    2143
Leu Glu Ile Leu Val Cys Ala Ile His Pro Ile Pro Gly Asn Tyr Thr
        490                 495                 500 ttc aca tgg acg gcc cgg ctt gcc ttc tcc tat gcc cca tcc aca acc    2191
Phe Thr Trp Thr Ala Arg Leu Ala Phe Ser Tyr Ala Pro Ser Thr Thr
            505                 510                 515 acc gct gat gtg gat att att tta tct ata cca atg ttc tta aga ctc    2239
Thr Ala Asp Val Asp Ile Ile Leu Ser Ile Pro Met Phe Leu Arg Leu
    520                 525                 530 tat ctg att gcc aga gtc atg ctt tta cat agc aaa ctt ttc act gat    2287
Tyr Leu Ile Ala Arg Val Met Leu Leu His Ser Lys Leu Phe Thr Asp
535                 540                 545                 550 acc tcc tct aga agc att gga gca ctt aat aag ata aac ttc aat aca    2335
Thr Ser Ser Arg Ser Ile Gly Ala Leu Asn Lys Ile Asn Phe Asn Thr
                555                 560                 565 cgt ttt gtt atg aag act tta atg act ata tgc cca gga act gta ctc    2383
Arg Phe Val Met Lys Thr Leu Met Thr Ile Cys Pro Gly Thr Val Leu
        570                 575                 580 ttg gtt ttt agt atc tca tta tgg ata att gcc gca tgg act gtc cga    2431
Leu Val Phe Ser Ile Ser Leu Trp Ile Ile Ala Ala Trp Thr Val Arg
            585                 590                 595 gct tgt gaa agg tac cat gat caa cag gat gtt act agc aac ttc ctt    2479
Ala Cys Glu Arg Tyr His Asp Gln Gln Asp Val Thr Ser Asn Phe Leu
    600                 605                 610 gga gcg atg tgg ttg ata tca ata act ttt ctc tcc att ggt tat ggt    2527
Gly Ala Met Trp Leu Ile Ser Ile Thr Phe Leu Ser Ile Gly Tyr Gly
615                 620                 625                 630 gac atg gta cct aac aca tac tgt gga aaa gga gtc tgc tta ctt act    2575
Asp Met Val Pro Asn Thr Tyr Cys Gly Lys Gly Val Cys Leu Leu Thr
                635                 640                 645 gga att atg ggt gct ggt tgc aca gcc ctg gtg gta gct gta gtg gca    2623
Gly Ile Met Gly Ala Gly Cys Thr Ala Leu Val Val Ala Val Val Ala
        650                 655                 660 agg aag cta gaa ctt acc aaa gca gaa aaa cac gtg cac aat ttc atg    2671
Arg Lys Leu Glu Leu Thr Lys Ala Glu Lys His Val His Asn Phe Met
            665                 670                 675 atg gat act cag ctg act aaa aga gta aaa aat gca gct gcc aat gta    2719
Met Asp Thr Gln Leu Thr Lys Arg Val Lys Asn Ala Ala Ala Asn Val
    680                 685                 690 ctc agg gaa aca tgg cta att tac aaa aat aca aag cta gtg aaa aag    2767
Leu Arg Glu Thr Trp Leu Ile Tyr Lys Asn Thr Lys Leu Val Lys Lys
695                 700                 705                 710 ata gat cat gca aaa gta aga aaa cat caa cga aaa ttc ctg caa gct    2815
Ile Asp His Ala Lys Val Arg Lys His Gln Arg Lys Phe Leu Gln Ala
                715                 720                 725 att cat caa tta aga agt gta aaa atg gag cag agg aaa ctg aat gac    2863
Ile His Gln Leu Arg Ser Val Lys Met Glu Gln Arg Lys Leu Asn Asp
        730                 735                 740
```

```
caa gca aac act ttg gtg gac ttg gca aag acc cag aac atc atg tat    2911
Gln Ala Asn Thr Leu Val Asp Leu Ala Lys Thr Gln Asn Ile Met Tyr
        745                 750                 755 gat atg att tct gac tta aac gaa agg agt gaa gac ttc gag aag agg    2959
Asp Met Ile Ser Asp Leu Asn Glu Arg Ser Glu Asp Phe Glu Lys Arg
760                 765                 770 att gtt acc ctg gaa aca aaa cta gag act ttg att ggt agc atc cac    3007
Ile Val Thr Leu Glu Thr Lys Leu Glu Thr Leu Ile Gly Ser Ile His
775                 780                 785                 790 gcc ctc cct ggg ctc ata agc cag acc atc agg cag cag cag aga gat    3055
Ala Leu Pro Gly Leu Ile Ser Gln Thr Ile Arg Gln Gln Gln Arg Asp
                795                 800                 805 ttc att gag gct cag atg gag agc tac gac aag cac gtc act tac aat    3103
Phe Ile Glu Ala Gln Met Glu Ser Tyr Asp Lys His Val Thr Tyr Asn
            810                 815                 820 gct gag cgg tcc cgg tcc tcg tcc agg agg cgg cgg tcc tct tcc aca    3151
Ala Glu Arg Ser Arg Ser Ser Ser Arg Arg Arg Arg Ser Ser Ser Thr
        825                 830                 835 gca cca cca act tca tca gag agt agc tagaagagaa taagttaacc          3198
Ala Pro Pro Thr Ser Ser Glu Ser Ser
    840                 845 acaaaataag acttttgcc atcatatggt caatatttta gcttttattg taaagcccct   3258
atggttctaa tcagcgttat ccgggttctg atgtcagaat cctgggaacc tgaacactaa  3318
gttttaggcc aaaatgagtg aaaactcttt ttttttcttt cagatgcaca gggaatgcac  3378
ctattattgc tatatagatt gttcctcctg taatttcact aacttttat tcatgcactt   3438 caaacaaact ttactactac attatatgat atataataaa aaaagttaat ttctgcaaaa  3498
aaaaaaaaaa aaaaaaaaac ggacggg                                     3525

<210> SEQ ID NO 2
<211> LENGTH: 847
<212> TYPE: PRT
<213> ORGANISM: Homo sapiens

<400> SEQUENCE: 2

Met Pro Ile Val Leu Val Arg Pro Thr Asn Arg Thr Arg Arg Leu Asp
1               5                   10                  15

Ser Thr Gly Ala Gly Met Gly Pro Ser Ser His Gln Gln Gln Glu Ser
            20                  25                  30

Pro Leu Pro Thr Ile Thr His Cys Ala Gly Cys Thr Thr Ala Trp Ser
        35                  40                  45

Pro Cys Ser Phe Asn Ser Pro Asp Met Glu Thr Pro Leu Gln Phe Gln
    50                  55                  60

Arg Gly Phe Phe Pro Glu Gln Pro Pro Pro Arg Ser Ser His
65                  70                  75                  80

Leu His Cys Gln Gln Gln Gln Ser Gln Asp Lys Pro Cys Pro Pro
                85                  90                  95

Phe Ala Pro Leu Pro His Pro His His Pro His Leu Ala His Gln
            100                 105                 110

Gln Pro Ala Ser Gly Gly Ser Ser Pro Cys Leu Arg Cys Asn Ser Cys
        115                 120                 125

Ala Ser Ser Gly Ala Pro Ala Gly Ala Gly Asp Asn Leu Ser Leu
    130                 135                 140

Leu Leu Arg Thr Ser Ser Pro Gly Gly Ala Phe Arg Thr Arg Thr Ser
145                 150                 155                 160

Ser Pro Leu Ser Gly Ser Ser Cys Cys Cys Cys Cys Cys Ser Ser Arg
```

-continued

```
                165                 170                 175
Arg Gly Ser Gln Leu Asn Val Ser Glu Leu Thr Pro Ser Ser His Ala
            180                 185                 190
Ser Ala Leu Arg Gln Gln Tyr Ala Gln Gln Ser Ala Gln Gln Ser Ala
        195                 200                 205
Ser Ala Ser Gln Tyr His Gln Cys His Ser Leu Gln Pro Ala Ala Ser
    210                 215                 220
Pro Thr Gly Ser Leu Gly Ser Leu Gly Ser Gly Pro Pro Leu Ser His
225                 230                 235                 240
His His His His Pro His Pro Ala His Gln His His Gln Pro Gln
                245                 250                 255
Ala Arg Arg Glu Ser Asn Pro Phe Thr Glu Ile Ala Met Ser Ser Cys
            260                 265                 270
Arg Tyr Asn Gly Gly Val Met Arg Pro Leu Ser Asn Leu Ser Ala Ser
        275                 280                 285
Arg Arg Asn Leu His Glu Met Asp Ser Glu Ala Gln Pro Leu Gln Pro
    290                 295                 300
Pro Ala Ser Val Gly Gly Gly Gly Ala Ser Ser Pro Ser Ala Ala
305                 310                 315                 320
Ala Ala Ala Ala Ala Val Ser Ser Ala Pro Glu Ile Val Val
                325                 330                 335
Ser Lys Pro Glu His Asn Asn Ser Asn Asn Leu Ala Leu Tyr Gly Thr
            340                 345                 350
Gly Gly Gly Gly Ser Thr Gly Gly Gly Gly Gly Gly Ser Gly
        355                 360                 365
His Gly Ser Ser Gly Thr Lys Ser Lys Lys Lys Asn Gln Asn
    370                 375                 380
Ile Gly Tyr Lys Leu Gly His Arg Arg Ala Leu Phe Glu Lys Arg Lys
385                 390                 395                 400
Arg Leu Ser Asp Tyr Ala Leu Ile Phe Gly Met Phe Gly Ile Val Val
                405                 410                 415
Met Val Ile Glu Thr Glu Leu Ser Trp Gly Ala Tyr Asp Lys Ala Ser
            420                 425                 430
Leu Tyr Ser Leu Ala Leu Lys Cys Leu Ile Ser Leu Ser Thr Ile Ile
        435                 440                 445
Leu Leu Gly Leu Ile Ile Val Tyr His Ala Arg Glu Ile Gln Leu Phe
    450                 455                 460
Met Val Asp Asn Gly Ala Asp Asp Trp Arg Ile Ala Met Thr Tyr Glu
465                 470                 475                 480
Arg Ile Phe Phe Ile Cys Leu Glu Ile Leu Val Cys Ala Ile His Pro
                485                 490                 495
Ile Pro Gly Asn Tyr Thr Phe Thr Trp Thr Ala Arg Leu Ala Phe Ser
            500                 505                 510
Tyr Ala Pro Ser Thr Thr Ala Asp Val Asp Ile Leu Ser Ile
        515                 520                 525
Pro Met Phe Leu Arg Leu Tyr Leu Ile Ala Arg Val Met Leu Leu His
    530                 535                 540
Ser Lys Leu Phe Thr Asp Thr Ser Ser Arg Ser Ile Gly Ala Leu Asn
545                 550                 555                 560
Lys Ile Asn Phe Asn Thr Arg Phe Val Met Lys Thr Leu Met Thr Ile
                565                 570                 575
Cys Pro Gly Thr Val Leu Leu Val Phe Ser Ile Ser Leu Trp Ile Ile
            580                 585                 590
```

```
Ala Ala Trp Thr Val Arg Ala Cys Glu Arg Tyr His Asp Gln Gln Asp
            595                 600                 605

Val Thr Ser Asn Phe Leu Gly Ala Met Trp Leu Ile Ser Ile Thr Phe
        610                 615                 620

Leu Ser Ile Gly Tyr Gly Asp Met Val Pro Asn Thr Tyr Cys Gly Lys
625                 630                 635                 640

Gly Val Cys Leu Leu Thr Gly Ile Met Gly Ala Gly Cys Thr Ala Leu
                645                 650                 655

Val Val Ala Val Val Ala Arg Lys Leu Glu Leu Thr Lys Ala Glu Lys
            660                 665                 670

His Val His Asn Phe Met Met Asp Thr Gln Leu Thr Lys Arg Val Lys
        675                 680                 685

Asn Ala Ala Asn Val Leu Arg Glu Thr Trp Leu Ile Tyr Lys Asn
    690                 695                 700

Thr Lys Leu Val Lys Lys Ile Asp His Ala Lys Val Arg Lys His Gln
705                 710                 715                 720

Arg Lys Phe Leu Gln Ala Ile His Gln Leu Arg Ser Val Lys Met Glu
                725                 730                 735

Gln Arg Lys Leu Asn Asp Gln Ala Asn Thr Leu Val Asp Leu Ala Lys
            740                 745                 750

Thr Gln Asn Ile Met Tyr Asp Met Ile Ser Asp Leu Asn Glu Arg Ser
        755                 760                 765

Glu Asp Phe Glu Lys Arg Ile Val Thr Leu Glu Thr Lys Leu Glu Thr
770                 775                 780

Leu Ile Gly Ser Ile His Ala Leu Pro Gly Leu Ile Ser Gln Thr Ile
785                 790                 795                 800

Arg Gln Gln Gln Arg Asp Phe Ile Glu Ala Gln Met Glu Ser Tyr Asp
                805                 810                 815

Lys His Val Thr Tyr Asn Ala Glu Arg Ser Arg Ser Ser Arg Arg
            820                 825                 830

Arg Arg Ser Ser Ser Thr Ala Pro Pro Thr Ser Ser Glu Ser Ser
        835                 840                 845

<210> SEQ ID NO 3
<211> LENGTH: 2544
<212> TYPE: DNA
<213> ORGANISM: Homo sapiens

<400> SEQUENCE: 3
atgcccattg ttttggtgcg cccaaccaat cggactcgcc gcctggattc taccggagcc      60
ggcatgggcc cttcctcgca ccagcagcag gagtccccgc tcccgaccat aacgcattgc     120 gcaggtgca ccaccgcttg gtctccctgc agctttaaca gccctgacat ggaaacccca      180
ttgcagttcc agcgcggctt cttcccagag cagccgccgc cgccgccgcg ctcctcacac     240
ctgcattgcc agcagcagca acagagccag gacaagccgt gcccgccctt cgcgcccctc     300
ccgcaccctc accaccaccc gcacctcgcg caccagcagc cggccagcgg cggcagcagc     360
ccatgcctcc ggtgcaacag ctgcgcctcc tccggtgccc cggcggcggg ggcgggagat     420
aacctgtccc tgctgctccg cacctcctcg cccggcggcg ccttccggac ccgcacctcc     480
tcgccgctgt cgggctcgtc ctgctgctgc tgctgctgct cgtcgcgccg gggcagccag     540
ctcaatgtga gcgagctgac gccgtccagc catgccagtg cgctccggca gcagtacgcg     600
cagcagtccg cgcagcagtc ggcgtccgcc tcccagtacc accagtgcca cagcctgcag     660
```

```
cccgccgcca gccccacggg cagcctcggc agtctgggct ccgggccccc gctctcgcac    720
caccaccacc acccgcaccc ggcgcaccac cagcaccacc agccccaggc gcgccgcgag    780 agcaaccccct tcaccgaaat agccatgagc agctgcaggt acaacggggg cgtcatgcgg    840
ccgctcagca acttgagcgc gtcccgccgg aacctgcacg agatggactc agaggcgcag    900
cccctgcagc cccccgcgtc tgtcggagga ggtggcggcg cgtcctcccc gtctgcagcc    960
gctgccgccg ccgccgctgt ttcgtcctca gcccccgaga tcgtggtgtc taagcccgag   1020
cacaacaact ccaacaacct ggcgctctat ggaaccggcg gcggaggcag cactggagga   1080
ggcggcggcg gtggcgggag cgggcacggc agcagcagtg gcaccaagtc cagcaaaaag   1140
aaaaaccaga acatcggcta caagctgggc caccggcgcg ccctgttcga aaagcgcaag   1200
cggctcagcg actacgcgct catcttcggc atgttcggca tcgtggtcat ggtcatcgag   1260
accgagctgt cgtggggcgc ctacgacaag gcgtcgctgt attccttagc tctgaaatgc   1320
cttatcagtc tctccacgat catcctgctc ggtctgatca tcgtgtacca cgccagggaa   1380
atacagttgt tcatggtgga caatggagca gatgactgga gaatagccat gacttatgag   1440 cgtatttttct tcatctgctt ggaaatactg gtgtgtgcta ttcatcccat acctgggaat   1500
tatacattca catggacggc ccggcttgcc ttctcctatg ccccatccac aaccaccgct   1560
gatgtggata ttatttttatc tataccaatg ttcttaagac tctatctgat tgccagagtc   1620
atgcttttac atagcaaact tttcactgat acctcctcta aagcattgg agcacttaat    1680 aagataaact tcaatacacg ttttgttatg aagactttaa tgactatatg cccaggaact   1740
gtactcttgg ttttttagtat ctcattatgg ataattgccg catggactgt ccgagcttgt   1800
gaaaggtacc atgatcaaca ggatgttact agcaacttcc ttggagcgat gtggttgata   1860
tcaataactt ttctctccat tggttatggt gacatggtac ctaacacata ctgtggaaaa   1920
ggagtctgct tacttactgg aattatgggt gctggttgca cagccctggt ggtagctgta   1980
gtggcaagga agctagaact taccaaagca gaaaaacacg tgcacaattt catgatggat   2040
actcagctga ctaaaagagt aaaaaatgca gctgccaatg tactcaggga acatggccta   2100
atttacaaaa atacaaagct agtgaaaaag atagatcatg caaaagtaag aaaacatcaa   2160
cgaaaattcc tgcaagctat tcatcaatta agaagtgtaa aaatggagca gaggaaactg   2220
aatgaccaag caaacacttt ggtggacttg gcaaagaccc agaacatcat gtatgatatg   2280
atttctgact taaacgaaag gagtgaagac ttcgagaaga ggattgttac cctggaaaca   2340
aaactagaga ctttgattgg tagcatccac gccctccctg ggctcataag ccagaccatc   2400
aggcagcagc agagagattt cattgaggct cagatggaga gctacgacaa gcacgtcact   2460
tacaatgctg agcggtcccg gtcctcgtcc aggaggcggc ggtcctcttc cacagcacca   2520
ccaacttcat cagagagtag ctag                                          2544

<210> SEQ ID NO 4
<211> LENGTH: 3553
<212> TYPE: DNA
<213> ORGANISM: Homo sapiens
<220> FEATURE:
<221> NAME/KEY: CDS
<222> LOCATION: (278)...(3241)

<400> SEQUENCE: 4
gacccacgcg tccgctcccc cgtgtgcggc accgccacag tctgggcagc ggcggccggg     60
ggagcgctac taccatgaac tgcctggtcc tcctccccag agctgctcat ccgggtcggg    120
```

-continued

```
ctggagacac agtcagggga ccccgtcgcc gccgccgcgc ccctcttct ttcggctcaa      180 tcttctcttc caccttttcc tcctcttcct ccacttcttt tgcctgcatc cccccctccc      240
ccgccgcgga tcctggccgc tgctctccag acccagg atg ccg ggg ggc aag aga      295
                                          Met Pro Gly Gly Lys Arg
                                            1               5 ggg ctg gtg gca ccg cag aac aca ttt ttg gag aac atc gtc agg cgc      343
Gly Leu Val Ala Pro Gln Asn Thr Phe Leu Glu Asn Ile Val Arg Arg
              10                  15                  20 tcc agt gaa tca agt ttc tta ctg gga aat gcc cag att gtg gat tgg      391
Ser Ser Glu Ser Ser Phe Leu Leu Gly Asn Ala Gln Ile Val Asp Trp
          25                  30                  35 cct gta gtt tat agt aat gac ggt ttt tgt aaa ctc tct gga tat cat      439
Pro Val Val Tyr Ser Asn Asp Gly Phe Cys Lys Leu Ser Gly Tyr His
      40                  45                  50 cga gct gac gtc atg cag aaa agc agc act tgc agt ttt atg tat ggg      487
Arg Ala Asp Val Met Gln Lys Ser Ser Thr Cys Ser Phe Met Tyr Gly
 55                  60                  65                  70 gaa ttg act gac aag aag acc att gag aaa gtc agg caa act ttt gac      535
Glu Leu Thr Asp Lys Lys Thr Ile Glu Lys Val Arg Gln Thr Phe Asp
              75                  80                  85 aac tac gaa tca aac tgc ttt gaa gtt ctg tac aag aaa aac aga      583
Asn Tyr Glu Ser Asn Cys Phe Glu Val Leu Leu Tyr Lys Lys Asn Arg
          90                  95                 100 acc cct gtt tgg ttt tat atg caa att gca cca ata aga aat gaa cat      631
Thr Pro Val Trp Phe Tyr Met Gln Ile Ala Pro Ile Arg Asn Glu His
     105                 110                 115 gaa aag gtc gtc ttg ttc ctg tgt act ttc aag gat att acg ttg ttc      679
Glu Lys Val Val Leu Phe Leu Cys Thr Phe Lys Asp Ile Thr Leu Phe
 120                 125                 130 aaa cag cca ata gag gat gat tca aca aaa ggt tgg acg aaa ttt gcc      727
Lys Gln Pro Ile Glu Asp Asp Ser Thr Lys Gly Trp Thr Lys Phe Ala
135                 140                 145                 150 cga ttg aca cgg gct ttg aca aat agc cga agt gtt tgc cag cag ctc      775
Arg Leu Thr Arg Ala Leu Thr Asn Ser Arg Ser Val Leu Gln Gln Leu
             155                 160                 165 acg cca atg aat aaa aca gag gtg gtc cat aaa cat tca aga cta gct      823
Thr Pro Met Asn Lys Thr Glu Val Val His Lys His Ser Arg Leu Ala
         170                 175                 180 gaa gtt ctt cag ctg gga tca gat atc ctt cct cag tat aaa caa gaa      871
Glu Val Leu Gln Leu Gly Ser Asp Ile Leu Pro Gln Tyr Lys Gln Glu
     185                 190                 195 gcg cca aag acg cca cca cac att att tta cat tat tgt gct ttt aaa      919
Ala Pro Lys Thr Pro Pro His Ile Ile Leu His Tyr Cys Ala Phe Lys
 200                 205                 210 act act tgg gat tgg gtg att tta att ctt acc ttc tac acc gcc att      967
Thr Thr Trp Asp Trp Val Ile Leu Ile Leu Thr Phe Tyr Thr Ala Ile
215                 220                 225                 230 atg gtt cct tat aat gtt tcc ttc aaa aca aag cag aac aac ata gcc     1015
Met Val Pro Tyr Asn Val Ser Phe Lys Thr Lys Gln Asn Asn Ile Ala
             235                 240                 245 tgg ctg gta ctg gat agt gtg gtg gac gtt att ttt ctg gtt gac atc     1063
Trp Leu Val Leu Asp Ser Val Val Asp Val Ile Phe Leu Val Asp Ile
         250                 255                 260 gtt tta aat ttt cac acg act ttc gtg ggg ccc ggt gga gag gtc att     1111
Val Leu Asn Phe His Thr Thr Phe Val Gly Pro Gly Gly Glu Val Ile
     265                 270                 275 tct gac cct aag ctc ata agg atg aac tat ctg aaa act tgg ttt gtg     1159
Ser Asp Pro Lys Leu Ile Arg Met Asn Tyr Leu Lys Thr Trp Phe Val
 280                 285                 290
```

-continued

| | |
|---|---|
| atc gat ctg ctg tct tgt tta cct tat gac atc atc aat gcc ttt gaa<br>Ile Asp Leu Leu Ser Cys Leu Pro Tyr Asp Ile Ile Asn Ala Phe Glu<br>295                              300                        305                        310 | 1207 |
| aat gtg gat gag gga atc agc agt ctc ttc agt tct tta aaa gtg gtg<br>Asn Val Asp Glu Gly Ile Ser Ser Leu Phe Ser Ser Leu Lys Val Val<br>                        315                        320                        325 | 1255 |
| cgt ctc tta cga ctg ggc cgt gtg gct agg aaa ctg gac cat tac cta<br>Arg Leu Leu Arg Leu Gly Arg Val Ala Arg Lys Leu Asp His Tyr Leu<br>            330                        335                        340 | 1303 |
| gaa tat gga gca gca gtc ctc gtg ctc ctg gtg tgt gtg ttt gga ctg<br>Glu Tyr Gly Ala Ala Val Leu Val Leu Leu Val Cys Val Phe Gly Leu<br>                345                        350                        355 | 1351 |
| gtg gcc cac tgg ctg gcc tgc ata tgg tat agc atc gga gac tac gag<br>Val Ala His Trp Leu Ala Cys Ile Trp Tyr Ser Ile Gly Asp Tyr Glu<br>360                            365                        370 | 1399 |
| gtc att gat gaa gtc act aac acc atc caa ata gac agt tgg ctc tac<br>Val Ile Asp Glu Val Thr Asn Thr Ile Gln Ile Asp Ser Trp Leu Tyr<br>375                            380                        385                        390 | 1447 |
| cag ctg gct ttg agc att ggg act cca tat cgc tac aat acc agt gct<br>Gln Leu Ala Leu Ser Ile Gly Thr Pro Tyr Arg Tyr Asn Thr Ser Ala<br>                        395                        400                        405 | 1495 |
| ggg ata tgg gaa gga gga ccc agc aag gat tca ttg tac gtg tcc tct<br>Gly Ile Trp Glu Gly Gly Pro Ser Lys Asp Ser Leu Tyr Val Ser Ser<br>                410                        415                        420 | 1543 |
| ctc tac ttt acc atg aca agc ctt aca acc ata gga ttt gga aac ata<br>Leu Tyr Phe Thr Met Thr Ser Leu Thr Thr Ile Gly Phe Gly Asn Ile<br>                425                        430                        435 | 1591 |
| gct cct acc aca gat gtg gag aag atg ttt tcg gtg gct atg atg atg<br>Ala Pro Thr Thr Asp Val Glu Lys Met Phe Ser Val Ala Met Met Met<br>440                            445                        450 | 1639 |
| gtt ggc tct ctt ctt tat gca act att ttt gga aat gtt aca aca att<br>Val Gly Ser Leu Leu Tyr Ala Thr Ile Phe Gly Asn Val Thr Thr Ile<br>455                            460                        465                        470 | 1687 |
| ttc cag caa atg tat gcc aac acc aac cga tac cat gag atg ctg aat<br>Phe Gln Gln Met Tyr Ala Asn Thr Asn Arg Tyr His Glu Met Leu Asn<br>                        475                        480                        485 | 1735 |
| aat gta cgg gac ttc cta aaa ctc tat cag gtc cca aaa ggc ctt agt<br>Asn Val Arg Asp Phe Leu Lys Leu Tyr Gln Val Pro Lys Gly Leu Ser<br>            490                        495                        500 | 1783 |
| gag cga gtc atg gat tat att gtc tca aca tgg tcc atg tca aaa ggc<br>Glu Arg Val Met Asp Tyr Ile Val Ser Thr Trp Ser Met Ser Lys Gly<br>                505                        510                        515 | 1831 |
| att gat aca gaa aag gtc ctc tcc atc tgt ccc aag gac atg aga gct<br>Ile Asp Thr Glu Lys Val Leu Ser Ile Cys Pro Lys Asp Met Arg Ala<br>520                              525                        530 | 1879 |
| gat atc tgt gtt cat cta aac cgg aag gtt ttt aat gaa cat cct gct<br>Asp Ile Cys Val His Leu Asn Arg Lys Val Phe Asn Glu His Pro Ala<br>535                            540                        545                        550 | 1927 |
| ttt cga ttg gcc agc gat ggg tgt ctg cgc gcc ttg gcg gta gag ttc<br>Phe Arg Leu Ala Ser Asp Gly Cys Leu Arg Ala Leu Ala Val Glu Phe<br>                        555                        560                        565 | 1975 |
| caa acc att cac tgt gct ccc ggg gac ctc att tac cat gct gga gaa<br>Gln Thr Ile His Cys Ala Pro Gly Asp Leu Ile Tyr His Ala Gly Glu<br>                570                        575                        580 | 2023 |
| agt gtg gat gcc ctc tgc ttt gtg gtg tca gga tcc ttg gaa gtc atc<br>Ser Val Asp Ala Leu Cys Phe Val Val Ser Gly Ser Leu Glu Val Ile<br>585                            590                        595 | 2071 |
| cag gat gat gag gtg gtg gct att tta ggg aag ggt gat gta ttt gga<br>Gln Asp Asp Glu Val Val Ala Ile Leu Gly Lys Gly Asp Val Phe Gly | 2119 |

```
                            -continued 600              605              610
gac atc ttc tgg aag gaa acc acc ctt gcc cat gca tgt gcg aac gtc    2167
Asp Ile Phe Trp Lys Glu Thr Thr Leu Ala His Ala Cys Ala Asn Val
615                 620                 625                 630 cgg gca ctg acg tac tgt gac cta cac atc atc aag cgg gaa gcc ttg    2215
Arg Ala Leu Thr Tyr Cys Asp Leu His Ile Ile Lys Arg Glu Ala Leu
                635                 640                 645 ctc aaa gtc ctg gac ttt tat aca gct ttt gca aac tcc ttc tca agg    2263
Leu Lys Val Leu Asp Phe Tyr Thr Ala Phe Ala Asn Ser Phe Ser Arg
            650                 655                 660 aat ctc act ctt act tgc aat ctg agg aaa cgg atc atc ttt cgt aag    2311
Asn Leu Thr Leu Thr Cys Asn Leu Arg Lys Arg Ile Ile Phe Arg Lys
        665                 670                 675 atc agt gat gtg aag aaa gag gag gag gag cgc ctc cgg cag aag aat    2359
Ile Ser Asp Val Lys Lys Glu Glu Glu Glu Arg Leu Arg Gln Lys Asn
    680                 685                 690 gag gtg acc ctc agc att ccc gtg gac cac cca gtc aga aag ctc ttc    2407
Glu Val Thr Leu Ser Ile Pro Val Asp His Pro Val Arg Lys Leu Phe
695                 700                 705                 710 cag aag ttc aag cag cag aag gag ctg cgg aat cag ggc tca aca cag    2455
Gln Lys Phe Lys Gln Gln Lys Glu Leu Arg Asn Gln Gly Ser Thr Gln
                715                 720                 725 ggt gac cct gag agg aac caa ctc cag gta gag agc cgc tcc tta cag    2503
Gly Asp Pro Glu Arg Asn Gln Leu Gln Val Glu Ser Arg Ser Leu Gln
            730                 735                 740 aat gga acc tcc atc acc gga acc agc gtg gtg act gtg tca cag att    2551
Asn Gly Thr Ser Ile Thr Gly Thr Ser Val Val Thr Val Ser Gln Ile
        745                 750                 755 act ccc att cag acg tct ctg gcc tat gtg aaa acc agt gaa tcc ctt    2599
Thr Pro Ile Gln Thr Ser Leu Ala Tyr Val Lys Thr Ser Glu Ser Leu
    760                 765                 770 aag cag aac aac cgt gat gcc atg gaa ctc aag ccc aac ggc ggt gct    2647
Lys Gln Asn Asn Arg Asp Ala Met Glu Leu Lys Pro Asn Gly Gly Ala
775                 780                 785                 790 gac caa aaa tgt ctc aaa gtc aac agc cca ata aga atg aag aat gga    2695
Asp Gln Lys Cys Leu Lys Val Asn Ser Pro Ile Arg Met Lys Asn Gly
                795                 800                 805 aat gga aaa ggg tgg ctg cga ctc aag aat aat atg gga gcc cat gag    2743
Asn Gly Lys Gly Trp Leu Arg Leu Lys Asn Asn Met Gly Ala His Glu
            810                 815                 820 gag aaa aag gaa gac tgg aat aat gtc act aaa gct gag tca atg ggg    2791
Glu Lys Lys Glu Asp Trp Asn Asn Val Thr Lys Ala Glu Ser Met Gly
        825                 830                 835 cta ttg tct gag gac ccc aag agc agt gat tca gag aac agt gtg acc    2839
Leu Leu Ser Glu Asp Pro Lys Ser Ser Asp Ser Glu Asn Ser Val Thr
    840                 845                 850 aaa aac cca cta agg aaa aca gat tct tgt gac agt gga att aca aaa    2887
Lys Asn Pro Leu Arg Lys Thr Asp Ser Cys Asp Ser Gly Ile Thr Lys
855                 860                 865                 870 agt gac ctt cgt ttg gat aag gct ggg gag gcc cga agt ccg cta gag    2935
Ser Asp Leu Arg Leu Asp Lys Ala Gly Glu Ala Arg Ser Pro Leu Glu
                875                 880                 885 cac agt ccc atc cag gct gat gcc aag cac ccc ttt tat ccc atc ccc    2983
His Ser Pro Ile Gln Ala Asp Ala Lys His Pro Phe Tyr Pro Ile Pro
            890                 895                 900 gag cag gcc tta cag acc aca ctg cag gaa gtc aaa cac gaa ctc aaa    3031
Glu Gln Ala Leu Gln Thr Thr Leu Gln Glu Val Lys His Glu Leu Lys
        905                 910                 915 gag gac atc cag ctg ctc agc tgc aga atg act gcc cta gaa aag cag    3079
Glu Asp Ile Gln Leu Leu Ser Cys Arg Met Thr Ala Leu Glu Lys Gln
```

-continued

| | | | | |
|---|---|---|---|---|
| Glu Asp Ile Gln Leu Leu Ser Cys Arg Met Thr Ala Leu Glu Lys Gln | | | | |
| 920 | 925 | 930 | | | gtg gca gaa att tta aaa ata ctg tcg gaa aaa agc gta ccc cag gcc   3127
Val Ala Glu Ile Leu Lys Ile Leu Ser Glu Lys Ser Val Pro Gln Ala
935                 940                 945                 950 tca tct ccc aaa tcc caa atg cca ctc caa gta ccc ccc cag ata cca   3175
Ser Ser Pro Lys Ser Gln Met Pro Leu Gln Val Pro Pro Gln Ile Pro
                955                 960                 965 tgt cag gat att ttt agt gtc tca agg cct gaa tca cct gaa tct gac   3223
Cys Gln Asp Ile Phe Ser Val Ser Arg Pro Glu Ser Pro Glu Ser Asp
            970                 975                 980 aaa gat gaa atc cac ttt taatatatat acatatatat ttgttaatat           3271
Lys Asp Glu Ile His Phe
            985 attaaaacag tatatacata tgtgtgtata tacagtatat acatatatat attttcactt  3331 gctttcaaga tgatgaccac acatggattt tgatatgtaa atattgcatg tccagctgga  3391 ttctggcctg ccaagaaga tgatgattaa aaacatagat attgcttgta tattatgcag   3451 ttgactgcat gcacacttta catttattta taatctctat tctataataa aagagtatga  3511 tttttgttaa aaaaaaaaaa aaaaaaaaaa ttcctcgccg ga                     3553

<210> SEQ ID NO 5
<211> LENGTH: 988
<212> TYPE: PRT
<213> ORGANISM: Homo sapiens

<400> SEQUENCE: 5

Met Pro Gly Gly Lys Arg Gly Leu Val Ala Pro Gln Asn Thr Phe Leu
1               5                   10                  15

Glu Asn Ile Val Arg Arg Ser Ser Glu Ser Ser Phe Leu Leu Gly Asn
                20                  25                  30

Ala Gln Ile Val Asp Trp Pro Val Val Tyr Ser Asn Asp Gly Phe Cys
            35                  40                  45

Lys Leu Ser Gly Tyr His Arg Ala Asp Val Met Gln Lys Ser Ser Thr
        50                  55                  60

Cys Ser Phe Met Tyr Gly Glu Leu Thr Asp Lys Lys Thr Ile Glu Lys
65              70                  75                  80

Val Arg Gln Thr Phe Asp Asn Tyr Glu Ser Asn Cys Phe Glu Val Leu
                85                  90                  95

Leu Tyr Lys Lys Asn Arg Thr Pro Val Trp Phe Tyr Met Gln Ile Ala
            100                 105                 110

Pro Ile Arg Asn Glu His Glu Lys Val Val Leu Phe Leu Cys Thr Phe
        115                 120                 125

Lys Asp Ile Thr Leu Phe Lys Gln Pro Ile Glu Asp Asp Ser Thr Lys
130                 135                 140

Gly Trp Thr Lys Phe Ala Arg Leu Thr Arg Ala Leu Thr Asn Ser Arg
145                 150                 155                 160

Ser Val Leu Gln Gln Leu Thr Pro Met Asn Lys Thr Glu Val Val His
                165                 170                 175

Lys His Ser Arg Leu Ala Glu Val Leu Gln Leu Gly Ser Asp Ile Leu
            180                 185                 190

Pro Gln Tyr Lys Gln Glu Ala Pro Lys Thr Pro Pro His Ile Ile Leu
        195                 200                 205

His Tyr Cys Ala Phe Lys Thr Thr Trp Asp Trp Val Ile Leu Ile Leu
    210                 215                 220

```
Thr Phe Tyr Thr Ala Ile Met Val Pro Tyr Asn Val Ser Phe Lys Thr
225                 230                 235                 240

Lys Gln Asn Asn Ile Ala Trp Leu Val Leu Asp Ser Val Val Asp Val
                245                 250                 255

Ile Phe Leu Val Asp Ile Val Leu Asn Phe His Thr Thr Phe Val Gly
                260                 265                 270

Pro Gly Gly Glu Val Ile Ser Asp Pro Lys Leu Ile Arg Met Asn Tyr
            275                 280                 285

Leu Lys Thr Trp Phe Val Ile Asp Leu Leu Ser Cys Leu Pro Tyr Asp
        290                 295                 300

Ile Ile Asn Ala Phe Glu Asn Val Asp Glu Gly Ile Ser Ser Leu Phe
305                 310                 315                 320

Ser Ser Leu Lys Val Val Arg Leu Leu Arg Leu Gly Arg Val Ala Arg
                325                 330                 335

Lys Leu Asp His Tyr Leu Glu Tyr Gly Ala Ala Val Leu Val Leu Leu
                340                 345                 350

Val Cys Val Phe Gly Leu Val Ala His Trp Leu Ala Cys Ile Trp Tyr
            355                 360                 365

Ser Ile Gly Asp Tyr Glu Val Ile Asp Glu Val Thr Asn Thr Ile Gln
370                 375                 380

Ile Asp Ser Trp Leu Tyr Gln Leu Ala Leu Ser Ile Gly Thr Pro Tyr
385                 390                 395                 400

Arg Tyr Asn Thr Ser Ala Gly Ile Trp Glu Gly Gly Pro Ser Lys Asp
                405                 410                 415

Ser Leu Tyr Val Ser Ser Leu Tyr Phe Thr Met Thr Ser Leu Thr Thr
                420                 425                 430

Ile Gly Phe Gly Asn Ile Ala Pro Thr Thr Asp Val Glu Lys Met Phe
            435                 440                 445

Ser Val Ala Met Met Met Val Gly Ser Leu Leu Tyr Ala Thr Ile Phe
450                 455                 460

Gly Asn Val Thr Thr Ile Phe Gln Gln Met Tyr Ala Asn Thr Asn Arg
465                 470                 475                 480

Tyr His Glu Met Leu Asn Asn Val Arg Asp Phe Leu Lys Leu Tyr Gln
                485                 490                 495

Val Pro Lys Gly Leu Ser Glu Arg Val Met Asp Tyr Ile Val Ser Thr
            500                 505                 510

Trp Ser Met Ser Lys Gly Ile Asp Thr Glu Lys Val Leu Ser Ile Cys
        515                 520                 525

Pro Lys Asp Met Arg Ala Asp Ile Cys Val His Leu Asn Arg Lys Val
530                 535                 540

Phe Asn Glu His Pro Ala Phe Arg Leu Ala Ser Asp Gly Cys Leu Arg
545                 550                 555                 560

Ala Leu Ala Val Glu Phe Gln Thr Ile His Cys Ala Pro Gly Asp Leu
                565                 570                 575

Ile Tyr His Ala Gly Glu Ser Val Asp Ala Leu Cys Phe Val Val Ser
            580                 585                 590

Gly Ser Leu Glu Val Ile Gln Asp Asp Glu Val Val Ala Ile Leu Gly
        595                 600                 605

Lys Gly Asp Val Phe Gly Asp Ile Phe Trp Lys Glu Thr Thr Leu Ala
        610                 615                 620

His Ala Cys Ala Asn Val Arg Ala Leu Thr Tyr Cys Asp Leu His Ile
625                 630                 635                 640

Ile Lys Arg Glu Ala Leu Leu Lys Val Leu Asp Phe Tyr Thr Ala Phe
```

```
                645              650              655
Ala Asn Ser Phe Ser Arg Asn Leu Thr Leu Thr Cys Asn Leu Arg Lys
            660              665              670
Arg Ile Ile Phe Arg Lys Ile Ser Asp Val Lys Lys Glu Glu Glu Glu
        675              680              685
Arg Leu Arg Gln Lys Asn Glu Val Thr Leu Ser Ile Pro Val Asp His
    690              695              700
Pro Val Arg Lys Leu Phe Gln Lys Phe Lys Gln Lys Glu Leu Arg
705              710              715              720
Asn Gln Gly Ser Thr Gln Gly Asp Pro Glu Arg Asn Gln Leu Gln Val
            725              730              735
Glu Ser Arg Ser Leu Gln Asn Gly Thr Ser Ile Thr Gly Thr Ser Val
        740              745              750
Val Thr Val Ser Gln Ile Thr Pro Ile Gln Thr Ser Leu Ala Tyr Val
    755              760              765
Lys Thr Ser Glu Ser Leu Lys Gln Asn Asn Arg Asp Ala Met Glu Leu
770              775              780
Lys Pro Asn Gly Gly Ala Asp Gln Lys Cys Leu Lys Val Asn Ser Pro
785              790              795              800
Ile Arg Met Lys Asn Gly Asn Gly Lys Gly Trp Leu Arg Leu Lys Asn
            805              810              815
Asn Met Gly Ala His Glu Lys Lys Glu Asp Trp Asn Asn Val Thr
        820              825              830
Lys Ala Glu Ser Met Gly Leu Leu Ser Glu Asp Pro Lys Ser Ser Asp
    835              840              845
Ser Glu Asn Ser Val Thr Lys Asn Pro Leu Arg Lys Thr Asp Ser Cys
850              855              860
Asp Ser Gly Ile Thr Lys Ser Asp Leu Arg Leu Asp Lys Ala Gly Glu
865              870              875              880
Ala Arg Ser Pro Leu Glu His Ser Pro Ile Gln Ala Asp Ala Lys His
            885              890              895
Pro Phe Tyr Pro Ile Pro Glu Gln Ala Leu Gln Thr Thr Leu Gln Glu
        900              905              910
Val Lys His Glu Leu Lys Glu Asp Ile Gln Leu Leu Ser Cys Arg Met
    915              920              925
Thr Ala Leu Glu Lys Gln Val Ala Glu Ile Leu Lys Ile Leu Ser Glu
930              935              940
Lys Ser Val Pro Gln Ala Ser Ser Pro Lys Ser Gln Met Pro Leu Gln
945              950              955              960
Val Pro Pro Gln Ile Pro Cys Gln Asp Ile Phe Ser Val Ser Arg Pro
            965              970              975
Glu Ser Pro Glu Ser Asp Lys Asp Glu Ile His Phe
        980              985

<210> SEQ ID NO 6
<211> LENGTH: 2967
<212> TYPE: DNA
<213> ORGANISM: Homo sapiens

<400> SEQUENCE: 6
atgccggggg gcaagagagg gctggtggca ccgcagaaca catttttgga gaacatcgtc      60
aggcgctcca gtgaatcaag tttcttactg ggaaatgccc agattgtgga ttggcctgta     120
gtttatagta atgacggttt ttgtaaactc tctggatatc atcgagctga cgtcatgcag     180
```

-continued

```
aaaagcagca cttgcagttt tatgtatggg gaattgactg acaagaagac cattgagaaa      240
gtcaggcaaa cttttgacaa ctacgaatca aactgctttg aagttcttct gtacaagaaa      300
aacagaaccc ctgtttggtt ttatatgcaa attgcaccaa taagaaatga acatgaaaag      360
gtggtcttgt tcctgtgtac tttcaaggat attacgttgt tcaaacagcc aatagaggat      420
gattcaacaa aaggttggac gaaatttgcc cgattgacac gggctttgac aaatagccga      480
agtgttttgc agcagctcac gccaatgaat aaaacagagg tggtccataa acattcaaga      540
ctagctgaag ttcttcagct gggatcagat atccttcctc agtataaaca agaagcgcca      600
aagacgccac cacacattat tttacattat tgtgctttta aaactacttg ggattgggtg      660
attttaattc ttaccttcta caccgccatt atggttcctt ataatgtttc cttcaaaaca      720
aagcagaaca acatagcctg gctggtactg gatagtgtgg tggacgttat ttttctggtt      780
gacatcgttt taaatttca cacgactttc gtggggcccg gtggagaggt catttctgac       840
cctaagctca taaggatgaa ctatctgaaa acttggtttg tgatcgatct gctgtcttgt      900
ttaccttatg acatcatcaa tgcctttgaa aatgtggatg agggaatcag cagtctcttc      960
agttctttaa aagtggtgcg tctcttacga ctgggccgtg tggctaggaa actgaccat      1020 tacctagaat atggagcagc agtcctcgtg ctcctggtgt gtgtgtttgg actggtggcc     1080
cactggctgg cctgcatatg gtatagcatc ggagactacg aggtcattga tgaagtcact     1140
aacaccatcc aaatagacag ttggctctac cagctggctt tgagcattgg gactccatat     1200
cgctacaata ccagtgctgg gatatgggaa ggaggaccca gcaaggattc attgtacgtg     1260
tcctctctct actttaccat gacaagcctt acaaccatag gatttggaaa catagctcct     1320
accacagatg tggagaagat gttttcggtg gctatgatga tggttggctc tcttctttat     1380
gcaactattt ttggaaatgt tacaacaatt ttccagcaaa tgtatgccaa caccaaccga     1440
tacgatgaga tgctgaataa tgtacgggac ttcctaaaac tctatcaggt cccaaaaggc     1500
cttagtgagc gagtcatgga ttatattgtc tcaacatggt ccatgtcaaa aggcattgat     1560
acagaaaagg tcctctccat ctgtcccaag gacatgagag ctgatatctg tgttcatcta     1620
aaccggaagg tttttaatga acatcctgct tttcgattgg ccagcgatgg gtgtctgcgc     1680
gccttggcgg tagagttcca aaccattcac tgtgctcccg gggacctcat ttaccatgct     1740
ggagaaagtg tggatgccct ctgctttgtg gtgtcaggat ccttggaagt catccaggat     1800
gatgaggtgg tggctatttt agggaagggt gatgtatttg gagacatctt ctggaaggaa     1860
accacccttg cccatgcatg tgcgaacgtc cgggcactga cgtactgtga cctacacatc     1920
atcaagcggg aagccttgct caaagtcctg gacttttata cagcttttgc aaactccttc     1980
tcaaggaatc tcactcttac ttgcaatctg aggaaacgga tcatctttcg taagatcagt     2040
gatgtgaaga aagaggagga ggagcgcctc cggcagaaga atgaggtgac cctcagcatt     2100
cccgtggacc acccagtcag aaagctcttc cagaagttca gcagcagaa ggagctgcgg      2160 aatcagggct caacacaggg tgaccctgag aggaaccaac tccaggtaga gagccgctcc     2220
ttacagaatg gaacctccat caccggaacc agcgtggtga ctgtgtcaca gattactccc     2280
attcagacgt ctctggccta tgtgaaaacc agtgaatccc ttaagcagaa caaccgtgat     2340 gccatgaac tcaagcccaa cggcggtgct gaccaaaaat gtctcaaagt caacagccca      2400
ataagaatga agaatggaaa tggaaaaggg tggctgcgac tcaagaataa tatgggagcc     2460
catgaggaga aaaggaaga ctggaataat gtcactaaag ctgagtcaat ggggctattg      2520
tctgaggacc ccaagagcag tgattcagag aacagtgtga ccaaaaaccc actaaggaaa     2580
```

-continued

```
acagattctt gtgacagtgg aattacaaaa agtgaccttc gtttggataa ggctggggag      2640
gcccgaagtc cgctagagca cagtcccatc caggctgatg ccaagcaccc cttttatccc      2700
atccccgagc aggccttaca gaccacactg caggaagtca acacgaact caaagaggac       2760 atccagctgc tcagctgcag aatgactgcc ctagaaaagc aggtggcaga aattttaaaa      2820
atactgtcgg aaaaaagcgt accccaggcc tcatctccca aatcccaaat gccactccaa      2880
gtaccccccc agataccatg tcaggatatt tttagtgtct caaggcctga atcacctgaa      2940
tctgacaaag atgaaatcca cttttaa                                         2967
```

<210> SEQ ID NO 7
<211> LENGTH: 1341
<212> TYPE: DNA
<213> ORGANISM: Homo sapiens
<220> FEATURE:
<221> NAME/KEY: CDS
<222> LOCATION: (1)...(1338)

<400> SEQUENCE: 7

```
tgc tgc gag cgg ctg gtg ctc aac gtg gcc ggg ctg cgc ttc gag acg       48
Cys Cys Glu Arg Leu Val Leu Asn Val Ala Gly Leu Arg Phe Glu Thr
 1               5                  10                  15 cgg gcg cgc acg ctg ggc cgc ttc ccg gac act ctg cta ggg gac cca       96
Arg Ala Arg Thr Leu Gly Arg Phe Pro Asp Thr Leu Leu Gly Asp Pro
             20                  25                  30 gcg cgc cgc ggc cgc ttc tac gac gac gcg cgc cgc gag tat ttc ttc      144
Ala Arg Arg Gly Arg Phe Tyr Asp Asp Ala Arg Arg Glu Tyr Phe Phe
         35                  40                  45 gac cgg cac cgg ccc agc ttc gac gcc gtg ctc tac tac tac cag tcc      192
Asp Arg His Arg Pro Ser Phe Asp Ala Val Leu Tyr Tyr Tyr Gln Ser
     50                  55                  60 ggt ggg cgg ctg cgg cgg ccg gcg cac gtg ccg ctc gac gtc ttc ctg      240
Gly Gly Arg Leu Arg Arg Pro Ala His Val Pro Leu Asp Val Phe Leu
 65                  70                  75                  80 gaa gag gtg gcc ttc tac ggg ctg ggc gcg gcg gcc ctg gca cgc ctg      288
Glu Glu Val Ala Phe Tyr Gly Leu Gly Ala Ala Ala Leu Ala Arg Leu
                 85                  90                  95 cgc gag gac gag ggc tgc ccg gtg ccg ccc gag cgc ccc ctg ccc cgc      336
Arg Glu Asp Glu Gly Cys Pro Val Pro Pro Glu Arg Pro Leu Pro Arg
            100                 105                 110 cgc gcc ttc gcc cgc cag ctg tgc ctg ctt ttc gag ttt ccc gag agc      384
Arg Ala Phe Ala Arg Gln Leu Cys Leu Leu Phe Glu Phe Pro Glu Ser
        115                 120                 125 tct cag gcc gcg cgc gtg ctc gcc gta gtc tcc gtg ctg gtc atc ctc      432
Ser Gln Ala Ala Arg Val Leu Ala Val Val Ser Val Leu Val Ile Leu
    130                 135                 140 gtc tcc atc gtc gtc ttc tgc ctc gag acg ctg cct gac ttc cgc gac      480
Val Ser Ile Val Val Phe Cys Leu Glu Thr Leu Pro Asp Phe Arg Asp
145                 150                 155                 160 gac cgc gac ggc acg ggg ctt gct gct gca gcc gca gcc ggg ccg ttc      528
Asp Arg Asp Gly Thr Gly Leu Ala Ala Ala Ala Ala Ala Gly Pro Phe
                165                 170                 175 ccc gct ccg ctg aat ggc tcc agc caa atg cct gga aat cca ccc cgc      576
Pro Ala Pro Leu Asn Gly Ser Ser Gln Met Pro Gly Asn Pro Pro Arg
            180                 185                 190 ctg ccc ttc aat gac ccg ttc ttc gtg gtg gag acg ctg tgt att tgt      624
Leu Pro Phe Asn Asp Pro Phe Phe Val Val Glu Thr Leu Cys Ile Cys
        195                 200                 205 tgg ttc tcc ttt gag ctg ctg gta cgc ctc ctg gtc tgt cca agc aag      672
Trp Phe Ser Phe Glu Leu Leu Val Arg Leu Leu Val Cys Pro Ser Lys
```

-continued

```
Trp Phe Ser Phe Glu Leu Leu Val Arg Leu Leu Val Cys Pro Ser Lys
    210                 215                 220 gct atc ttc ttc aag aac gtg atg aac ctc atc gat ttt gtg gct atc        720
Ala Ile Phe Phe Lys Asn Val Met Asn Leu Ile Asp Phe Val Ala Ile
225                 230                 235                 240 ctt ccc tac ttt gtg gca ctg ggc acc gag ctg gcc cgg cag cga ggg        768
Leu Pro Tyr Phe Val Ala Leu Gly Thr Glu Leu Ala Arg Gln Arg Gly
                245                 250                 255 gtg ggc cag cag gcc atg tca ctg gcc atc ctg aga gtc atc cga ttg        816
Val Gly Gln Gln Ala Met Ser Leu Ala Ile Leu Arg Val Ile Arg Leu
            260                 265                 270 gtg cgt gtc ttc cgc atc ttc aag ctg tcc cgg cac tca aag ggc ctg        864
Val Arg Val Phe Arg Ile Phe Lys Leu Ser Arg His Ser Lys Gly Leu
        275                 280                 285 caa atc ttg ggc cag acg ctt cgg gcc tcc atg cgt gag ctg ggc ctc        912
Gln Ile Leu Gly Gln Thr Leu Arg Ala Ser Met Arg Glu Leu Gly Leu
    290                 295                 300 ctc atc ttt ttc ctc ttc atc ggt gtg gtc ctc ttt tcc agc gcc gtc        960
Leu Ile Phe Phe Leu Phe Ile Gly Val Val Leu Phe Ser Ser Ala Val
305                 310                 315                 320 tac ttt gcc gaa gtt gac cgg gtg gac tcc cat ttc act agc atc cct       1008
Tyr Phe Ala Glu Val Asp Arg Val Asp Ser His Phe Thr Ser Ile Pro
                325                 330                 335 gag tcc ttc tgg tgg gcg gta gtc acc atg act aca gtt ggc tat gga       1056
Glu Ser Phe Trp Trp Ala Val Val Thr Met Thr Thr Val Gly Tyr Gly
            340                 345                 350 gac atg gca ccc gtc act gtg ggt ggc aag ata gtg ggc tct ctg tgt       1104
Asp Met Ala Pro Val Thr Val Gly Gly Lys Ile Val Gly Ser Leu Cys
        355                 360                 365 gcc att gcg ggc gtg ctg act att tcc ctg cca gtg ccc gtc att gtc       1152
Ala Ile Ala Gly Val Leu Thr Ile Ser Leu Pro Val Pro Val Ile Val
    370                 375                 380 tcc aat ttc agc tac ttt tat cac cgg gag aca gag ggc gaa gag gct       1200
Ser Asn Phe Ser Tyr Phe Tyr His Arg Glu Thr Glu Gly Glu Glu Ala
385                 390                 395                 400 ggg atg ttc agc cat gtg gac atg cag cct tgt ggc cca ctg gag ggc       1248
Gly Met Phe Ser His Val Asp Met Gln Pro Cys Gly Pro Leu Glu Gly
                405                 410                 415 aag gcc aat ggg ggc ctg gtg gac ggg gag gta cct gag cta cca cct       1296
Lys Ala Asn Gly Gly Leu Val Asp Gly Glu Val Pro Glu Leu Pro Pro
            420                 425                 430 cca ctc tgg gca ccc cca ggg aaa cac ctg gtc acc gaa gtg                1338
Pro Leu Trp Ala Pro Pro Gly Lys His Leu Val Thr Glu Val
        435                 440                 445 tga                                                                    1341
```

<210> SEQ ID NO 8
<211> LENGTH: 446
<212> TYPE: PRT
<213> ORGANISM: Homo sapiens

<400> SEQUENCE: 8

```
Cys Cys Glu Arg Leu Val Leu Asn Val Ala Gly Leu Arg Phe Glu Thr
1               5                   10                  15

Arg Ala Arg Thr Leu Gly Arg Phe Pro Asp Thr Leu Leu Gly Asp Pro
            20                  25                  30

Ala Arg Arg Gly Arg Phe Tyr Asp Asp Ala Arg Arg Glu Tyr Phe Phe
        35                  40                  45

Asp Arg His Arg Pro Ser Phe Asp Ala Val Leu Tyr Tyr Tyr Gln Ser
```

```
                    50                  55                  60
Gly Gly Arg Leu Arg Arg Pro Ala His Val Pro Leu Asp Val Phe Leu
 65                  70                  75                  80

Glu Glu Val Ala Phe Tyr Gly Leu Gly Ala Ala Leu Ala Arg Leu
                 85                  90                  95

Arg Glu Asp Glu Gly Cys Pro Val Pro Pro Glu Arg Pro Leu Pro Arg
                100                 105                 110

Arg Ala Phe Ala Arg Gln Leu Cys Leu Leu Phe Glu Phe Pro Glu Ser
                115                 120                 125

Ser Gln Ala Ala Arg Val Leu Ala Val Val Ser Val Leu Val Ile Leu
                130                 135                 140

Val Ser Ile Val Val Phe Cys Leu Glu Thr Leu Pro Asp Phe Arg Asp
145                 150                 155                 160

Asp Arg Asp Gly Thr Gly Leu Ala Ala Ala Ala Ala Gly Pro Phe
                165                 170                 175

Pro Ala Pro Leu Asn Gly Ser Ser Gln Met Pro Gly Asn Pro Pro Arg
                180                 185                 190

Leu Pro Phe Asn Asp Pro Phe Phe Val Val Glu Thr Leu Cys Ile Cys
                195                 200                 205

Trp Phe Ser Phe Glu Leu Leu Val Arg Leu Leu Val Cys Pro Ser Lys
                210                 215                 220

Ala Ile Phe Phe Lys Asn Val Met Asn Leu Ile Asp Phe Val Ala Ile
225                 230                 235                 240

Leu Pro Tyr Phe Val Ala Leu Gly Thr Glu Leu Ala Arg Gln Arg Gly
                245                 250                 255

Val Gly Gln Gln Ala Met Ser Leu Ala Ile Leu Arg Val Ile Arg Leu
                260                 265                 270

Val Arg Val Phe Arg Ile Phe Lys Leu Ser Arg His Ser Lys Gly Leu
                275                 280                 285

Gln Ile Leu Gly Gln Thr Leu Arg Ala Ser Met Arg Glu Leu Gly Leu
                290                 295                 300

Leu Ile Phe Phe Leu Phe Ile Gly Val Val Leu Phe Ser Ser Ala Val
305                 310                 315                 320

Tyr Phe Ala Glu Val Asp Arg Val Asp Ser His Phe Thr Ser Ile Pro
                325                 330                 335

Glu Ser Phe Trp Trp Ala Val Val Thr Met Thr Thr Val Gly Tyr Gly
                340                 345                 350

Asp Met Ala Pro Val Thr Val Gly Gly Lys Ile Val Gly Ser Leu Cys
                355                 360                 365

Ala Ile Ala Gly Val Leu Thr Ile Ser Leu Pro Val Pro Val Ile Val
                370                 375                 380

Ser Asn Phe Ser Tyr Phe Tyr His Arg Glu Thr Glu Gly Glu Glu Ala
385                 390                 395                 400

Gly Met Phe Ser His Val Asp Met Gln Pro Cys Gly Pro Leu Glu Gly
                405                 410                 415

Lys Ala Asn Gly Gly Leu Val Asp Gly Glu Val Pro Glu Leu Pro Pro
                420                 425                 430

Pro Leu Trp Ala Pro Pro Gly Lys His Leu Val Thr Glu Val
                435                 440                 445

<210> SEQ ID NO 9
<211> LENGTH: 223
<212> TYPE: PRT
<213> ORGANISM: Artificial Sequence
```

```
<220> FEATURE:
<223> OTHER INFORMATION: consensus sequence

<400> SEQUENCE: 9

Ile Leu Phe Ile Leu Asp Leu Leu Phe Val Leu Leu Phe Leu Leu Glu
 1               5                  10                  15

Ile Val Leu Lys Phe Ile Ala Tyr Gly Leu Lys Ser Thr Ser Asn Ile
            20                  25                  30

Ala Ala Lys Tyr Leu Lys Ser Ile Phe Asn Ile Leu Asp Leu Leu Ala
        35                  40                  45

Ile Leu Pro Leu Leu Leu Leu Val Leu Phe Leu Ser Gly Thr Glu
    50                  55                  60

Gln Val Ala Lys Lys Arg Leu Arg Glu Arg Phe Ser Leu Glu Leu Ser
65                  70                  75                  80

Gln Trp Tyr Tyr Arg Ile Leu Arg Phe Leu Arg Leu Arg Leu Leu
                85                  90                  95

Arg Leu Leu Arg Leu Leu Arg Leu Leu Arg Arg Leu Glu Thr Leu Phe
                100                 105                 110

Glu Phe Glu Leu Gly Thr Leu Ala Trp Ser Leu Gln Ser Leu Gly Arg
            115                 120                 125

Ala Leu Lys Ser Ile Leu Arg Phe Leu Leu Leu Leu Leu Leu Leu
    130                 135                 140

Ile Gly Phe Ser Val Ile Gly Tyr Leu Leu Phe Lys Gly Tyr Glu Asp
145                 150                 155                 160

Leu Ser Glu Asn Glu Val Asp Gly Asn Ser Glu Phe Ser Ser Tyr Phe
                165                 170                 175

Asp Ala Phe Tyr Phe Leu Phe Val Thr Leu Thr Thr Val Gly Phe Gly
            180                 185                 190

Asp Leu Val Pro Val Trp Leu Gly Ile Ile Phe Phe Val Leu Phe Phe
            195                 200                 205

Ile Ile Val Gly Leu Leu Leu Asn Leu Leu Ile Ala Val Ile
        210                 215                 220

<210> SEQ ID NO 10
<211> LENGTH: 120
<212> TYPE: PRT
<213> ORGANISM: Artificial Sequence
<220> FEATURE:
<223> OTHER INFORMATION: consensus sequence

<400> SEQUENCE: 10

Ala Leu Glu Glu Arg Ser Tyr Pro Ala Gly Glu Val Ile Ile Arg Gln
 1               5                  10                  15

Gly Asp Pro Gly Asp Ser Phe Tyr Ile Val Leu Ser Gly Glu Val Glu
            20                  25                  30

Val Tyr Lys Leu Thr Glu Asp Gly Ala Arg Thr Pro Glu Val Ser Gln
        35                  40                  45

Lys Gln Asp Thr Arg Glu Gln Val Val Ala Thr Leu Gly Pro Gly Asp
    50                  55                  60

Phe Phe Gly Glu Leu Ala Leu Leu Thr Asn Asp Gly Asn Lys Asn Ala
65                  70                  75                  80

Val Leu Pro Ser Leu Asp Gln Gly Ala Pro Arg Thr Ala Thr Val Arg
                85                  90                  95

Ala Leu Thr Asp Ser Glu Leu Leu Arg Leu Asp Arg Glu Asp Phe Arg
                100                 105                 110

Arg Leu Leu Gln Lys Tyr Pro Glu
```

<210> SEQ ID NO 11
<211> LENGTH: 111
<212> TYPE: PRT
<213> ORGANISM: Artificial Sequence
<220> FEATURE:
<223> OTHER INFORMATION: consensus sequence

<400> SEQUENCE: 11

```
Glu Arg Val Arg Leu Asn Val Gly Gly Lys Arg Phe Glu Thr Ser Lys
1               5                  10                  15

Ser Thr Leu Thr Arg Phe Lys Pro Asp Thr Leu Leu Gly Arg Leu Leu
            20                  25                  30

Lys Thr Asp Ser Asp Val His Glu Ala Arg Leu Arg Leu Cys Asp Phe
        35                  40                  45

Tyr Asp Asp Glu Thr Gly Glu Tyr Phe Phe Asp Arg Ser Pro Lys His
    50                  55                  60

Phe Glu Thr Ile Leu Asn Phe Tyr Arg Thr Gly Asp Gly Lys Leu His
65                  70                  75                  80

Arg Pro Glu Val Cys Leu Asp Ser Phe Leu Glu Glu Leu Glu Phe Tyr
                85                  90                  95

Gly Leu Asp Glu Leu Ala Ile Glu Ser Cys Cys Glu Asp Glu Tyr
            100                 105                 110
```

<210> SEQ ID NO 12
<211> LENGTH: 988
<212> TYPE: PRT
<213> ORGANISM: Rattus norvegicus

<400> SEQUENCE: 12

```
Met Pro Gly Gly Lys Arg Gly Leu Val Ala Pro Gln Asn Thr Phe Leu
1               5                  10                  15

Glu Asn Ile Val Arg Arg Ser Ser Glu Ser Ser Phe Leu Leu Gly Asn
            20                  25                  30

Ala Gln Ile Val Asp Trp Pro Val Val Tyr Ser Asn Asp Gly Phe Cys
        35                  40                  45

Lys Leu Ser Gly Tyr His Arg Ala Asp Val Met Gln Lys Ser Ser Thr
    50                  55                  60

Cys Ser Phe Met Tyr Gly Glu Leu Thr Asp Lys Lys Thr Ile Glu Lys
65                  70                  75                  80

Val Arg Gln Thr Phe Asp Asn Tyr Glu Ser Asn Cys Phe Glu Val Leu
                85                  90                  95

Leu Tyr Lys Lys Asn Arg Thr Pro Val Trp Phe Tyr Met Gln Ile Ala
                100                 105                 110

Pro Ile Arg Asn Glu His Glu Lys Val Val Leu Phe Leu Cys Thr Phe
            115                 120                 125

Lys Asp Ile Thr Leu Phe Lys Gln Pro Ile Glu Asp Asp Ser Thr Lys
        130                 135                 140

Gly Trp Thr Lys Phe Ala Arg Leu Thr Arg Ala Leu Thr Asn Ser Arg
145                 150                 155                 160

Ser Val Leu Gln Gln Leu Thr Pro Met Asn Lys Thr Glu Thr Val His
                165                 170                 175

Lys His Ser Arg Leu Ala Glu Val Leu Gln Leu Gly Ser Asp Ile Leu
            180                 185                 190

Pro Gln Tyr Lys Gln Glu Ala Pro Lys Thr Pro Pro His Ile Ile Leu
        195                 200                 205
```

```
His Tyr Cys Ala Phe Lys Thr Thr Trp Asp Trp Val Ile Leu Ile Leu
    210                 215                 220
Thr Phe Tyr Thr Ala Ile Met Val Pro Tyr Asn Val Ser Phe Lys Thr
225                 230                 235                 240
Lys Gln Asn Asn Ile Ala Trp Leu Val Leu Asp Ser Val Val Asp Val
                245                 250                 255
Ile Phe Leu Val Asp Ile Val Leu Asn Phe His Thr Thr Phe Val Gly
            260                 265                 270
Pro Gly Gly Glu Val Ile Ser Asp Pro Lys Leu Ile Arg Met Asn Tyr
        275                 280                 285
Leu Lys Thr Trp Phe Val Ile Asp Leu Leu Ser Cys Leu Pro Tyr Asp
    290                 295                 300
Ile Ile Asn Ala Phe Glu Asn Val Asp Glu Gly Ile Ser Ser Leu Phe
305                 310                 315                 320
Ser Ser Leu Lys Val Val Arg Leu Leu Arg Leu Gly Arg Val Ala Arg
                325                 330                 335
Lys Leu Asp His Tyr Leu Glu Tyr Gly Ala Ala Val Leu Val Leu Leu
            340                 345                 350
Val Cys Val Phe Gly Leu Val Ala His Trp Leu Ala Cys Ile Trp Tyr
        355                 360                 365
Ser Ile Gly Asp Tyr Glu Val Ile Asp Glu Val Thr Asn Thr Ile Gln
    370                 375                 380
Ile Asp Ser Trp Leu Tyr Gln Leu Ala Leu Ser Ile Arg Thr Pro Tyr
385                 390                 395                 400
Arg Tyr Asn Thr Ser Ala Gly Ile Trp Glu Gly Gly Pro Ser Lys Asp
                405                 410                 415
Ser Leu Tyr Val Ser Ser Leu Tyr Phe Thr Met Thr Ser Leu Thr Thr
            420                 425                 430
Ile Gly Phe Gly Asn Ile Ala Pro Thr Thr Asp Val Glu Lys Met Phe
        435                 440                 445
Ser Val Ala Met Met Met Val Gly Ser Leu Leu Tyr Ala Thr Ile Phe
450                 455                 460
Gly Asn Val Thr Thr Ile Phe Gln Gln Met Tyr Ala Asn Thr Asn Arg
465                 470                 475                 480
Tyr His Glu Met Leu Asn Asn Val Arg Asp Phe Leu Lys Leu Tyr Gln
                485                 490                 495
Val Pro Lys Gly Leu Ser Glu Arg Val Met Asp Tyr Ile Val Ser Thr
            500                 505                 510
Trp Ser Met Ser Lys Gly Ile Asp Thr Glu Lys Val Leu Ser Ile Cys
        515                 520                 525
Pro Lys Asp Met Arg Ala Asp Ile Cys Val His Leu Asn Arg Lys Val
    530                 535                 540
Phe Asn Glu His Pro Ala Phe Arg Leu Ala Ser Asp Gly Cys Leu Arg
545                 550                 555                 560
Ala Leu Ala Val Glu Phe Gln Thr Ile His Cys Ala Pro Gly Asp Leu
                565                 570                 575
Ile Tyr His Ala Gly Glu Ser Val Asp Ala Leu Cys Phe Val Val Ser
            580                 585                 590
Gly Ser Leu Glu Val Ile Gln Asp Glu Val Val Ala Ile Leu Gly
        595                 600                 605
Lys Gly Asp Val Phe Gly Asp Ile Phe Trp Lys Glu Thr Thr Leu Ala
    610                 615                 620
```

His Ala Cys Ala Asn Val Arg Ala Leu Thr Tyr Cys Asp Leu His Ile
625                 630                 635                 640

Ile Lys Arg Glu Ala Leu Leu Lys Val Leu Asp Phe Tyr Thr Ala Phe
            645                 650                 655

Ala Asn Ser Phe Ser Arg Asn Leu Thr Leu Thr Cys Asn Leu Arg Lys
            660                 665                 670

Arg Ile Ile Phe Arg Lys Ile Ser Asp Val Lys Lys Glu Glu Glu Glu
        675                 680                 685

Arg Leu Arg Gln Lys Asn Glu Val Thr Leu Ser Ile Pro Val Asp His
690                 695                 700

Pro Val Arg Lys Leu Phe Gln Lys Phe Lys Gln Lys Glu Leu Arg
705                 710                 715                 720

Asn Gln Gly Ser Ala Gln Ser Asp Pro Glu Arg Ser Gln Leu Gln Val
                725                 730                 735

Glu Ser Arg Pro Leu Gln Asn Gly Ala Ser Ile Thr Gly Thr Ser Val
                740                 745                 750

Val Thr Val Ser Gln Ile Thr Pro Ile Gln Thr Ser Leu Ala Tyr Val
            755                 760                 765

Lys Thr Ser Glu Thr Leu Lys Gln Asn Asn Arg Asp Ala Met Glu Leu
    770                 775                 780

Lys Pro Asn Gly Gly Ala Glu Pro Lys Cys Leu Lys Val Asn Ser Pro
785                 790                 795                 800

Ile Arg Met Lys Asn Gly Asn Gly Lys Gly Trp Leu Arg Leu Lys Asn
                805                 810                 815

Asn Met Gly Ala His Glu Glu Lys Lys Glu Glu Trp Asn Asn Val Thr
                820                 825                 830

Lys Ala Glu Ser Met Gly Leu Leu Ser Glu Asp Pro Lys Gly Ser Asp
    835                 840                 845

Ser Glu Asn Ser Val Thr Lys Asn Pro Leu Arg Lys Thr Asp Ser Cys
850                 855                 860

Asp Ser Gly Ile Thr Lys Ser Asp Leu Arg Leu Asp Lys Ala Gly Glu
865                 870                 875                 880

Ala Arg Ser Pro Leu Glu His Ser Pro Ser Gln Ala Asp Ala Lys His
                885                 890                 895

Pro Phe Tyr Pro Ile Pro Glu Gln Ala Leu Gln Thr Thr Leu Gln Glu
                900                 905                 910

Val Lys His Glu Leu Lys Glu Asp Ile Gln Leu Leu Ser Cys Arg Met
    915                 920                 925

Thr Ala Leu Glu Lys Gln Val Ala Glu Ile Leu Lys Leu Leu Ser Glu
    930                 935                 940

Lys Ser Val Pro Gln Thr Ser Pro Lys Pro Gln Ile Pro Leu Gln
945                 950                 955                 960

Val Pro Pro Gln Ile Pro Cys Gln Asp Ile Phe Ser Val Ser Arg Pro
                965                 970                 975

Glu Ser Pro Glu Ser Asp Lys Asp Glu Ile Asn Phe
                980                 985

<210> SEQ ID NO 13
<211> LENGTH: 532
<212> TYPE: PRT
<213> ORGANISM: Mus musculus

<400> SEQUENCE: 13

Met Thr Thr Arg Lys Ala Gln Glu Ile His Gly Lys Ala Pro Gly Gly
1               5                   10                  15

-continued

```
Ser Val Ser Thr Gly Val Gly Thr Ala Glu Gly Ala Pro Ser Pro Ala
             20                  25                  30
Gly Val Thr Pro Pro Pro Pro Arg Pro Gly Arg Thr Phe His Ala
         35                  40                  45
Ile Phe Thr Arg Arg His Arg Thr Pro Asp Trp Gly Gly Cys Gly Val
     50                  55                  60
Gly Ala Thr Arg Pro Phe Thr Gly Arg Pro Gly Cys Ala Arg His Gly
 65                  70                  75                  80
Ala Thr Val Pro Ala Ala Leu Arg Cys Cys Glu Arg Leu Val Leu Asn
                 85                  90                  95
Val Ala Gly Leu Arg Phe Glu Thr Arg Ala Arg Thr Leu Gly Arg Phe
            100                 105                 110
Pro Asp Thr Leu Leu Gly Asp Pro Val Arg Arg Ser Arg Phe Tyr Asp
            115                 120                 125
Gly Ala Arg Ala Glu Tyr Phe Phe Asp Arg His Arg Pro Ser Phe Asp
130                 135                 140
Ala Val Leu Tyr Tyr Tyr Gln Ser Gly Gly Arg Leu Arg Arg Pro Ala
145                 150                 155                 160
His Val Pro Leu Asp Val Phe Leu Glu Glu Val Ser Phe Tyr Gly Leu
                165                 170                 175
Gly Arg Arg Leu Ala Arg Leu Arg Glu Asp Glu Gly Cys Ala Val Ala
            180                 185                 190
Glu Arg Pro Leu Pro Pro Phe Ala Arg Gln Leu Trp Leu Leu Phe
        195                 200                 205
Glu Phe Pro Glu Ser Ser Gln Ala Ala Arg Val Leu Ala Val Val Ser
    210                 215                 220
Val Leu Val Ile Leu Val Ser Ile Val Val Phe Cys Leu Glu Thr Leu
225                 230                 235                 240
Pro Asp Phe Arg Asp Asp Arg Asp Asp Pro Gly Leu Ala Pro Val Ala
                245                 250                 255
Ala Ala Thr Gly Ser Phe Leu Ala Arg Leu Asn Gly Ser Ser Pro Met
            260                 265                 270
Pro Gly Ala Pro Pro Arg Gln Pro Phe Asn Asp Pro Phe Phe Val Val
        275                 280                 285
Glu Thr Leu Cys Ile Cys Trp Phe Ser Phe Glu Leu Leu Val His Leu
    290                 295                 300
Val Ala Cys Pro Ser Lys Ala Val Phe Phe Lys Asn Val Met Asn Leu
305                 310                 315                 320
Ile Asp Phe Val Ala Ile Leu Pro Tyr Phe Val Ala Leu Gly Thr Glu
                325                 330                 335
Leu Ala Arg Gln Arg Gly Val Gly Gln Pro Ala Met Ser Leu Ala Ile
            340                 345                 350
Leu Arg Val Ile Arg Leu Val Arg Val Phe Arg Ile Phe Lys Leu Ser
        355                 360                 365
Arg His Ser Lys Gly Leu Gln Ile Leu Gly Gln Thr Leu Arg Ala Ser
    370                 375                 380
Met Arg Glu Leu Gly Leu Leu Ile Phe Phe Leu Phe Ile Gly Val Val
385                 390                 395                 400
Leu Phe Ser Ser Ala Val Tyr Phe Ala Glu Val Asp Arg Val Asp Thr
                405                 410                 415
His Phe Thr Ser Ile Pro Glu Ser Phe Trp Trp Ala Val Val Thr Met
            420                 425                 430
```

-continued

```
Thr Thr Val Gly Tyr Gly Asp Met Ala Pro Val Thr Val Gly Gly Lys
        435                 440                 445

Ile Val Gly Ser Leu Cys Ala Ile Ala Gly Val Leu Thr Ile Ser Leu
    450                 455                 460

Pro Val Pro Val Ile Val Ser Asn Phe Ser Tyr Phe Tyr His Arg Glu
465                 470                 475                 480

Thr Glu Gly Glu Glu Ala Gly Met Tyr Ser His Val Asp Thr Gln Pro
                485                 490                 495

Cys Gly Thr Leu Glu Gly Lys Ala Asn Gly Gly Leu Val Asp Ser Glu
                500                 505                 510

Val Pro Glu Leu Leu Pro Pro Leu Trp Pro Pro Ala Gly Lys His Met
        515                 520                 525

Val Thr Glu Val
        530
```

52906 POTASSIUM CHANNEL NUCLEIC ACIDS AND USES THEREFOR

RELATED APPLICATIONS

This application claims priority to U.S. provisional application No. 60/209,845 filed on Jun. 6, 2000, now ABANDONED, the contents of which are incorporated herein by reference.

BACKGROUND OF THE INVENTION

Potassium ($K^+$) channels are ubiquitous proteins which are involved in the setting of the resting membrane potential as well as in the modulation of the electrical activity of cells. In excitable cells, $K^+$ channels influence action potential waveforms, firing frequency, and neurotransmitter secretion (Rudy, B. (1988) *Neuroscience*, 25, 729–749; Hille, B. (1992) *Ionic Channels of Excitable Membranes*, 2nd Ed.). In non-excitable cells, they are involved in hormone secretion, cell volume regulation and potentially in cell proliferation and differentiation (Lewis et al. (1995) *Annu. Rev. Immunol.*, 13, 623–653). Developments in electrophysiology have allowed the identification and the characterization of an astonishing variety of $K^+$ channels that differ in their biophysical properties, pharmacology, regulation and tissue distribution (Rudy, B. (1988) *Neuroscience*, 25, 729–749; Hille, B. (1992) *Ionic Channels of Excitable Membranes*, 2nd Ed.). More recently, cloning efforts have shed considerable light on the mechanisms that determine this functional diversity. Furthermore, analyses of structure-function relationships have provided an important set of data concerning the molecular basis of the biophysical properties (selectivity, gating, assembly) and the pharmacological properties of cloned $K^+$ channels.

Functional diversity of $K^+$ channels arises mainly from the existence of a great number of genes coding for pore-forming subunits, as well as for other associated regulatory subunits. Two main structural families of pore-forming subunits have been identified. The first one consists of subunits with a conserved hydrophobic core containing six transmembrane domains (TMDs). These $K^+$ channel α subunits participate in the formation of outward rectifier voltage-gated (Kv) and $Ca^{2+}$-dependent $K^+$ channels. The fourth TMD contains repeated positive charges involved in the voltage gating of these channels and hence in their outward rectification (Logothetis et al. (1992) *Neuron*, 8, 531–540; Bezanilla et al. (1994) *Biophys. J.* 66, 1011–1021).

The second family of pore-forming subunits have only two TMDs. They are essential subunits of inward-rectifying (IRK), G-protein-coupled (GIRK) and ATP-sensitive ($K_{ATP}$) $K^+$ channels. The inward rectification results from a voltage-dependent block by cytoplasmic $Mg^{2+}$ and polyamines (Matsuda, H. (1991) *Annu. Rev. Physiol.*, 53, 289–298). A conserved domain, called the P domain, is present in all members of both families (Pongs, O. (1993) *J. Membr. Biol.*, 136, 1–8; Heginbotham et al. (1994) *Biophys. J.* 66, 1061–1067; Mackinnon, R. (1995) *Neuron*, 14, 889–892; Pascual et al., (1995) *Neuron.*, and 14, 1055–1063). This domain is an essential element of the aqueous $K^+$-selective pore. In both groups, the assembly of four subunits is necessary to form a functional $K^+$ channel (Mackinnon, R. (1991) *Nature*, 350, 232–235; Yang et al., (1995) *Neuron*, 15, 1441–1447.

In both six TMD and two TMD pore-forming subunit families, different subunits coded by different genes can associate to form heterotetramers with new channel properties (Isacoff et al., (1990) *Nature*, 345, 530–534). A selective formation of heteropolymeric channels may allow each cell to develop the best $K^+$ current repertoire suited to its function. Pore-forming α subunits of Kv channels are classified into different subfamilies according to their sequence similarity (Chandy et al. (1993) *Trends Pharmacol. Sci.*, 14, 434). Tetramerization is believed to occur preferentially between members of each subgroup (Covarrubias et al. (1991) *Neuron*, 7, 763–773). The domain responsible for this selective association is localized in the N-terminal region and is conserved between members of the same subgroup. This domain is necessary for hetero- but not homomultimeric assembly within a subfamily and prevents co-assembly between subfamilies. Recently, pore-forming subunits with two TMDs were also shown to co-assemble to form heteropolymers (Duprat et al. (1995) *Biochem. Biophys. Res. Commun.*, 212, 657–663. This heteropolymerization seems necessary to give functional GIRKs. IRKs are active as homopolymers but also form heteropolymers.

SUMMARY OF THE INVENTION

The present invention is based, in part, on the discovery of novel potassium channel family members, referred to herein as "52906," "33408," and "12189." The nucleotide sequence of a cDNA encoding 52906 is shown in SEQ ID NO:1, and the amino acid sequence of a 52906 polypeptide is shown in SEQ ID NO:2. In addition, the nucleotide sequences of the coding region are depicted in SEQ ID NO:3. The nucleotide sequence of a cDNA encoding 33408 is shown in SEQ ID NO:4, and the amino acid sequence of a 33408 polypeptide is shown in SEQ ID NO:5. In addition, the nucleotide sequences of the coding region are depicted in SEQ ID NO:6. The nucleotide sequence of a cDNA encoding 12189 is shown in SEQ ID NO:7, and the amino acid sequence of a 12189 polypeptide is shown in SEQ ID NO:8. In addition, the nucleotide sequences of the coding region are depicted in SEQ ID NO:7.

Accordingly, in one aspect, the invention features a nucleic acid molecule that encodes a 52906, 33408, or 12189 protein or polypeptide, e.g., a biologically active portion of the 52906, 33408, or 12189 protein. In a preferred embodiment the isolated nucleic acid molecule encodes a polypeptide having the amino acid sequence of SEQ ID NO:2, SEQ ID NO:5, or SEQ ID NO:8. In other embodiments, the invention provides isolated 52906, 33408, or 12189 nucleic acid molecules having the nucleotide sequence shown in SEQ ID NO:1, SEQ ID NO:3, SEQ ID NO:4, SEQ ID NO:6, SEQ ID NO:7. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:4, SEQ ID NO:6, SEQ ID NO:7. In other embodiments, the invention provides a nucleic acid molecule which hybridizes under a stringency condition described herein to a nucleic acid molecule comprising the nucleotide sequence of SEQ ID NO:1, SEQ ID NO:3, SEQ ID NO:4, SEQ ID NO:6, SEQ ID NO:7, wherein the nucleic acid encodes a full length 52906, 33408, or 12189 protein or an active fragment thereof.

In a related aspect, the invention further provides nucleic acid constructs that include a 52906, 33408, or 12189 nucleic acid molecule described herein. In certain embodiments, the nucleic acid molecules of the invention are operatively linked to native or heterologous regulatory sequences. Also included, are vectors and host cells containing the 52906, 33408, or 12189 nucleic acid molecules of the invention e.g., vectors and host cells suitable for producing 52906, 33408, or 12189 nucleic acid molecules and polypeptides.

In another related aspect, the invention provides nucleic acid fragments suitable as primers or hybridization probes for the detection of 52906, 33408, or 12189-encoding nucleic acids.

In still another related aspect, isolated nucleic acid molecules that are antisense to a 52906, 33408, or 12189 encoding nucleic acid molecule are provided.

In another aspect, the invention features, 52906, 33408, or 12189 polypeptides, and biologically active or antigenic fragments thereof that are useful, e.g., as reagents or targets in assays applicable to treatment and diagnosis of 52906, 33408, or 12189-mediated or -related disorders. In another embodiment, the invention provides 52906, 33408, or 12189 polypeptides having a 52906, 33408, or 12189 activity. Preferred polypeptides are 52906, 33408, or 12189 proteins including at least one ion transport protein domain, and, preferably, having a 52906, 33408, or 12189 activity, e.g., a 52906, 33408, or 12189 activity as described herein.

In other embodiments, the invention provides 52906, 33408, or 12189 polypeptides, e.g., a 52906, 33408, or 12189 polypeptide having the amino acid sequence shown in SEQ ID NO:2, SEQ ID NO:5, SEQ ID NO:8; an amino acid sequence that is substantially identical to the amino acid sequence shown in SEQ ID NO:2, SEQ ID NO:5, SEQ ID NO:8; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, SEQ ID NO:4, SEQ ID NO:6, SEQ ID NO:7, wherein the nucleic acid encodes a full length 52906, 33408, or 12189 protein or an active fragment thereof.

In a related aspect, the invention further provides nucleic acid constructs which include a 52906, 33408, or 12189 nucleic acid molecule described herein.

In a related aspect, the invention provides 52906, 33408, or 12189 polypeptides or fragments operatively linked to non-52906, 33408, or 12189 polypeptides to form fusion proteins.

In another aspect, the invention features antibodies and antigen-binding fragments thereof, that react with, or more preferably specifically bind 52906, 33408, or 12189 polypeptides or fragments thereof, e.g., an ion transport protein domain, a cyclic nucleotide-binding domain, a potassium channel tetramerisation domain, a transmembrane domain, a cytoplasmic domain, an extracellular domain, a Pore-loop domain, or a PAS domain. In one embodiment, the antibodies or antigen-binding fragment thereof competitively inhibit the binding of a second antibody to a 52906, 33408, or 12189 polypeptide or a fragment thereof, e.g., an ion transport protein domain, a cyclic nucleotide-binding domain, a potassium channel tetramerisation domain, a transmembrane domain, a cytoplasmic domain, an extracellular domain, a Pore-loop domain, or a PAS domain.

In another aspect, the invention provides methods of screening for compounds that modulate the expression or activity of the 52906, 33408, or 12189 polypeptides or nucleic acids.

In still another aspect, the invention provides a process for modulating 52906, 33408, or 12189 polypeptide or nucleic acid expression or activity, e.g. using the screened compounds. In certain embodiments, the methods involve treatment of conditions related to aberrant activity or expression of the 52906, 33408, or 12189 polypeptides or nucleic acids, such as conditions characterized by abnormal ion flux such as a neurological disorder or a cardiac disorder.

The invention also provides assays for determining the activity of or the presence or absence of 52906, 33408, or 12189 polypeptides or nucleic acid molecules in a biological sample, including for disease diagnosis.

In yet another aspect, the invention provides methods for modulating (increasing or decreasing) the ion flux, e.g., the flow of $K^+$ ions, in a 52906, 33408, or 12189-expressing cell. The method includes contacting the cell with a compound (e.g., a compound identified using the methods described herein) that modulates the activity, or expression, of the 52906, 33408, or 12189 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol. In a preferred embodiment, the cell is an electrically excitable cell, e.g., a neuronal cell or a muscle cell (e.g., a heart cell). For example, the cell can be from brain or cardiac tissues.

In a preferred embodiment, the compound is an inhibitor of a 52906, 33408, or 12189 polypeptide. Preferably, the inhibitor is chosen from a peptide, a phosphopeptide, a small organic molecule, a small inorganic molecule and an antibody (e.g., an antibody conjugated to a therapeutic moiety). In another preferred embodiment, the compound is an inhibitor of a 52906, 33408, or 12189 nucleic acid, e.g., an antisense, a ribozyme, or a triple helix molecule.

In another aspect, the invention features methods for treating or preventing a disorder characterized by the abnormal ion flux of a 52906, 33408, or 12189-expressing cell, in a subject. Preferably, the method includes administering to the subject (e.g., a mammal, e.g., a human) an effective amount of a compound (e.g., a compound identified using the methods described herein) that modulates the activity, or expression, of the 52906, 33408, or 12189 polypeptide or nucleic acid. In a preferred embodiment, the disorder is a neurological disorder or a cardiac disorder.

In a further aspect, the invention provides methods for evaluating the efficacy of a treatment of a disorder, e.g., a disorder characterized by abnormal ion flux such as a neurological disorder or a cardiac disorder. The method includes: treating a subject, e.g., a patient or an animal, with a protocol under evaluation (e.g., treating a subject with a compound identified using the methods described herein); and evaluating the expression of a 52906, 33408, or 12189 nucleic acid or polypeptide before and after treatment. A change, e.g., a decrease or increase, in the level of a 52906, 33408, or 12189 nucleic acid (e.g., mRNA) or polypeptide after treatment, relative to the level of expression before treatment, is indicative of the efficacy of the treatment of the disorder. The level of 52906, 33408, or 12189 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 52906, 33408, or 12189 nucleic acid (e.g., mRNA) or polypeptide before and after treatment.

In another aspect, the invention provides methods for evaluating the efficacy of a therapeutic or prophylactic agent. The method includes: contacting a sample with an agent (e.g., a compound identified using the methods described herein) and, evaluating the expression of 52906, 33408, or 12189 nucleic acid or polypeptide in the sample before and after the contacting step. A change, e.g., a decrease or increase, in the level of 52906, 33408, or 12189 nucleic acid (e.g., mRNA) or polypeptide in the sample obtained after the contacting step, relative to the level of expression in the sample before the contacting step, is indicative of the efficacy of the agent. The level of 52906, 33408, or 12189 nucleic acid or polypeptide expression can be detected by any method described herein. In a preferred embodiment, the sample includes neuronal cells or muscle cells.

In further aspect, the invention provides assays for determining the presence or absence of a genetic alteration in a 52906, 33408, or 12189 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 52906, 33408, or 12189 molecule. In one embodiment, the capture probe is a nucleic acid, e.g., a probe complementary to a 52906, 33408, or 12189 nucleic acid sequence. In another embodiment, the capture probe is a polypeptide, e.g., an antibody specific for 52906, 33408, or 12189 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIG. 2 depicts an alignment of the ion transport protein domain of human 52906 with a consensus amino acid sequence derived from a hidden Markov model (HMM) from PFAM. The upper sequence is the consensus amino acid sequence (SEQ ID NO:9), while the lower amino acid sequence corresponds to amino acids 472 to 661 of SEQ ID NO:2.

FIG. 4A depicts an alignment of the ion transport protein domain of human 33408 with a consensus amino acid sequence derived from a hidden Markov model (HMM) from PFAM. The upper sequence is the consensus amino acid sequence (SEQ ID NO:9), while the lower amino acid sequence corresponds to amino acids 247 to 467 of SEQ ID NO:5.

FIG. 4B depicts an alignment of the cyclic nucleotide-binding domain of human 33408 with a consensus amino acid sequence derived from a hidden Markov model (HMM) from PFAM. The upper sequence is the consensus amino acid sequence (SEQ ID NO:10), while the lower amino acid sequence corresponds to amino acids 565 to 655 of SEQ ID NO:5.

FIGS. 4C–D depicts an alignment of the amino acid sequence of human 33408 (upper sequence; SEQ ID NO:5) with the amino acid sequence of rat Eag2 (lower sequence; Accession Number AF185637; SEQ. ID NO:12).

FIG. 6A depicts an alignment of the potassium channel tetramerisation domain of human 12189 with a consensus amino acid sequence derived from a hidden Markov model (HMM) from PFAM. The upper sequence is the consensus amino acid sequence (SEQ ID NO:11), while the lower amino acid sequence corresponds to amino acids 3 to 101 of SEQ ID NO:8.

FIG. 6B depicts an alignment of the ion transport protein domain of human 12189 with a consensus amino acid sequence derived from a hidden Markov model (HMM) from PFAM. The upper sequence is the consensus amino acid sequence (SEQ ID NO:9), while the lower amino acid sequence corresponds to amino acids 198 to 383 of SEQ ID NO:8.

FIG. 6C depicts an alignment of the amino acid sequence of human 12189 (lower sequence) with the amino acid sequence of mouse Kv1.7 (upper sequence; Accession Number AF032099; SEQ ID NO:13).

DETAILED DESCRIPTION

Human 52906

Figure 1:
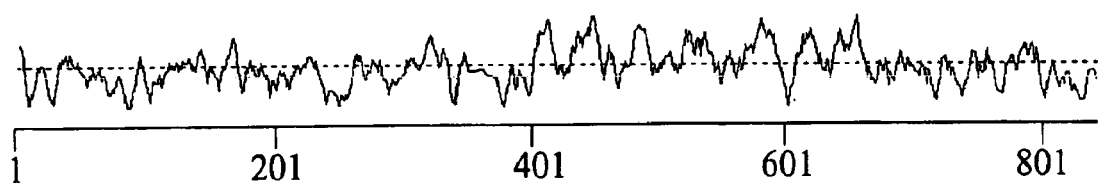
FIG. 1 depicts a hydropathy plot of human 52906. Relative hydrophobic residues are shown above the dashed horizontal line, and relative hydrophilic residues are below the dashed horizontal line. Numbers corresponding to positions in the amino acid sequence of human 52906 are indicated. Polypeptides of the invention include fragments which include: all or part of a hydrophobic sequence, i.e., a sequence above the dashed line, e.g., the sequence from about amino acid 785–800 of SEQ ID NO:2; all or part of a hydrophilic sequence, i.e., a sequence below the dashed line, e.g., the sequence of from about amino acid 241–265 of SEQ ID NO:2.

The human 52906 sequence (see SEQ ID NO:1, as recited in Example 1), which is approximately 3525 nucleotides long including untranslated regions, contains a predicted methionine-initiated coding sequence of about 2544 nucleotides, including the termination codon. The coding sequence encodes a 847 amino acid protein (see SEQ ID NO:2, as recited in Example 1). The hydropathy plot of 52906 is depicted in FIG. 1.

Human 52906 contains the following regions or structural features: an ion transport protein domain (PFAM Accession Number PF00520) located at about amino acid residues 472 to 661 of SEQ ID NO:2 (see FIG. 2); and a core membrane region consisting of six transmembrane domains, four cytoplasmic domains, three extracellular domains, and a Pore-loop domain. The core membrane region is located at about amino acid 402 to about amino acid 662 of SEQ ID NO:2. The six transmembrane domains are located at about amino acid 402 (cytoplasmic end) to about amino acid 419

(extracellular end) of SEQ ID NO:2, about amino acid 433 (extracellular end) to about amino acid 456 (cytoplasmic end) of SEQ ID NO:2, about amino acid 482 (cytoplasmic end) to about amino acid 498 (extracellular end) of SEQ ID NO:2, about amino acid 524 (extracellular end) to about amino acid 543 (cytoplasmic end) of SEQ ID NO:2, about amino acid 573 (cytoplasmic end) to about amino acid 597 (extracellular end) of SEQ ID NO:2, and about amino acid 641 (extracellular end) to about amino acid 662 (cytoplasmic end) of SEQ ID NO:2. The four cytoplasmic domains are located at about amino acids 1 to 401 (amino terminus), 457 to 481, 544 to 572, and 663 to 847 (carboxy terminus) of SEQ ID NO:2. The three extracellular domains are located at about amino acids 420 to 432, 499 to 523, and 598 to 640 of SEQ ID NO:2. The extracellular domain located at about amino acids 598 to 640 includes a Pore-loop domain (P-loop domain) located at about amino acid residues 616 to 639 of SEQ ID NO:2.

The 52906 protein also includes the following domains: six predicted N-glycosylation sites (PS00001) located at about amino acids 10–13, 141–144, 182–185, 284–287, 342–345, and 500–503 of SEQ ID NO:2; one predicted glycosaminoglycan attachment site (PS00002) located at about amino acids 367–370 of SEQ ID NO:2; four predicted cAMP- and cGMP-dependent protein kinase phosphorylation sites (PS00004) located at about amino acids 176–179, 258–261, 400–403, and 832–835 of SEQ ID NO:2; 13 predicted Protein Kinase C phosphorylation sites (PS00005) located at about amino acids 9–11, 12–14, 174–176, 271–273, 288–290, 377–379, 506–508, 552–554, 596–598, 684–686, 732–734, 799–801, and 829–831 of SEQ ID NO:2; seven predicted Casein Kinase II phosphorylation sites (PS00006) located at about amino acids 330–333, 337–340, 518–521, 668–671, 746–749, 780–783, and 842–845 of SEQ ID NO:2; 15 predicted N-myristoylation sites (PS00008) located at about amino acids 21–26, 42–47, 118–123, 132–137, 153–158, 165–170, 178–183, 227–232, 309–314, 351–356, 359–364, 366–371, 374–379, 647–652, and 787–792 of SEQ ID NO:2; and one predicted coiled coil located at about amino acids 719–791 of SEQ ID NO:2.

For general information regarding PFAM identifiers, PS prefix and PF prefix domain identification numbers, refer to Sonnhammer et al. (1997) *Protein* 28:405–420 and www.psc.edu/general/software/packages/pfam/pfam.html.

An alignment of the human 52906 amino acid sequence with the rat SK2 amino acid sequence (Accession Number U69882) suggests that 52906 is a human ortholog of rat SK2, a calcium activated potassium channel (Köhler et al. (1996) *Science* 273:1709–1714).

Human 33408

Figure 3:
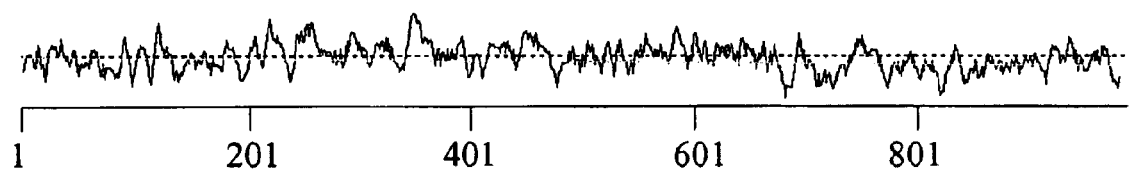
FIG. 3 depicts a hydropathy plot of human 33408. Relative hydrophobic residues are shown above the dashed horizontal line, and relative hydrophilic residues are below the dashed horizontal line. Numbers corresponding to positions in the amino acid sequence of human 33408 are indicated. Polypeptides of the invention include fragments which include: all or part of a hydrophobic sequence, i.e., a sequence above the dashed line, e.g., the sequence from about amino acid 585–600 of SEQ ID NO:5; all or part of a hydrophilic sequence, i.e., a sequence below the dashed line, e.g., the sequence of from about amino acid 710–740 of SEQ ID NO:5.

The human 33408 sequence (see SEQ ID NO:4, as recited in Example 1), which is approximately 3553 nucleotides long including untranslated regions, contains a predicted methionine-initiated coding sequence of about 2967 nucleotides, including the termination codon. The coding sequence encodes a 988 amino acid protein (see SEQ ID NO:5, as recited in Example 1). The hydropathy plot of 33408 is depicted in FIG. 3.

Human 33408 contains the following regions or structural features: an ion transport protein domain (PFAM Accession Number PF00520) located at about amino acid residues 247 to 467 of SEQ ID NO:5 (see FIG. 4A); a cyclic nucleotide-binding domain (PFAM Accession Number PF00027) located at about amino acid residues 565 to 655 of SEQ ID NO:5 (see FIG. 4B); and a core membrane region consisting of six transmembrane domains, four cytoplasmic domains, three extracellular domains, a Pore-loop domain, and a PAS domain. The core membrane region is located at about amino acid 219 to about amino acid 471 of SEQ ID NO:5. The six transmembrane domains are located at about amino acid 219 (cytoplasmic end) to about amino acid 236 (extracellular end) of SEQ ID NO:5, about amino acid 245 (extracellular end) to about amino acid 264 (cytoplasmic end) of SEQ ID NO:5, about amino acid 292 (cytoplasmic end) to about amino acid 309 (extracellular end) of SEQ ID NO:5, about amino acid 320 (extracellular end) to about amino acid 337 (cytoplasmic end) of SEQ ID NO:5, about amino acid 344 (cytoplasmic end) to about amino acid 368 (extracellular end) of SEQ ID NO:5, and about amino acid 447 (extracellular end) to about amino acid 471 (cytoplasmic end) of SEQ ID NO:5. The four cytoplasmic domains are located at about amino acids 1 to 218 (amino terminus), 265 to 291, 338 to 343, and 472 to 988 (carboxy terminus) of SEQ ID NO:5. The three extracellular domains are located at about amino acids 237 to 244, 310 to 319, and 369 to 446 of SEQ ID NO:5. The extracellular domain located at about amino acids 369 to 446 includes a Pore-loop domain (P-loop domain) located at about amino acid residues 420 to 440 of SEQ ID NO:5. The cytoplasmic domain located at about amino acids 1 to 218 includes a PAS domain located at about amino acid residues 1–134 of SEQ ID NO:5 and a PAC domain located at about amino acid residues 92–132 of SEQ ID NO:5.

The 33408 protein also includes the following domains: seven predicted N-glycosylation sites (PS00001) located at about amino acids 170–173, 235–238, 403–406, 466–469, 663–666, 743–746, and 830–833 of SEQ ID NO:5; two predicted cAMP- and cGMP-dependent protein kinase phosphorylation sites (PS00004) located at about amino acids 21–24 and 677–680 of SEQ ID NO:5; 13 predicted Protein Kinase C phosphorylation sites (PS00005) located at about amino acids 73–75, 127–129, 142–144, 237–239, 322–324, 478–480, 502–504, 521–523, 773–775, 925–927, 943–945, 952–954, and 981–983 of SEQ ID NO:5; 16 predicted Casein Kinase II phosphorylation sites (PS00006) located at about amino acids 14–17, 127–130, 215–218, 252–255, 369–372, 442–445, 634–637, 725–728, 832–835, 847–850, 869–872, 883–886, 909–912, 929–932, 974–977, and 981–984 of SEQ ID NO:5; eight predicted N-myristoylation sites (PS00008) located at about amino acids 3–8, 407–412, 465–470, 557–562, 723–728, 744–749, 806–811, and 867–872 of SEQ ID NO:5; one predicted amidation site (PS00009) located at about amino acids 3–6 of SEQ ID NO:5; one predicted leucine zipper pattern (PS00029) located at about amino acids 910–931 of SEQ ID NO:5; and one predicted coiled coil located at about amino acids 906–944 of SEQ ID NO:5.

An alignment of the human 33408 amino acid sequence with the rat Eag2 amino acid sequence (SEQ ID NO: 12; Accession Number AF185637) is depicted in FIGS. 4C–4D. 33408 appears to be a human ortholog of rat Eag2, a subthreshold activating potassium channel (Saganich et al. (1999) *J. Neuroscience* 19:10789–10802).

Human 12189

Figure 5:
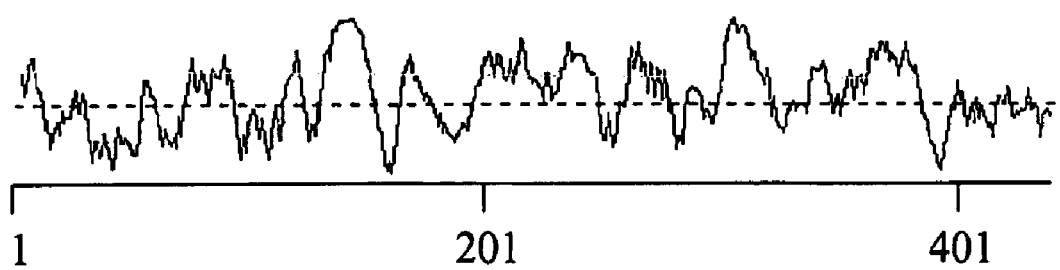
FIG. 5 depicts a hydropathy plot of human 12189. Relative hydrophobic residues are shown above the dashed horizontal line, and relative hydrophilic residues are below the dashed horizontal line. Numbers corresponding to positions in the amino acid sequence of human 12189 are indicated. Polypeptides of the invention include fragments which include: all or part of a hydrophobic sequence, i.e., a sequence above the dashed line, e.g., the sequence from about amino acid 75–95 of SEQ ID NO:8; all or part of a hydrophilic sequence, i.e., a sequence below the dashed line, e.g., the sequence of from about amino acid 35–55 of SEQ ID NO:8.

The human 12189 sequence (see SEQ ID NO:7, as recited in Example 1), which is approximately 1341 nucleotides long, contains a predicted coding sequence, including a termination codon. The coding sequence encodes a 446 amino acid protein (see SEQ ID NO:8, as recited in Example 1). The hydropathy plot of 12189 is depicted in FIG. 5.

Human 12189 contains the following regions or structural features: a potassium channel tetramerisation domain (PFAM Accession Number PF02214) located at about amino acid residues 3 to 101 of SEQ ID NO:8 (see FIG. 6A); an ion transport protein domain (PFAM Accession Number PF00520) located at about amino acid residues 198 to 383 of SEQ ID NO:8 (see FIG. 6B); and a core membrane region consisting of six transmembrane domains, four cytoplasmic domains, three extracellular domains, and a Pore-loop domain. The core membrane region is located at about amino acid 134 to about amino acid 384 of SEQ ID NO:8. The six transmembrane domains are located at about amino acid 134 (cytoplasmic end) to about amino acid 152 (extracellular end) of SEQ ID NO:8, about amino acid 200 (extracellular end) to about amino acid 222 (cytoplasmic end) of SEQ ID NO:8, about amino acid 231 (cytoplasmic end) to about amino acid 248 (extracellular end) of SEQ ID NO:8, about amino acid 266 (extracellular end) to about amino acid 286 (cytoplasmic end) of SEQ ID NO:8, about amino acid 302 (cytoplasmic end) to about amino acid 323 (extracellular end) of SEQ ID NO:8, and about amino acid 363 (extracellular end) to about amino acid 384 (cytoplasmic end) of SEQ ID NO:8. The four cytoplasmic domains are located at about amino acids 1 to 133 (amino terminus), 223 to 230, 287 to 301, and 385 to 446 (carboxy terminus) of SEQ ID NO:8. The three extracellular domains are located at about amino acids 153 to 199, 249 to 265, and 324 to 362 of SEQ ID NO:8. The extracellular domain located at about amino acids 324 to 362 includes a Pore-loop domain (P-loop domain) located at about amino acid residues 339 to 355 of SEQ ID NO:8.

The 12189 protein also includes the following domains: two predicted N-glycosylation sites (PS00001) located at about amino acids 181–184 and 386–389 of SEQ ID NO:8; two predicted Protein Kinase C phosphorylation sites (PS00005) located at about amino acids 294–296 and 298–300 of SEQ ID NO:8; five predicted Casein Kinase II phosphorylation sites (PS00006) located at about amino acids 154–157, 298–301, 334–337, 395–398, and 404–407 of SEQ ID NO:8; one predicted tyrosine kinase phosphorylation site (PS00007) located at about amino acids 52–60 of SEQ ID NO:8; five predicted N-myristoylation sites (PS00008) located at about amino acids 87–92, 164–169, 248–253, 365–370, and 421–426 of SEQ ID NO:8; and one predicted leucine zipper pattern (PS00029) located at about amino acids 281–302 of SEQ ID NO:8.

An alignment of the human 12189 amino acid sequence with the mouse Kv1.7 amino acid sequence (SEQ ID NO:13; Accession Number AF032099) is depicted in FIG. 6C. 12189 appears to be a human ortholog of mouse Kv1.7, a voltage-gated potassium channel (Kalman et al. (1998) *J. Biol. Chem.* 273:5851–5857).

TABLE 1

Summary of Sequence Information for 52906, 33408, and 12189

| Gene | cDNA | ORF | Polypeptide |
|---|---|---|---|
| 52906 | SEQ ID NO:1 | SEQ ID NO:3 | SEQ ID NO:2 |
| 33408 | SEQ ID NO:4 | SEQ ID NO:6 | SEQ ID NO:5 |
| 12189 | SEQ ID NO:7 |  | SEQ ID NO:8 |

TABLE 2

Summary of Domains of 52906, 33408, and 12189

| Domain | 52906 | 33408 | 12189 |
|---|---|---|---|
| Transmembrane Region | amino acids 402–662 of SEQ ID NO:2 | amino acids 219–471 of SEQ ID NO:5 | amino acids 134–384 of SEQ ID NO:8 |
| Transmembrane Domain 1 | amino acids 402–419 of SEQ ID NO:2 | amino acids 219–236 of SEQ ID NO:5 | amino acids 134–152 of SEQ ID NO:8 |
| Transmembrane Domain 2 | amino acids 433–456 of SEQ ID NO:2 | amino acids 245–264 of SEQ ID NO:5 | amino acids 200–222 of SEQ ID NO:8 |
| Transmembrane Domain 3 | amino acids 482–498 of SEQ ID NO:2 | amino acids 292–309 of SEQ ID NO:5 | amino acids 231–248 of SEQ ID NO:8 |
| Transmembrane Domain 4 | amino acids 524–543 of SEQ ID NO:2 | amino acids 320–337 of SEQ ID NO:5 | amino acids 266–286 of SEQ ID NO:8 |
| Transmembrane Domain 5 | amino acids 573–597 of SEQ ID NO:2 | amino acids 344–368 of SEQ ID NO:5 | amino acids 302–323 of SEQ ID NO:8 |
| Transmembrane Domain 6 | amino acids 641–662 of SEQ ID NO:2 | amino acids 447–471 of SEQ ID NO:5 | amino acids 363–384 of SEQ ID NO:8 |
| Cytoplasmic Domain 1 | amino acids 1–401 of SEQ ID NO:2 | amino acids 1–218 of SEQ ID NO:5 | amino acids 1–133 of SEQ ID NO:8 |
| Cytoplasmic Domain 2 | amino acids 457–481 of SEQ ID NO:2 | amino acids 265–291 of SEQ ID NO:5 | amino acids 223–230 of SEQ ID NO:8 |
| Cytoplasmic Domain 3 | amino acids 544–572 of SEQ ID NO:2 | amino acids 338–343 of SEQ ID NO:5 | amino acids 287–301 of SEQ ID NO:8 |
| Cytoplasmic Domain 4 | amino acids 663–847 of SEQ ID NO:2 | amino acids 472–988 of SEQ ID NO:5 | amino acids 385–446 of SEQ ID NO:8 |
| Extracellular Domain 1 | amino acids 420–432 of SEQ ID NO:2 | amino acids 237–244 of SEQ ID NO:5 | amino acids 153–199 of SEQ ID NO:8 |
| Extracellular Domain 2 | amino acids 499–523 of SEQ ID NO:2 | amino acids 310–319 of SEQ ID NO:5 | amino acids 249–265 of SEQ ID NO:8 |
| Extracellular Domain 3 | amino acids 598–640 of SEQ ID NO:2 | amino acids 369–446 of SEQ ID NO:5 | amino acids 324–362 of SEQ ID NO:8 |
| Pore-loop Domain | amino acids 616–639 of SEQ ID NO:2 | amino acids 420–440 of SEQ ID NO:5 | amino acids 339–355 of SEQ ID NO:8 |

TABLE 2-continued

Summary of Domains of 52906, 33408, and 12189

| Domain | 52906 | 33408 | 12189 |
|---|---|---|---|
| ion transport protein domain | amino acids 472–661 of SEQ ID NO:2 | amino acids 247–467 of SEQ ID NO:5 | amino acids 198–383 of SEQ ID NO:8 |
| cyclic nucleotide binding domain | | amino acids 565–655 of SEQ ID NO:5 | |
| potassium channel tetramerisation domain | | | amino acids 3–101 of SEQ ID NO:8 |

The 52906, 33408, and 12189 proteins contain a significant number of structural characteristics in common with members of the potassium channel family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, a "potassium channel" includes a protein or polypeptide which is involved in receiving, conducting, and transmitting signals in an electrically excitable cell, e.g., a neuronal cell or a muscle cell. Potassium channels are potassium ion selective, and can determine membrane excitability (the ability of, for example, a neuron to respond to a stimulus and convert it into an impulse). Potassium channels can also influence the resting potential of membranes, wave forms and frequencies of action potentials, and thresholds of excitation. Potassium channels are typically expressed in electrically excitable cells, e.g., neurons, muscle, endocrine, and egg cells, and may form heteromultimeric structures, e.g., composed of pore-forming α and cytoplasmic β subunits. Potassium channels may also be found in nonexcitable cells (e.g., thymus cells), where they may play a role in, e.g., signal transduction. Potassium channel proteins contain six transmembrane helices, wherein the last two helices flank a loop (a P-loop) which determines potassium ion selectivity. Examples of potassium channels include: (1) the voltage-gated potassium channels, (2) the ligand-gated potassium channels, e.g., neurotransmitter-gated potassium channels, and (3) cyclic-nucleotide-gated potassium channels. Voltage-gated and ligand-gated potassium channels are expressed in the brain, e.g., in brainstem monoaminergic and forebrain cholinergic neurons, where they are involved in the release of neurotransmitters, or in the dendrites of hippocampal and neocortical pyramidal cells, where they are involved in the processes of learning and memory formation. For a detailed description of potassium channels, see Kandel E. R. et al., Principles of Neural Science, second edition, (Elsevier Science Publishing Co., Inc., N.Y. (1985)), the contents of which are incorporated herein by reference.

A 52906, 33408, or 12189 polypeptide can include a "transmembrane domain" or regions homologous with a "transmembrane domain".

As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235–263, the contents of which are incorporated herein by reference. Amino acid residues 402–419, 433–456, 482–498, 524–543, 573–597, and 641–662 of the 52906 protein (SEQ ID NO:2) are predicted to comprise transmembrane domains (see FIG. 2). Accordingly, 52906 proteins having at least 50–60% homology, preferably about 60–70%, more preferably about 70–80%, or about 80–90% homology with a transmembrane domain of human 52906 are within the scope of the invention. Amino acid residues 219–236, 245–264, 292–309, 320–337, 344–368, and 447–471 of the 33408 protein (SEQ ID NO:5) are predicted to comprise transmembrane domains (see FIG. 5). Accordingly, 33408 proteins having at least 50–60% homology, preferably about 60–70%, more preferably about 70–80%, or about 80–90% homology with a transmembrane domain of human 33408 are within the scope of the invention. Amino acid residues 134–152, 200–222, 231–248, 266–286, 302–323, and 363–384 of the 12189 protein (SEQ ID NO:8) are predicted to comprise transmembrane domains (see FIG. 8). Accordingly, 12189 proteins having at least 50–60% homology, preferably about 60–70%, more preferably about 70–80%, or about 80–90% homology with a transmembrane domain of human 12189 are within the scope of the invention.

A 52906, 33408, or 12189 polypeptide can further include a "Pore loop" or regions homologous with a "Pore loop domain".

As used herein, the term "Pore loop" or "P-loop" includes amino acid sequence of about 15–45 amino acid residues in length, preferably about 15–35 amino acid residues in length, and most preferably about 15–25 amino acid residues in length, which is hydrophobic and which is involved in lining the potassium channel pore. A P-loop is typically found between transmembrane domains of potassium channels and is believed to be a major determinant of ion selectivity in potassium channels. Preferably, P-loops contain a G-[HYDROPHOBIC AMINO ACID]-G sequence, e.g., a GYG, GLG, or GFG sequence. P-loops are described in, for example, Warnike et al. (1991) *Science* 252:1560–1562; Zagotta W. N. et al., (1996) *Annual Rev. Neuronsci.* 19:235–63 (Pongs, O. (1993) *J. Membr. Biol.*, 136, 1–8; Heginbotham et al. (1994) *Biophys. J.* 66,1061–1067; Mackinnon, R. (1995) *Neuron*, and 14, 889–892; Pascual et al., (1995) *Neuron.*, 14, 1055–1063), the contents of which are incorporated herein by reference. Amino acid residues 616–639 of SEQ ID NO:2, 420–440 of SEQ ID NO:5, and 339–355 of SEQ ID NO:8 comprise P-loop domains. Accordingly, proteins having at least 50–60% homology, preferably about 60–70%, more preferably about 70–80%, or about 80–90% homology with a-loop domain of human 52906, 33408, or 12189 are within the scope of the invention.

In one embodiment, a 52906, 33408, or 12189 protein includes at least one cytoplasmic domain. When located at the N-terminal domain the cytoplasmic domain is referred to herein as an "N-terminal cytoplasmic domain". As used herein, an "N-terminal cytoplasmic domain" includes an amino acid sequence having about 1–500, preferably about 1–450, preferably about 1–400, preferably about 1–380, more preferably about 1–350, more preferably about 1–300, more preferably about 1–220, or even more preferably about 1–135 amino acid residues in length and is located inside of a cell or intracellularly. The C-terminal amino acid residue of a "N-terminal cytoplasmic domain" is adjacent to an N-terminal amino acid residue of a transmembrane domain in a 52906, 33408, or 12189 protein. For example, an N-terminal cytoplasmic domain is located at about amino acid residues 1–401 of SEQ ID NO:2, 1–218 of SEQ ID NO:5, or 1–133 of SEQ ID NO:8.

In a preferred embodiment, a 52906, 33408, or 12189 polypeptide or protein has at least one cytoplasmic domain or a region which includes at least about 5, preferably about 5–10, and more preferably about 10–20 amino acid residues and has at least about 60%, 70%, 80%, 90%, 95%, 99%, or 100% homology with an "cytoplasmic domain," e.g., at least one cytoplasmic domain of human 52906, 33408, or 12189 (e.g., residues 1–401, 457–481, 544–572, and 663–847 of SEQ ID NO:2; residues 1–218, 265–291, 338–343, and 447–988 of SEQ ID NO:5; and residues 1–133, 223–230, 287–301, and 385–446 of SEQ ID NO:8).

In another embodiment, a 52906, 33408, or 12189 protein includes at least one extracellular loop. As used herein, the term "loop" includes an amino acid sequence having a length of at least about 4, preferably about 5–10, and more preferably about 10–20 amino acid residues, and has an amino acid sequence that connects two transmembrane domains within a protein or polypeptide. Accordingly, the N-terminal amino acid of a loop is adjacent to a C-terminal amino acid of a transmembrane domain in a 52906, 33408, or 12189 molecule, and the C-terminal amino acid of a loop is adjacent to an N-terminal amino acid of a transmembrane domain in a 52906, 33408, or 12189 molecule. As used herein, an "extracellular loop" includes an amino acid sequence located outside of a cell, or extracellularly. For example, an extracellular loop can be found at about amino acids 420–432, 499–523, and 598–640 of SEQ ID NO:2; at about amino acids 237–244, 310–319, and 369–446 of SEQ ID NO:5; and at about amino acids 153–199, 249–265, and 324–362 of SEQ ID NO:8.

In a preferred embodiment, a 52906, 33408, or 12189 polypeptide or protein has at least one extracellular loop or a region which includes at least about 4, preferably about 5–10, preferably about 10–20, and more preferably about 20–30 amino acid residues and has at least about 60%, 70%, 80%, 90%, 95%, 99%, or 100% homology with an "extracellular loop," e.g., at least one extracellular loop of human 52906, 33408, or 12189 (e.g., residues 420–432, 499–523, and 598–640 of SEQ ID NO:2; residues 237–244, 310–319, and 369–446 of SEQ ID NO:5; and residues 153–199, 249–265, and 324–362 of SEQ ID NO:8).

In another embodiment, a 52906, 33408, or 12189 protein includes a "C-terminal cytoplasmic domain", also referred to herein as a C-terminal cytoplasmic tail, in the sequence of the protein. As used herein, a "C-terminal cytoplasmic domain" includes an amino acid sequence having a length of at least about 50, preferably about 500–550, preferably about 150–200, more preferably about 50–70 amino acid residues and is located within a cell or within the cytoplasm of a cell. Accordingly, the N-terminal amino acid residue of a "C-terminal cytoplasmic domain" is adjacent to a C-terminal amino acid residue of a transmembrane domain in a 52906, 33408, or 12189 protein. For example, a C-terminal cytoplasmic domain is found at about amino acid residues 663–847 of SEQ ID NO:2; at about amino acid residues 472–988 of SEQ ID NO:5; and at about amino acid residues 385–446 of SEQ ID NO:8.

In a preferred embodiment, a 52906, 33408, or 12189 polypeptide or protein has a C-terminal cytoplasmic domain or a region which includes at least about 50, preferably about 150–550, more preferably about 50–70 amino acid residues and has at least about 60%, 70%, 80%, 90%, 95%, 99%, or 100% homology with an "C-terminal cytoplasmic domain," e.g., the C-terminal cytoplasmic domain of human 52906, 33408, or 12189 (e.g., residues 663–847 of SEQ ID NO:2; residues 472–988 of SEQ ID NO:5; and residues 385–446 of SEQ ID NO:8).

A 52906, 33408, or 12189 polypeptide can include an "ion transport protein domain" or regions homologous with an "ion transport protein domain."

As used herein, the term "ion transport protein domain" includes an amino acid sequence of about 100 to 300 amino acid residues in length and having a bit score for the alignment of the sequence to the ion transport protein domain profile (Pfam HMM) of at least 50. Preferably, a ion transport protein domain includes at least about 150 to 280 amino acids, more preferably about 170 to 260 amino acid residues, or about 180 to 230 amino acids and has a bit score for the alignment of the sequence to the ion transport protein domain (HMM) of at least 90 or greater. The ion transport protein domain (HMM) has been assigned the PFAM Accession Number PF00520 (genome.wustl.edu/Pfam/.html). An alignment of the ion transport protein domain (amino acids 472–661 of SEQ ID NO:2) of human 52906 with a consensus amino acid sequence (SEQ ID NO:9) derived from a hidden Markov model is depicted in FIG. 2. An alignment of the ion transport protein domain (amino acids 247–467 of SEQ ID NO:5) of human 33408 with a consensus amino acid sequence (SEQ ID NO:9) derived from a hidden Markov model is depicted in FIG. 4A. An alignment of the ion transport protein domain (amino acids 198–383 of SEQ ID NO:8) of human 12189 with a consensus amino acid sequence (SEQ ID NO:9) derived from a hidden Markov model is depicted in FIG. 6B.

In a preferred embodiment, a 52906, 33408, or 12189 polypeptide or protein has an "ion transport protein domain" or a region which includes at least about 150 to 280 more preferably about 170 to 260 or 180 to 230 amino acid residues and has at least about 50%, 60%, 70%, 80%, 90%, 95%, 99%, or 100% homology with a "ion transport protein domain," e.g., the ion transport protein domain of human 52906, 33408, or 12189 (e.g., residues 472–661 of SEQ ID NO:2, 247–467 of SEQ ID NO:5, or 198–383 of SEQ ID NO:8).

A 33408 molecule can further include a cyclic nucleotide binding domain or regions homologous with a "cyclic nucleotide binding domain."

As used herein, the term "cyclic nucleotide binding domain" includes an amino acid sequence of about 40–180 amino acid residues in length and having a bit score for the alignment of the sequence to the cyclic nucleotide binding domain (HMM) of at least 50. Preferably, a cyclic nucleotide binding domain is capable of binding a cyclic nucleotide. Preferably, a cyclic nucleotide binding domain includes at least about 50–150 amino acids, more preferably about 70–120 amino acid residues, or about 80–100 amino acids and has a bit score for the alignment of the sequence to the cyclic nucleotide binding domain (HMM) of at least 80 or greater. The cyclic nucleotide binding domain (HMM) has been assigned the PFAM Accession PF00027 (genome.wustl.edu/Pfam/html). An alignment of the cyclic nucleotide binding domain (amino acids 565 to 655 of SEQ ID NO:5) of human 33408 with a consensus amino acid sequence (SEQ ID NO: 10) derived from a hidden Markov model is depicted in FIG. 4B.

In a preferred embodiment a 33408 polypeptide or protein has a "cyclic nucleotide binding domain" or a region which includes at least about 50–150, more preferably about 70–120 or 80–100 amino acid residues and has at least about 50%, 60%, 70%, 80%, 90% 95%, 99%, or 100% homology with a "cyclic nucleotide binding domain," e.g., the cyclic nucleotide binding domain of human 33408 (e.g., residues 565 to 655 of SEQ ID NO:5).

A 12189 polypeptide can further include a "potassium channel tetramerisation domain" or regions homologous with a "potassium channel tetramerisation domain."

As used herein, the term "potassium channel tetramerisation domain" includes an amino acid sequence of about 50 to 200 amino acid residues in length and having a bit score for the alignment of the sequence to the potassium channel tetramerisation domain profile (Pfam HMM) of at least 100. A "potassium channel tetramerisation domain" promotes the assembly of alpha-subunits into functional tetrameric channels. Preferably, a potassium channel tetramerisation domain includes at least about 60 to 150 amino acids, more preferably about 70 to 130 amino acid residues, or about 90 to 110 amino acids and has a bit score for the alignment of the sequence to the potassium channel tetramerisation domain (HMM) of at least 165 or greater. The potassium channel tetramerisation domain (HMM) has been assigned the PFAM Accession Number PF02214 (genome.wustl.edu/Pfam/.html). An alignment of the potassium channel tetramerisation domain (amino acids 3–101 of SEQ ID NO:8) of human 12189 with a consensus amino acid sequence (SEQ ID NO:11) derived from a hidden Markov model is depicted in FIG. 6A.

In a preferred embodiment, a 12189 polypeptide or protein has a "potassium channel tetramerisation domain" or a region which includes at least about 60 to 150 more preferably about 70 to 130 or 90 to 110 amino acid residues and has at least about 50%, 60%, 70%, 80%, 90%, 95%, 99%, or 100% homology with a "potassium channel tetramerisation domain," e.g., the potassium channel tetramerisation domain of human 12189 (e.g., residues 3–101 of SEQ ID NO:8).

To identify the presence of an "ion transport protein" domain, a "cyclic nucleotide-binding" domain, or a "potassium channel tetramerisation" domain in a 52906, 33408, or 12189 protein sequence, and make the determination that a polypeptide or protein of interest has a particular profile, the amino acid sequence of the protein can be searched against the Pfam database of HMMs (e.g., the Pfam database, release 2.1) using the default parameters (www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

A 33408 polypeptide can further include a "PAS domain" or regions homologous with a "PAS domain". As used herein, a "PAS domain" includes an amino acid sequence of about 100–200 amino acid residues in length that is involved in ligand and/or protein-protein interactions. Preferably, the PAS domain interacts with the body of the channel, affecting gating, inactivation, and/or voltage sensitivity. Preferably, the PAS domain is located at the N-terminal cytoplasmic region of the 33408 polypeptide.

In a preferred embodiment, a 33408 polypeptide or protein has a "PAS domain" or a region which includes at least about 50–220, more preferably about 100–200 or 120–140 amino acid residues and has at least about 50%, 60%, 70%, 80%, 90%, 95%, 99%, or 100% homology with a "PAS domain," e.g., the PAS domain of human 33408 (e.g., residues 1–134 of SEQ ID NO:5).

A 33408 polypeptide can further include a "PAC domain" or regions homologous with a "PAC domain". As used herein, a "PAC domain" includes an amino acid sequence of about 30–50 amino acid residues in length. Preferably, the PAC domain contributes to the folding of the PAS domain. Preferably, the PAC domain is located at the C-terminal end of the PAS domain in a 33408 polypeptide.

In a preferred embodiment, a 33408 polypeptide or protein has a "PAC domain" or a region which includes at least about 20–70 or 30–50 amino acid residues and has at least about 50%, 60%, 70%, 80%, 90%, 95%, 99%, or 100% homology with a "PAC domain," e.g., the PAC domain of human 33408 (e.g., residues 92–132 of SEQ ID NO:5).

A 52906 family member can include at least one (preferably two, three, four, five, or six) transmembrane domain, at least one (preferably two or three) cytoplasmic domain, at least one (preferably two or three) extracellular domain, at least one P-loop domain, and at least one ion transport protein domain. Furthermore, a 52906, 33408, or 12189 family member can include: at least one, two, three, four, five, and preferably six predicted N-glycosylation sites (PS00001); at least one predicted glycosaminoglycan attachment site (PS00002); at least one, two, three, and preferably four predicted cAMP- and cGMP-dependent protein kinase phosphorylation sites (PS00004); at least one, two, three, four, five, six, seven, eight, nine, 10, 11, 12, and preferably 13 predicted Protein Kinase C phosphorylation sites (PS00005); at least one, two, three, four, five, six, and preferably seven predicted Casein Kinase II phosphorylation sites (PS00006); at least one, two, three, four, five, six, seven, eight, nine, 10, 11, 12, 13, 14, and preferably 15 predicted N-myristoylation sites (PS00008); and at least one predicted coiled coil domain.

A 33408 family member can include at least one (preferably two, three, four, five, or six) transmembrane domain, at least one (preferably two or three) cytoplasmic domain, at least one (preferably two or three) extracellular domain, at least one P-loop domain, and at least one ion transport protein domain. A 33408 family member can further include a cyclic nucleotide-binding domain. A 33408 family member can further include a PAS domain and a PAC domain. Furthermore, a 33408 family member can include: at least one, two, three, four, five, six, and preferably seven predicted N-glycosylation sites (PS00001); at least one and preferably two predicted cAMP- and cGMP-dependent protein kinase phosphorylation sites (PS00004); at least one, two, three, four, five, six, seven, eight, nine, 10, 11, 12, and preferably 13 predicted Protein Kinase C phosphorylation sites (PS00005); at least one, two, three, four, five, six, seven, eight, nine, 10, 11, 12, 13, 14, 15, and preferably 16 predicted Casein Kinase II phosphorylation sites (PS00006); at least one, two, three, four, five, six, seven, and preferably eight predicted N-myristoylation sites (PS00008); at least one predicted amidation site (PS00009); at least one predicted leucine zipper pattern (PS00029); and at least one predicted coiled coil domain.

A 12189 family member can include at least one (preferably two, three, four, five, or six) transmembrane domain, at least one (preferably two or three) cytoplasmic domain, at least one (preferably two or three) extracellular domain, at least one P-loop domain, and at least one ion transport protein domain. A 12189 family member can further include a potassium channel tetramerisation domain. Furthermore, a 12189 family member can include: at least one and preferably two predicted N-glycosylation sites (PS00001); at least one and preferably two predicted Protein Kinase C phosphorylation sites (PS00005); at least one, two, three, four, and preferably five predicted Casein Kinase II phosphorylation sites (PS00006); at least one predicted tyrosine kinase phosphorylation site (PS00007); at least one, two, three, four, and preferably five predicted N-myristoylation sites (PS00008); and at least one predicted leucine zipper pattern (PS00029).

As the 52906, 33408, or 12189 polypeptides of the invention may modulate 52906, 33408, or 12189-mediated activities, e.g., potassium channel mediated activities, they may be useful as of for developing novel diagnostic and therapeutic agents for 52906, 33408, or 12189-mediated or related disorders, e.g., potassium channel associated disorders, as described below.

As used herein, a "52906, 33408, or 12189 activity", "biological activity of 52906, 33408, or 12189" or "functional activity of 52906, 33408, or 12189", refers to an activity exerted by a 52906, 33408, or 12189 protein, polypeptide or nucleic acid molecule. For example, a 52906, 33408, or 12189 activity can be an activity exerted by 52906, 33408, or 12189 in a physiological milieu on, e.g., a 52906, 33408, or 12189-responsive cell or on a 52906, 33408, or 12189 substrate, e.g., a protein substrate. A 52906, 33408, or 12189 activity can be determined in vivo or in vitro. In one embodiment, a 52906, 33408, or 12189 activity is a direct activity, such as an association with a 52906, 33408, or 12189 target molecule. A "target molecule" or "binding partner" is a molecule with which a 52906, 33408, or 12189 protein binds or interacts in nature. In an exemplary embodiment, 52906, 33408, or 12189 is an ion channel, e.g., a potassium channel.

A 52906, 33408, or 12189 activity can also be an indirect activity, e.g., a cellular signaling activity mediated by interaction of the 52906, 33408, or 12189 protein with a 52906, 33408, or 12189 ligand, e.g., apotassium ion. The features of the 52906, 33408, or 12189 molecules of the present invention can provide similar biological activities as potassium channel family members. For example, the 52906, 33408, or 12189 proteins of the present invention can have one or more of the following activities: (1) interacting with a non-52906, 33408, or 12189 protein molecule; (2) activating a 52906, 33408, or 12189-dependent signal transduction pathway; (3) modulating the release of neurotransmitters; (4) modulating membrane excitability; (5) influencing the resting potential of membranes, wave forms and frequencies of action potentials, and thresholds of excitation; (6) binding a cyclic nucleotide; (7) contributing to the formation of potassium channels; (8) contributing to the formation of calcium-activated, voltage independent potassium channels; (9) modulating repolarization of the neuronal cell membrane; (10) contributing to the formation of voltage-gated potassium channels; (11) contributing to the formation of cyclic nucleotide-gated potassium channels; (12) modulating the flow of $K^+$ ions through a cell membrane; and (13) modulating processes which underlie learning and memory, such as integration of sub-threshold synaptic responses and the conductance of back-propagating action potentials.

Based on the above-described sequence similarities, the 52906, 33408, or 12189 molecules of the present invention are predicted to have similar biological activities as potassium channel family members. In addition, 52906 and 33408 mRNA was found to be highly expressed in cells derived from brain and heart (see Tables 3 and 4). Thus, the 52906, 33408, or 12189 molecules can act as novel diagnostic targets and therapeutic agents for controlling potassium channel associated disorders. Examples of such disorders include neurological disorders and cardiac-related disorders.

As used herein, a "potassium channel associated disorder" includes a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; cellular proliferation, growth, differentiation, or migration, and emotional, intellectual (e.g., learning and memory), or motor processes. Examples of potassium channel associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of potassium channel associated disorders include cardiac-related disorders. Cardiovascular system disorders in which the 52906, 33408, or 12189 molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. 52906, 33408, or 12189-mediated or related disorders also include disorders of the musculoskeletal system such as paralysis and muscle weakness, e.g., ataxia, myotonia, and myokymia.

As used herein, a "potassium channel mediated activity" includes an activity which involves a potassium channel, e.g., a potassium channel in a neuronal cell, a muscle cell, or a thymus cell associated with receiving, conducting, and transmitting signals in, for example, the nervous system. Potassium channel mediated activities include release of neurotransmitters, e.g., dopamine or norepinephrine, from cells, e.g., neuronal cells; modulation of resting potential of membranes, wave forms and frequencies of action potentials, and thresholds of excitation; participation in signal transduction pathways, and modulation of processes such as integration of sub-threshold synaptic responses and the conductance of back-propagating action potentials in, for example, neuronal cells or muscle cells.

The presence of 52906, 33408, or 12189 RNA or protein can be used to identify a cell or tissue, or other biological sample, as being derived from the brain, e.g., cerebral cortex, from the heart, from a muscle, or of neuronal origin. Expression can be determined by evaluating RNA, e.g., by hybridization of a 52906, 33408, or 12189 specific probe, or with a 52906, 33408, or 12189 specific antibody.

The 52906, 33408, or 12189 protein, fragments thereof, and derivatives and other variants of the sequence in SEQ ID NO:2, SEQ ID NO:5, or SEQ ID NO:8 thereof are collectively referred to as "polypeptides or proteins of the invention" or "52906, 33408, or 12189 polypeptides or proteins". Nucleic acid molecules encoding such polypeptides or proteins are collectively referred to as "nucleic acids of the invention" or "52906, 33408, or 12189 nucleic acids." 52906, 33408, or 12189 molecules refer to 52906, 33408, or 12189 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1, SEQ ID NO:3, SEQ ID NO:4, SEQ ID NO:6, or SEQ ID NO:7, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein. As used herein, the terms "gene" and "recombinant gene" refer to nucleic acid molecules which include at least an open reading frame encoding a 52906, 33408, or 12189 protein. The gene can optionally further include non-coding sequences, e.g., regulatory sequences and introns. Preferably, a gene encodes a mammalian 52906, 33408, or 12189 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 52906, 33408, or 12189 protein is at least 10% pure. In a preferred embodiment, the preparation of 52906, 33408, or 12189 protein has less than about 30%, 20%, 10% and more preferably 5% (by dry weight), of non-52906, 33408, or 12189 protein (also referred to herein as a "contaminating protein"), or of chemical precursors or non-52906, 33408, or 12189 chemicals. When the 52906, 33408, or 12189 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 52906, 33408, or 12189 without abolishing or substantially altering a 52906, 33408, or 12189 activity. Preferably the alteration does not substantially alter the 52906, 33408, or 12189 activity, e.g., the activity is at least 20%, 40%, 60%, 70% or 80% of wild-type. An "essential" amino acid residue is a residue that, when altered from the wild-type sequence of 52906, 33408, or 12189, results in abolishing a 52906, 33408, or 12189 activity such that less than 20% of the wild-type activity is present. For example, conserved amino acid residues in 52906, 33408, or 12189 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 52906, 33408, or 12189 protein is preferably replaced with another amino acid residue from the same side chain family. Alternatively, in another embodiment, mutations can be introduced randomly along all or part of a 52906, 33408, or 12189 coding sequence, such as by saturation mutagenesis, and the resultant mutants can be screened for 52906, 33408, or 12189 biological activity to identify mutants that retain activity. Following mutagenesis of SEQ ID NO:1, SEQ ID NO:3, SEQ ID NO:4, SEQ ID NO:6, or SEQ ID NO:7, the encoded protein can be expressed recombinantly and the activity of the protein can be determined.

As used herein, a "biologically active portion" of a 52906, 33408, or 12189 protein includes a fragment of a 52906, 33408, or 12189 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 52906, 33408, or 12189 molecule and a non-52906, 33408, or 12189 molecule or between a first 52906, 33408, or 12189 molecule and a second 52906, 33408, or 12189 molecule (e.g., a dimerization interaction). Biologically active portions of a 52906, 33408, or 12189 protein include peptides comprising amino acid sequences sufficiently homologous to or derived from the amino acid sequence of the 52906, 33408, or 12189 protein, e.g., the amino acid sequence shown in SEQ ID NO:2, SEQ ID NO:5, or SEQ ID NO:8, which include less amino acids than the full length 52906, 33408, or 12189 proteins, and exhibit at least one activity of a 52906, 33408, or 12189 protein. Typically, biologically active portions comprise a domain or motif with at least one activity of the 52906, 33408, or 12189 protein, e.g., the ability to modulate the flow of $K^+$ ions through a cell membrane and/or the ability to modulate the transmission of signals in an electrically excitable cell, e.g., a neuronal cell or a muscle cell. A biologically active portion of a 52906, 33408, or 12189 protein can be a polypeptide which is, for example, 10, 25, 50, 100, 200 or more amino acids in length. Biologically active portions of a 52906, 33408, or 12189 protein can be used as targets for developing agents which modulate a 52906, 33408, or 12189 mediated activity, e.g., the ability to modulate the flow of $K^+$ ions through a cell membrane and/or the ability to modulate the transmission of signals in an electrically excitable cell, e.g., a neuronal cell or a muscle cell.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 52906, 33408, or 12189 nucleic acid molecules of the invention. BLAST protein searches can be performed with the XBLAST program, score=50, wordlength=3 to obtain amino acid sequences homologous to 52906, 33408, or 12189 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See www.ncbi.nlm.nih.gov.

Particularly preferred 52906, 33408, or 12189 polypeptides of the present invention have an amino acid sequence substantially identical to the amino acid sequence of SEQ ID NO:2, SEQ ID NO:5, or SEQ ID NO:8. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%, 91%, 92%, 93%, 94%, 95%, 96%, 97%, 98% or 99% identity to SEQ ID NO:2, SEQ ID NO:5, or SEQ ID NO:8 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%, 91%, 92%, 93%, 94%, 95%, 96%, 97%, 98% or 99% identity to SEQ ID NO:1, SEQ ID NO:3, SEQ ID NO:4, SEQ ID NO:6, or SEQ ID NO:7 are termed substantially identical. "Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. "Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc.

In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 52906, 33408, or 12189 polypeptide described herein, e.g., a full-length 52906, 33408, or 12189 protein or a fragment thereof, e.g., a biologically active portion of 52906, 33408, or 12189 protein. Also included is a nucleic acid fragment suitable for use as a hybridization probe, which can be used, e.g., to identify a nucleic acid molecule encoding a polypeptide of the invention, 52906, 33408, or 12189 a mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, SEQ ID NO:4, or SEQ ID NO:7, or a portion of any of these nucleotide sequences. In one embodiment, the nucleic acid molecule includes sequences encoding the human 52906, 33408, or 12189 protein (i.e., "the coding region" of SEQ ID NO:1, as shown in SEQ ID NO:3 or "the coding region" of SEQ ID NO:4, as shown in SEQ ID NO:6), as well as 5' untranslated sequences. Alternatively, the nucleic acid molecule can include only the coding region of SEQ ID NO:1, SEQ ID NO:4, or SEQ ID NO:7 (e.g., SEQ ID NO:3 or SEQ ID NO:6) and, e.g., no flanking sequences which normally accompany the subject sequence. In another embodiment, the nucleic acid molecule encodes a sequence corresponding to a fragment of the protein from about amino acids 472–661 of SEQ ID NO:2, amino acids 247–467 of SEQ ID NO:5, amino acids 565–655 of SEQ ID NO:5, amino acids 3–101 of SEQ ID NO:8, or amino acids 198–383 of SEQ ID NO:8.

In another embodiment, an isolated nucleic acid molecule of the invention includes a nucleic acid molecule which is a complement of the nucleotide sequence shown in SEQ ID NO:1, SEQ ID NO:3, SEQ ID NO:4, SEQ ID NO:6, or SEQ ID NO:7, or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:4, SEQ ID NO:6, or SEQ ID NO:7, such that it can hybridize (e.g., under a stringency condition described herein) to the nucleotide sequence shown in SEQ ID NO:1, SEQ ID NO:3, SEQ ID NO:4, SEQ ID NO:6, or SEQ ID NO:7, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, SEQ ID NO:3, SEQ ID NO:4, SEQ ID NO:6, or SEQ ID NO:7, or a portion, preferably of the same length, of any of these nucleotide sequences.

52906, 33408, or 12189 Nucleic Acid Fragments

A nucleic acid molecule of the invention can include only a portion of the nucleic acid sequence of SEQ ID NO:1, SEQ ID NO:3, SEQ ID NO:4, SEQ ID NO:6, or SEQ ID NO:7. For example, such a nucleic acid molecule can include a fragment which can be used as a probe or primer or a fragment encoding a portion of a 52906, 33408, or 12189 protein, e.g., an immunogenic or biologically active portion of a 52906, 33408, or 12189 protein. A fragment can comprise those nucleotides of SEQ ID NO:1, SEQ ID NO:3, SEQ ID NO:4, SEQ ID NO:6, or SEQ ID NO:7, which encode an ion transport protein domain of human 52906, 33408, or 12189. The nucleotide sequence determined from the cloning of the 52906, 33408, or 12189 gene allows for the generation of probes and primers designed for use in identifying and/or cloning other 52906, 33408, or 12189) family members, or fragments thereof, as well as 52906, 33408, or 12189 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein (e.g., an ion transport protein domain, a cyclic nucleotide-binding domain, a potassium channel tetramerisation domain, a transmembrane domain, a cytoplasmic domain, an extracellular domain, a Pore-loop domain, or a PAS domain) or fragments thereof, particularly fragments thereof which are at least 100, 200, 300, 400, or 500 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 52906, 33408, or 12189 nucleic acid fragment can include a sequence corresponding to an ion transport protein domain, a cyclic nucleotide-binding domain, a potassium channel tetramerisation domain, a transmembrane domain, a cytoplasmic domain, an extracellular domain, a Pore-loop domain, or a PAS domain.

52906, 33408, or 12189 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, SEQ ID NO:4, SEQ ID NO:6, or SEQ ID NO:7, or of a naturally occurring allelic variant or mutant of SEQ ID NO:1, SEQ ID NO:3, SEQ ID NO:4, SEQ ID NO:6, or SEQ ID NO:7.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an ion transport protein domain, a cyclic nucleotide-binding domain, a potassium channel tetramerisation domain, a transmembrane domain, a cytoplasmic domain, an extracellular domain, a Pore-loop domain, or a PAS domain. The locations of these domains in SEQ ID NO:2, SEQ ID NO:5, and SEQ ID NO:8 are described in Table 2.

In another embodiment a set of primers is provided, e.g., primers suitable for use in a PCR, which can be used to amplify a selected region of a 52906, 33408, or 12189 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an ion transport protein domain, a cyclic nucleotide-binding domain, a potassium channel tetramerisation domain, a transmembrane domain, a cytoplasmic domain, an extracellular domain, a Pore-loop domain, or a PAS domain.

A nucleic acid fragment can encode an epitope bearing region of a polypeptide described herein.

A nucleic acid fragment encoding a "biologically active portion of a 52906, 33408, or 12189 polypeptide" can be prepared by isolating a portion of the nucleotide sequence of SEQ ID NO:1, SEQ ID NO:3, SEQ ID NO:4, SEQ ID NO:6, or SEQ ID NO:7, which encodes a polypeptide having a 52906, 33408, or 12189 biological activity (e.g., the biological activities of the 52906, 33408, or 12189 proteins are described herein), expressing the encoded portion of the 52906, 33408, or 12189 protein (e.g., by recombinant expression in vitro) and assessing the activity of the encoded portion of the 52906, 33408, or 12189 protein. For example, a nucleic acid fragment encoding a biologically active portion of 52906, 33408, or 12189 includes ion transport protein domain, e.g., amino acids 472–661 of SEQ ID NO:2, amino acids 247–467 of SEQ ID NO:5, or amino acids 198–383 of SEQ ID NO:8. A nucleic acid fragment encoding a biologically active portion of a 52906, 33408, or 12189 polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 2000, 2500, 3000, 3300, 3400, 3500, or more nucleotides in length and hybridizes under a stringency condition described herein to a nucleic acid molecule of SEQ ID NO:1, SEQ ID NO:3, SEQ ID NO:4, SEQ ID NO:6, or SEQ ID NO:7.

In preferred embodiments, the fragment includes at least one, and preferably at least 5, 10, 15, 25, 50, 100, 200, 300, 400, or 500 nucleotides from nucleotides 1–2962, 3437–3525, 1–1441, 3182–3525, or 1–2687 of SEQ ID NO:1.

In preferred embodiments, the fragment includes at least one, and preferably at least 5, 10, 15, 25, 50, 75, 100, 200, 300, 500, 1000, or 1500 nucleotides encoding a protein including 5, 10, 15, 20, 25, 30, 40, 50, 100, 200, 300, 400, or 500 amino acids from amino acids 1–775, 1–268, 1–683 of SEQ ID NO:2.

In preferred embodiments, the nucleic acid fragment includes a nucleotide sequence that is other than the sequence of AA418096, V35457, Z51630, W63707, or W63702.

In preferred embodiments, the fragment comprises the coding region of 52906, e.g., the nucleotide sequence of SEQ ID NO:3.

In preferred embodiments, the fragment includes at least one, and preferably at least 5, 10, 15, 25, 50, 100, 200, 300, 400, or 500 nucleotides from nucleotides 1–1844, 1–277, 1–252, or 3245–3553, of SEQ ID NO:4.

In preferred embodiments, the fragment includes the nucleotide sequence of SEQ ID NO:6 and at least one, and preferably at least 5, 10, 15, 25, 50, 75, 100, 200, 300, or 500 nucleotides, e.g., consecutive nucleotides, of SEQ ID NO:4.

In preferred embodiments, the fragment includes at least one, and preferably at least 5, 10, 15, 25, 50, 75, 100, 200, 300, 500, 1000, or 1500 nucleotides encoding a protein including 5, 10, 15, 20, 25, 30, 40, 50, 100, 200, 300, 400, or 500 amino acids from amino acids 1–522 of SEQ ID NO:5.

In preferred embodiments, the nucleic acid fragment includes a nucleotide sequence that is other than the sequence of U69185 or a sequence described in WO01/04133 or WO01/29068.

In preferred embodiments, the fragment comprises the coding region of 33408, e.g., the nucleotide sequence of SEQ ID NO:6.

52906, 33408, or 12189 Nucleic Acid Variants

The invention further encompasses nucleic acid molecules that differ from the nucleotide sequence shown in SEQ ID NO:1, SEQ ID NO:3, SEQ ID NO:4, SEQ ID NO:6, or SEQ ID NO:7. Such differences can be due to degeneracy of the genetic code (and result in a nucleic acid which encodes the same 52906, 33408, or 12189 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, SEQ ID NO:5, or SEQ ID NO:8. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, SEQ ID NO:4, SEQ ID NO:6, or SEQ ID NO:7, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2, SEQ ID NO:5, or SEQ ID NO:8 or a fragment of this sequence. Such nucleic acid molecules can readily be identified as being able to hybridize under a stringency condition described herein, to the nucleotide sequence shown in SEQ ID NO:2, SEQ ID NO:5, or SEQ ID NO:8 or a fragment of the sequence. Nucleic acid molecules corresponding to orthologs, homologs, and allelic variants of the 52906, 33408, or 12189 cDNAs of the invention can further be isolated by mapping to the same chromosome or locus as the 52906, 33408, or 12189 gene.

Preferred variants include those that are correlated with the ability to modulate the flow of $K^+$ ions through a cell membrane and/or the ability to modulate the transmission of signals in an electrically excitable cell, e.g., a neuronal cell or a muscle cell.

Allelic variants of 52906, 33408, or 12189, e.g., human 52906, 33408, or 12189, include both functional and non-functional proteins. Functional allelic variants are naturally occurring amino acid sequence variants of the 52906, 33408, or 12189 protein within a population that maintain the ability to modulate the flow of $K^+$ ions through a cell membrane and/or the ability to modulate the transmission of signals in an electrically excitable cell, e.g., a neuronal cell or a muscle cell. Functional allelic variants will typically contain only conservative substitution of one or more amino acids of SEQ ID NO:2, SEQ ID NO:5, or SEQ ID NO:8, or substitution, deletion or insertion of non-critical residues in non-critical regions of the protein. Non-functional allelic variants are naturally-occurring amino acid sequence variants of the 52906, 33408, or 12189, e.g., human 52906, 33408, or 12189, protein within a population that do not have the ability to modulate the flow of $K^+$ ions through a cell membrane and/or the ability to modulate the transmission of signals in an electrically excitable cell, e.g., a neuronal cell or a muscle cell. Non-functional allelic variants will typically contain a non-conservative substitution, a deletion, or insertion, or premature truncation of the amino acid sequence of SEQ ID NO:2, SEQ ID NO:5, or SEQ ID NO:8, or a substitution, insertion, or deletion in critical residues or critical regions of the protein.

Moreover, nucleic acid molecules encoding other 52906, 33408, or 12189 family members and, thus, which have a nucleotide sequence which differs from the 52906, 33408, or 12189 sequences of SEQ ID NO:1, SEQ ID NO:3, SEQ ID NO:4, SEQ ID NO:6, or SEQ ID NO:7 are intended to be within the scope of the invention.

Antisense Nucleic Acid Molecules, Ribozymes and Modified 52906, 33408, or 12189 Nucleic Acid Molecules In another aspect, the invention features, an isolated nucleic acid molecule which is antisense to 52906, 33408, or 12189. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 52906, 33408, or 12189 coding strand, or to only a portion thereof (e.g., the coding region of human 52906, 33408, or 12189 corresponding to SEQ ID NO:3 or SEQ ID NO:6). In another embodiment, the antisense nucleic acid molecule is antisense to a "noncoding region" of the coding strand of a nucleotide sequence encoding 52906, 33408, or 12189 (e.g., the 5' and 3' untranslated regions).

An antisense nucleic acid can be designed such that it is complementary to the entire coding region of 52906, 33408, or 12189 mRNA, but more preferably is an oligonucleotide which is antisense to only a portion of the coding or noncoding region of 52906, 33408, or 12189 mRNA. For example, the antisense oligonucleotide can be complementary to the region surrounding the translation start site of 52906, 33408, or 12189 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 52906, 33408, or 12189 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense a nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res*. 15:6131–6148) or a chimeric RNA-DNA analogue (Inoue et al. (1987) *FEBS Lett*. 215:327–330).

In still another embodiment, an antisense nucleic acid of the invention is a ribozyme. A ribozyme having specificity for a 52906, 33408, or 12189-encoding nucleic acid can include one or more sequences complementary to the nucleotide sequence of a 52906, 33408, or 12189 cDNA disclosed herein (i.e., SEQ ID NO:1, SEQ ID NO:3, SEQ ID NO:4, SEQ ID NO:6, or SEQ ID NO:7), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 52906, 33408, or 12189-encoding mRNA. See, e.g., Cech et al. U.S. Pat. No. 4,987,071; and Cech et al. U.S. Pat. No. 5,116,742. Alternatively, 52906, 33408, or 12189 mRNA can be used to select a catalytic RNA having a specific ribonuclease activity from a pool of RNA molecules. See, e.g., Bartel, D. and Szostak, J. W. (1993) *Science* 261:1411–1418. 52906, 33408, or 12189 gene expression can be inhibited by targeting nucleotide sequences complementary to the regulatory region of the 52906, 33408, or 12189 (e.g., the 52906, 33408, or 12189 promoter and/or enhancers) to form triple helical structures that prevent transcription of the 52906, 33408, or 12189 gene in target cells. See generally, Helene, C. (1991) *Anticancer Drug Des*. 6:569–84; Helene, C. i (1992) *Ann. N.Y. Acad. Sci*. 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 52906, 33408, or 12189 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech*. 19:17 and Faria et al. (2001) *Nature Biotech*. 19:40–44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4:5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci*. 93: 14670–675.

PNAs of 52906, 33408, or 12189 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 52906, 33408, or 12189 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 52906, 33408, or 12189 nucleic acid of the invention, two complementary regions one having a fluorophore and one a quencher such that the molecular beacon is useful for quantitating the presence of the 52906, 33408, or 12189 nucleic acid of the invention in a sample. Molecular beacon nucleic acids are described, for example, in Lizardi et al, U.S. Pat. No. 5,854,033; Nazarenko et al., U.S. Pat. No. 5,866,336, and Livak et al., U.S. Pat. 5,876,930.

Isolated 52906, 33408, or 12189 Polypeptides

In another aspect, the invention features, an isolated 52906, 33408, or 12189 protein, or fragment, e.g., a biologically active portion, for use as immunogens or antigens to raise or test (or more generally to bind) anti-52906, 33408, or 12189 antibodies. 52906, 33408, or 12189 protein can be isolated from cells or tissue sources using standard protein purification techniques. 52906, 33408, or 12189 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 52906, 33408, or 12189 polypeptide has one or more of the following characteristics:

(i) it has the ability to modulate the flow of $K^+$ ions through a cell membrane, e.g., to allow for the flow of $K^+$ ions in and/or out of a cell under certain conditions;

(ii) it has the ability to modulate the transmission of signals in an electrically excitable cell, e.g., a neuronal cell or a muscle cell;

(iii) it has a molecular weight, e.g., a deduced molecular weight, preferably ignoring any contribution of post translational modifications, amino acid composition or other physical characteristic of a 52906, 33408, or 12189 polypeptide, e.g., a polypeptide of SEQ ID NO:2, SEQ ID NO:5, or SEQ ID NO:8;

(iv) it has an overall sequence similarity of at least 60%, more preferably at least 70, 80, 90, or 95%, with a polypeptide a of SEQ ID NO:2, SEQ ID NO:5, or SEQ ID NO:8;

(v) it can be found in neuronal cells or muscle cells (e.g., heart cells);

(vi) it has the ability to modulate the resting potential of membranes;

(vii) it has a P-loop domain which is preferably about 70%, 80%, 90% or 95% similar with amino acids 616–639 of SEQ ID NO:2, amino acids 420–440 of SEQ ID NO:5, or amino acids 339–355 of SEQ ID NO:8;

(viii) it has an ion transport protein domain which is preferably about 70%, 80%, 90% or 95% similar with amino acids 472–661 of SEQ ID NO:2, amino acids 247–467 of SEQ ID NO:5, or amino acids 198–383 of SEQ ID NO:8;

(ix) it has a cyclic nucleotide-binding domain which is preferably about 70%, 80%, 90% or 95% similar with amino acids 565–655 of SEQ ID NO:5;

(x) it has a potassium channel tetramerisation domain which is preferably about 70%, 80%, 90% or 95% similar with amino acids 3–101 of SEQ ID NO:8; or (xi) it has least 70%, preferably 80%, and most preferably 90% of the cysteines found amino acid sequence of the native protein.

In a preferred embodiment the 52906, 33408, or 12189 protein, or fragment thereof, differs from the corresponding sequence in SEQ ID NO:2, SEQ ID NO:5, or SEQ ID NO:8. In one embodiment it differs by at least one but by less than 15, 10 or 5 amino acid residues. In another it differs from the corresponding sequence in SEQ ID NO:2, SEQ ID NO:5, or SEQ ID NO:8 by at least one residue but less than 20%, 15%, 10% or 5% of the residues in it differ from the corresponding sequence in SEQ ID NO:2, SEQ ID NO:5, or SEQ ID NO:8. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the ion transport protein domain. In another preferred embodiment one or more differences are in the ion transport protein domain.

Other embodiments include a protein that contain one or more changes in amino acid sequence, e.g., a change in an amino acid residue which is not essential for activity. Such 52906, 33408, or 12189 proteins differ in amino acid sequence from SEQ ID NO:2, SEQ ID NO:5, or SEQ ID NO:8, yet retain biological activity.

In one embodiment, the protein includes an amino acid sequence at least about 60%, 65%, 70%, 75%, 80%, 85%, 90%, 95%, 98% or more homologous to SEQ ID NO:2, SEQ ID NO:5, or SEQ ID NO:8.

A 52906 protein or fragment is provided which varies from the sequence of SEQ ID NO:2 in regions defined by amino acids about 1–471 and/or 662–847 by at least one but by less than 15, 10 or 5 amino acid residues in the protein or fragment but which does not differ from SEQ ID NO:2 in regions defined by amino acids about 472–661. A 33408 protein or fragment is provided which varies from the sequence of SEQ ID NO:5 in regions defined by amino acids about 1–246 and/or 468–988 by at least one but by less than 15, 10 or 5 amino acid residues in the protein or fragment but which does not differ from SEQ ID NO:2 in regions defined by amino acids about 247–467. A 12189 protein or fragment is provided which varies from the sequence of SEQ ID NO:8 in regions defined by amino acids about 1–197 and/or 384–446 by at least one but by less than 15, 10 or 5 amino acid residues in the protein or fragment but which does not differ from SEQ ID NO:2 in regions defined by amino acids about 198–383. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 52906, 33408, or 12189 protein includes an ion transport protein domain, a cyclic nucleotide-binding domain, a potassium channel tetramerisation domain, a transmembrane domain, a cytoplasmic domain, an extracellular domain, a Pore-loop domain, or a PAS domain. Moreover, other biologically active portions, in which other regions of the protein are deleted, can be prepared by recombinant techniques and evaluated for one or more of the functional activities of a native 52906, 33408, or 12189 protein.

In a preferred embodiment, the 52906, 33408, or 12189 protein has an amino acid sequence shown in SEQ ID NO:2, SEQ ID NO:5, or SEQ ID NO:8. In other embodiments, the 52906, 33408, or 12189 protein is substantially identical to SEQ ID NO:2, SEQ ID NO:5, or SEQ ID NO:8. In yet another embodiment, the 52906, 33408, or 12189 protein is substantially identical to SEQ ID NO:2, SEQ ID NO:5, or SEQ ID NO:8 and retains the functional activity of the protein of SEQ ID NO:2, SEQ ID NO:5, or SEQ ID NO:8, as described in detail in the subsections above.

52906, 33408 or 12189 Chimeric or Fusion Proteins

In another aspect, the invention provides 52906, 33408, or 12189 chimeric or fusion proteins. As used herein, a 52906, 33408, or 12189 "chimeric protein" or "fusion protein" includes a 52906, 33408, or 12189 polypeptide linked to a non-52906, 33408, or 12189 polypeptide. A "non-52906, 33408, or 12189 polypeptide" refers to a polypeptide having an amino acid sequence corresponding to a protein which is not substantially homologous to the 52906, 33408, or 12189 protein, e.g., a protein which is different from the 52906, 33408, or 12189 protein and which is derived from the same or a different organism. The 52906, 33408, or 12189 polypeptide of the fusion protein can correspond to all or a portion e.g., a fragment described herein of a 52906, 33408, or 12189 amino acid sequence. In a preferred embodiment, a 52906, 33408, or 12189 fusion protein includes at least one (or two) biologically active portion of a 52906, 33408, or 12189 protein. The non-52906, 33408, or 12189 polypeptide can be fused to the N-terminus or C-terminus of the 52906, 33408, or 12189 polypeptide.

The fusion protein can include a moiety which has a high affinity for a ligand. For example, the fusion protein can be a GST-52906, 33408, or 12189 fusion protein in which the 52906, 33408, or 12189 sequences are fused to the C-terminus of the GST sequences. Such fusion proteins can facilitate the purification of recombinant 52906, 33408, or 12189. Alternatively, the fusion protein can be a 52906, 33408, or 12189 protein containing a heterologous signal sequence at its N-terminus. In certain host cells (e.g., mammalian host cells), expression and/or secretion of 52906, 33408, or 12189 can be increased through use of a heterologous signal sequence.

Fusion proteins can include all or a part of a serum protein, e.g., an IgG constant region, or human serum albumin.

The 52906, 33408, or 12189 fusion proteins of the invention can be incorporated into pharmaceutical compositions and administered to a subject in vivo. The 52906, 33408, or 12189 fusion proteins can be used to affect the bioavailability of a 52906, 33408, or 12189 substrate. 52906, 33408, or 12189 fusion proteins may be useful therapeutically for the treatment of disorders caused by, for example, (i) aberrant modification or mutation of a gene encoding a 52906, 33408, or 12189 protein; (ii) mis-regulation of the 52906, 33408, or 12189 gene; and (iii) aberrant post-translational modification of a 52906, 33408, or 12189 protein.

Moreover, the 52906, 33408, or 12189-fusion proteins of the invention can be used as immunogens to produce anti-52906, 33408, or 12189 antibodies in a subject, to purify 52906, 33408, or 12189 ligands and in screening assays to identify molecules which inhibit the interaction of 52906, 33408, or 12189 with a 52906, 33408, or 12189 substrate.

Expression vectors are commercially available that already encode a fusion moiety (e.g., a GST polypeptide). A 52906, 33408, or 12189-encoding nucleic acid can be cloned into such an expression vector such that the fusion moiety is linked in-frame to the 52906, 33408, or 12189 protein.

Variants of 52906, 33408, or 12189 Proteins

In another aspect, the invention also features a variant of a 52906, 33408, or 12189 polypeptide, e.g., which functions as an agonist (mimetics) or as an antagonist. Variants of the 52906, 33408, or 12189 proteins can be generated by mutagenesis, e.g., discrete point mutation, the insertion or deletion of sequences or the truncation of a 52906, 33408, or 12189 protein. An agonist of the 52906, 33408, or 12189 proteins can retain substantially the same, or a subset, of the biological activities of the naturally occurring form of a 52906, 33408, or 12189 protein. An antagonist of a 52906, 33408, or 12189 protein can inhibit one or more of the activities of the naturally occurring form of the 52906, 33408, or 12189 protein by, for example, competitively modulating a 52906, 33408, or 12189-mediated activity of a 52906, 33408, or 12189 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 52906, 33408, or 12189 protein.

Variants of a 52906, 33408, or 12189 protein can be identified by screening combinatorial libraries of mutants, e.g., truncation mutants, of a 52906, 33408, or 12189 protein for agonist or antagonist activity.

Libraries of fragments e.g., N terminal, C terminal, or internal fragments, of a 52906, 33408, or 12189 protein coding sequence can be used to generate a variegated population of fragments for screening and subsequent selection of variants of a 52906, 33408, or 12189 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 52906, 33408, or 12189 proteins. Recursive ensemble mutagenesis (REM), a new technique which enhances the frequency of functional mutants in the libraries, can be used in combination with the screening assays to identify 52906, 33408, or 12189 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 52906, 33408, or 12189 library. For example, a library of expression vectors can be transfected into a cell line, e.g., a cell line, which ordinarily responds to 52906, 33408, or 12189 in a substrate-dependent manner. The transfected cells are then contacted with 52906, 33408, or 12189 and the effect of the expression of the mutant on signaling by the 52906, 33408, or 2189 substrate can be detected, e.g., by measuring potassium channel activity, e.g., ion flux through a potassium channel. Plasmid DNA can then be recovered from the cells which score for inhibition, or alternatively, potentiation of signaling by the 52906, 33408, or 12189 substrate, and the individual clones further characterized.

In another aspect, the invention features a method of making a 52906, 33408, or 12189 polypeptide, e.g., a peptide having a non-wild type activity, e.g., an antagonist, agonist, or super agonist of a naturally occurring 52906, 33408, or 12189 polypeptide, e.g., a naturally occurring 52906, 33408, or 12189 polypeptide. The method includes: altering the sequence of a 52906, 33408, or 12189 polypeptide, e.g., altering the sequence e.g., by substitution or deletion of one or more residues of a non-conserved region, a domain or residue disclosed herein, and testing the altered polypeptide for the desired activity.

In another aspect, the invention features a method of making a fragment or analog of a 52906, 33408, or 12189 polypeptide a biological activity of a naturally occurring 52906, 33408, or 12189 polypeptide. The method includes: altering the sequence, e.g., by substitution or deletion of one or more residues, of a 52906, 33408, or 12189 polypeptide, e.g., altering the sequence of a non-conserved region, or a domain or residue described herein, and testing the altered polypeptide for the desired activity.

Anti-52906 33408, or 12189 Antibodies

In another aspect, the invention provides an anti-52906, 33408, or 12189 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-52906, 33408, or 12189 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 52906, 3340, or 12189 polypeptide or fragment thereof. Examples of antigen-binding fragments of the anti-52906, 33408, or 12189 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 24:423–426; and Huston et al. (1988) Proc. Natl. Acad. Sci. USA 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-52906, 33408, or 12189 antibody can be a polyclonal or a monoclonal antibody. In other embodiments, the antibody can be recombinantly produced, e.g., produced by phage display or by combinatorial methods.

Phage display and combinatorial methods for generating anti-52906, 33408, or 12189 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370–1372; Hay et al. (1992) Hum Antibod Hybridomas 3:81–85; Huse et al. (1989) Science 246:1275–1281; Griffths et al. (1993) EMBO J 12:725–734; Hawkins et al. (1992) J Mol Biol 226:889–896; Clackson et al. (1991) Nature 352:624–628; Gram et al. (1992) PNAS 89:3576–3580; Garrad et al. (1991) Bio/Technology 9:1373–1377; Hoogenboom et al. (1991) Nuc Acid Res 19:4133–4137; and Barbas et al. (1991) PNAS 88:7978–7982, the contents of all of which are incorporated by reference herein).

In one embodiment, the anti-52906, 33408, or 12189 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art. Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856–859; Green, L. L. et al. 1994 Nature Genet. 7:13–21; Morrison, S. L. et al. 1994 Proc. Natl. Acad. Sci. USA 81:6851–6855; Bruggeman et al. 1993 Year Immunol 7:33–40; Tuaillon et al. 1993 PNAS 90:3720–3724; Bruggeman et al. 1991 Eur J Immunol 21:1323–1326).

An anti-52906, 33408, or 12189 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559).

A humanized or CDR-grafted antibody will have at least one or two but generally all three recipient CDR's (of heavy and or light imuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 52906, 33408, or 12189 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 52906, 33408, or 12189 polypeptide or fragment thereof. The recombinant DNA encoding the humanized antibody, or fragment thereof, can then be cloned into an appropriate expression vector. Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amimo acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585, 089, the contents of which are hereby incorporated by reference. Other techniques for humanizing antibodies are described in Padlan et al. EP 519596 A1, published on Dec. 23, 1992.

In preferred embodiments an antibody can be made by immunizing with puified 52906, 33408, or 12189 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 52906, 33408, or 12189 protein or, antigenic peptide fragment of 52906, 33408, or 12189 can be used as an immunogen or can be used to identify anti-52906, 33408, or 12189 antibodies made with other immunogens, e.g., cells, membrane preparations, and the like. The antigenic peptide of 52906, 33408, or 12189 should include at least 8 amino acid residues of the amino acid sequence shown in SEQ ID NO:2, SEQ ID NO:5, or SEQ ID NO:8 and encompasses an epitope of 52906, 33408, or 12189. Preferably, the antigenic peptide includes at least 10 amino acid residues, more preferably at least 15 amino acid residues, even more preferably at least 20 amino acid residues, and most preferably at least 30 amino acid residues.

Fragments of 52906, 33408, or 12189 which include residues about 241–265 of SEQ ID NO:2, 710–740 of SEQ ID NO:5, or 35–55 of SEQ ID NO:8 can be used to make, e.g., used as immunogens or used to characterize the specificity of an antibody, antibodies against hydrophilic regions of the 52906, 33408, or 12189 protein. Similarly, fragments of 52906, 33408, or 12189 which include residues about 785–800 of SEQ ID NO:2, 585–600 of SEQ ID NO:5, or 75–95 of SEQ ID NO:8 can be used to make an antibody against a hydrophobic region of the 52906, 33408, or 12189 protein. Fragments of 52906, 33408, or 12189 which include residues 420–432 of SEQ ID NO:2, 237–244 of SEQ ID NO:5, or 153–199 of SEQ ID NO:8 can be used to make an antibody against an extracellular region of the 52906, 33408, or 12189 protein. Fragments of 52906, 33408, or 12189 which include residues 1–401 of SEQ ID NO:2, 1–218 of SEQ ID NO:5, or 1–133 of SEQ ID NO:8 can be used to make an antibody against an intracellular region of the 52906, 33408, or 12189 protein. Fragments of 52906, 33408, or 12189 which include residues 616–639 of SEQ ID NO:2, 420–440 of SEQ ID NO:5, or 339–355 of SEQ ID NO:8 can be used to make an antibody against the P-loop region of the 52906, 33408, or 12189 protein. Fragments of 52906, 33408, or 12189 which include amino acids 472–661 of SEQ ID NO:2, amino acids 247–467 of SEQ ID NO:5, or amino acids 198–383 of SEQ ID NO:8 can be used to make an antibody against the ion transport protein domain of the 52906, 33408, or 12189 protein. Fragments of 33408 which include amino acids 565–655 of SEQ ID NO:5 can be used to make an antibody against the cyclic nucleotide-binding domain of the 33408 protein. Fragments of 12189 which include amino acids 3–101 of SEQ ID NO:8 can be used to make an antibody against the potassium channel tetramerisation domain of the 12189 protein.

Antibodies reactive with, or specific for, any of these regions, or other regions or domains described herein are provided.

Antibodies which bind only native 52906, 33408, or 12189 protein, only denatured or otherwise non-native 52906, 33408, or 12189 protein, or which bind both, are within the invention. Antibodies with linear or conformational epitopes are within the invention. Conformational epitopes can sometimes be identified by identifying antibodies which bind to native but not denatured 52906, 33408, or 12189 protein.

Preferred epitopes encompassed by the antigenic peptide are regions of 52906, 33408, or 12189 are located on the surface of the protein, e.g., hydrophilic regions, as well as regions with high antigenicity. For example, an Emini surface probability analysis of the human 52906, 33408, or 12189 protein sequence can be used to indicate the regions that have a particularly high probability of being localized to the surface of the 52906, 33408, or 12189 protein and are thus likely to constitute surface residues useful for targeting antibody production.

In a preferred embodiment the antibody can bind to the extracellular portion of the 52906, 33408, or 12189 protein, e.g., it can bind to a whole cell which expresses the 52906, 33408, or 12189 protein. In another embodiment, the antibody binds an intracellular portion of the 52906, 33408, or 12189 protein.

In preferred embodiments antibodies can bind one or more of purified antigen, membrane associated antigen, tissue, e.g., tissue sections, whole cells, preferably living cells, lysed cells, cell fractions, e.g., membrane fractions.

The anti-52906, 33408, or 12189 antibody can be a single chain antibody. A single-chain antibody (scFV) may be engineered (see, for example, Colcher, D. et al. (1999) *Ann N Y Acad Sci* 880:263–80; and Reiter, Y. (1996) *Clin Cancer Res* 2:245–52). The single chain antibody can be dimerized or multimerized to generate multivalent antibodies having specificities for different epitopes of the same target 52906, 33408, or 12189 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

In a preferred embodiment, an anti-52906, 33408, or 12189 antibody alters (e.g., increases or decreases) an activity of a 52906, 33408, or 12189 polypeptide, e.g., the ability to modulate the flow of $K^+$ ions through a cell membrane and/or the ability to modulate the transmission of signals in an electrically excitable cell, e.g., a neuronal cell or a muscle cell. For example, the antibody can bind at or in proximity to a Pore loop domain, e.g., to an epitope that includes a residue located from about 616–639 of SEQ ID NO:2, 420–440 of SEQ ID NO:5, or 339–355 of SEQ ID NO:8.

The antibody can be coupled to a toxin, e.g., a polypeptide toxin, e.g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-52906, 33408, or 12189 antibody (e.g., monoclonal antibody) can be used to isolate 52906, 33408, or 12189 by standard techniques, such as affinity chromatography or immunoprecipitation. Moreover, an anti-52906, 33408, or 12189 antibody can be used to detect 52906, 33408, or 12189 protein (e.g., in a cellular lysate or cell supernatant) in order to evaluate the abundance and pattern of expression of the protein. Anti-52906, 33408, or 12189 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin;

examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-52906, 33408, or 12189 antibody, e.g., an anti-52906, 33408, or 12189 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-52906, 33408, or 12189 antibody, e.g., and antibody described herein, and method of using said cells to make a 52906, 33408, or 12189 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 52906, 33408, or 12189 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 52906, 33408, or 12189 proteins, mutant forms of 52906, 33408, or 12189 proteins, fusion proteins, and the like).

The recombinant expression vectors of the invention can be designed for expression of 52906, 33408, or 12189 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 52906, 33408, or 12189 activity assays, (e.g., direct assays or competitive assays described in detail below), or to generate antibodies specific for 52906, 33408, or 12189 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res*. 20:2111–2118). Such alteration of nucleic acid sequences of the invention can be carried out by standard DNA synthesis techniques.

The 52906, 33408, or 12189 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev*. 1:268–277), lymphoid-specific promoters (Calame and Eaton (1988) *Adv. Immunol*. 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA*

86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 52906, 33408, or 12189 nucleic acid molecule within a recombinant expression vector or a 52906, 33408, or 12189 nucleic acid molecule containing sequences which allow it to homologously recombine into a specific site of the host cellos genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 52906, 33408, or 12189 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell* 23:175–182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 52906, 33408, or 12189 protein. Accordingly, the invention further provides methods for producing a 52906, 33408, or 12189 protein using the host cells of the invention. In one embodiment, the method includes culturing the host cell of the invention (into which a recombinant expression vector encoding a 52906, 33408, or 12189 protein has been introduced) in a suitable medium such that a 52906, 33408, or 12189 protein is produced. In another embodiment, the method further includes isolating a 52906, 33408, or 12189 protein from the medium or the host cell.

In another aspect, the invention features, a cell or purified preparation of cells which include a 52906, 33408, or 12189 transgene, or which otherwise misexpress 52906, 33408, or 12189. The cell preparation can consist of human or non-human cells, e.g., rodent cells, e.g., mouse or rat cells, rabbit cells, or pig cells. In preferred embodiments, the cell or cells include a 52906, 33408, or 12189 transgene, e.g., a heterologous form of a 52906, 33408, or 12189, e.g., a gene derived from humans (in the case of a non-human cell). The 52906, 33408, or 12189 transgene can be misexpressed, e.g., overexpressed or underexpressed. In other preferred embodiments, the cell or cells include a gene that misexpresses an endogenous 52906, 33408, or 12189, e.g., a gene the expression of which is disrupted, e.g., a knockout. Such cells can serve as a model for studying disorders that are related to mutated or mis-expressed 52906, 33408, or 12189 alleles or for use in drug screening.

In another aspect, the invention features, a human cell, e.g., a neuronal cell or a muscle cell, transformed with nucleic acid which encodes a subject 52906, 33408, or 12189 polypeptide.

Also provided are cells, preferably human cells, e.g., a neuronal cell, a muscle cell, a hematopoietic cell, or a fibroblast cell, in which an endogenous 52906, 33408, or 12189 is under the control of a regulatory sequence that does not normally control the expression of the endogenous 52906, 33408, or 12189 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 52906, 33408, or 12189 gene. For example, an endogenous 52906, 33408, or 12189 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 52906, 33408, or 12189 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 52906, 33408, or 12189 polypeptide can be regulated in the subject by administering an agent (e.g., a steroid hormone) to the subject. In another preferred embodiment, the implanted recombinant cells express and secrete an antibody specific for a 52906, 33408, or 12189 polypeptide. The antibody can be any antibody or any antibody derivative described herein.

Transgenic Animals

The invention provides non-human transgenic animals. Such animals are useful for studying the function and/or activity of a 52906, 33408, or 12189 protein and for identifying and/or evaluating modulators of 52906, 33408, or 12189 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 52906, 33408, or 12189 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 52906, 33408, or 12189 protein to particular cells. A transgenic founder animal can be identified based upon the presence of a 52906, 33408, or 12189 transgene in its genome and/or expression of 52906, 33408, or 12189 mRNA in tissues or cells of the animals. A transgenic founder animal can then be used to breed additional animals carrying the transgene. Moreover, transgenic animals carrying a transgene encoding a 52906, 33408, or 12189 protein can further be bred to other transgenic animals carrying other transgenes.

52906, 33408, or 12189 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and phamacogenetics); and c) methods of treatment (e.g., therapeutic and prophylactic).

The isolated nucleic acid molecules of the invention can be used, for example, to express a 52906, 33408, or 12189 protein (e.g., via a recombinant expression vector in a host cell in gene therapy applications), to detect a 52906, 33408, or 12189 mRNA (e.g., in a biological sample) or a genetic alteration in a 52906, 33408, or 12189 gene, and to modulate 52906, 33408, or 12189 activity, as described further below. The 52906, 33408, or 12189 proteins can be used to treat disorders characterized by insufficient or excessive production of a 52906, 33408, or 12189 substrate or production of 52906 33408, or 12189 inhibitors. In addition, the 52906, 33408, or 12189 proteins can be used to screen for naturally occurring 52906, 33408, or 12189 substrates, to screen for drugs or compounds which modulate 52906, 33408, or 12189 activity, as well as to treat disorders characterized by insufficient or excessive production of 52906, 33408, or 12189 protein or production of 52906, 33408, or 12189 protein forms which have decreased, aberrant or unwanted activity compared to 52906, 33408, or 12189 wild type protein (e.g., disorders characterized by abnormal ion flux such as neurological disorders or cardiac disorders). Moreover, the anti-52906, 33408, or 12189 antibodies of the invention can be used to detect and isolate 52906, 33408, or 12189 proteins, regulate the bioavailability of 52906, 33408, or 12189 proteins, and modulate 52906, 33408, or 12189 activity.

A method of evaluating a compound for the ability to interact with, e.g., bind, a subject 52906, 33408, or 12189 polypeptide is provided. The method includes: contacting the compound with the subject 52906, 33408, or 12189 polypeptide; and evaluating ability of the compound to interact with, e.g., to bind or form a complex with the subject 52906, 33408, or 12189 polypeptide. This method can be performed in vitro, e.g., in a cell free system, or in vivo, e.g., in a two-hybrid interaction trap assay. This method can be used to identify naturally occurring molecules that interact with subject 52906, 33408, or 12189 polypeptide. It can also be used to find natural or synthetic inhibitors of subject 52906, 33408, or 12189 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 52906, 33408, or 12189 proteins, have a stimulatory or inhibitory effect on, for example, 52906, 33408, or 12189 expression or 52906, 33408, or 12189 activity, or have a stimulatory or inhibitory effect on, for example, the expression or activity of a 52906, 33408, or 12189 substrate. Compounds thus identified can be used to modulate the activity of target gene products (e.g., 52906, 33408, or 12189 genes) in a therapeutic protocol, to elaborate the biological function of the target gene product, or to identify compounds that disrupt normal target gene interactions.

In one embodiment, the invention provides assays for screening candidate or test compounds which are substrates of a 52906, 33408, or 12189 protein or polypeptide or a biologically active portion thereof. In another embodiment, the invention provides assays for screening candidate or test compounds that bind to or modulate an activity of a 52906, 33408, or 12189 protein or polypeptide or a biologically active portion thereof.

In one embodiment, an activity of a 52906, 33408, or 12189 protein can be assayed by measuring the flow of $K^+$ ions through a cell membrane and/or by measuring the transmission of signals in an electrically excitable cell, e.g., a neuronal cell or a muscle cell. For example, an activity of a 52906, 33408, or 12189 protein can be assayed by measuring membrane currents as described in Köhler et al. (1996) *Science* 273:709–1714, Saganich et al. (1999) *J. Neuroscience* 19:10789–10802, or Kalman et al. (1998) *J. Biol. Chem.* 273:5851–5857.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 52906, 33408, or 12189 protein or biologically active portion thereof is contacted with a test compound, and the ability of the test compound to modulate 52906, 33408, or 12189 activity is determined. Determining the ability of the test compound to modulate 52906, 33408, or 12189 activity can be accomplished by monitoring, for example, potassium channel activity, e.g., ion flux through a potassium channel. The cell, for example, can be of mammalian origin, e.g., human.

The ability of the test compound to modulate 52906, 33408, or 12189 binding to a compound, e.g., a 52906, 33408, or 12189 substrate, or to bind to 52906, 33408, or 12189 can also be evaluated. This can be accomplished, for example, by coupling the compound, e.g., the substrate, with a radioisotope or enzymatic label such that binding of the compound, e.g., the substrate, to 52906, 33408, or 12189 can be determined by detecting the labeled compound, e.g., substrate, in a complex. Alternatively, 52906, 33408, or 12189 could be coupled with a radioisotope or enzymatic label to monitor the ability of a test compound to modulate 52906, 33408, or 12189 binding to a 52906, 33408, or 12189 substrate in a complex. For example, compounds (e.g., 52906, 33408, or 12189 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 52906, 33408, or 12189 substrate) to interact with 52906, 33408, or 12189 with or without the labeling of any of the interactants can be evaluated. For example, a microphysiometer can be used to detect the interaction of a compound with 52906, 33408, or 12189 without the labeling of either the compound or the 52906, 33408, or 12189. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 52906, 33408, or 12189.

In yet another embodiment, a cell-free assay is provided in which a 52906, 33408, or 12189 protein or biologically active portion thereof is contacted with a test compound and the ability of the test compound to bind to the 52906, 33408, or 12189 protein or biologically active portion thereof is evaluated. Preferred biologically active portions of the 52906, 33408, or 12189 proteins to be used in assays of the present invention include fragments which participate in interactions with non-52906, 33408, or 12189 molecules, e.g., fragments with high surface probability scores.

Soluble and/or membrane-bound forms of isolated proteins (e.g., 52906, 33408, or 12189 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 52906, 33408, or 12189 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 52906, 33408, or 12189, an anti-52906, 33408, or 12189 antibody or its target molecule to facilitate separation of complexed from uncomplexed forms of one or both of the proteins, as well as to accommodate automation of the assay. Binding of a test compound to a 52906, 33408, or 12189 protein, or interaction of a 52906, 33408, or 12189 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/52906, 33408, or 12189 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 52906, 33408, or 12189 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 52906, 33408, or 12189 binding or activity determined using standard techniques.

Other techniques for immobilizing either a 52906, 33408, or 12189 protein or a target molecule on matrices include using conjugation of biotin and streptavidin. Biotinylated 52906, 33408, or 12189 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 52906, 33408, or 12189 protein or target molecules but which do not interfere with binding of the 52906, 33408, or 12189 protein to its target molecule. Such antibodies can be derivatized to the wells of the plate, and unbound target or 52906, 33408, or 12189 protein trapped in the wells by antibody conjugation. Methods for detecting such complexes, in addition to those described above for the GST-immobilized complexes, include immunodetection of complexes using antibodies reactive with the 52906, 33408, or 12189 protein or target molecule, as well as enzyme-linked assays which rely on detecting an enzymatic activity associated with the 52906, 33408, or 12189 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl.* 699:499–525). Further, fluorescence energy transfer may also be conveniently utilized, as described herein, to detect binding without further purification of the complex from solution.

In a preferred embodiment, the assay includes contacting the 52906, 33408 or 12189 protein or biologically active portion thereof with a known compound which binds 52906, 33408, or 12189 to form an assay mixture, contacting the assay mixture with a test compound, and determining the ability of the test compound to interact with a 52906, 33408, or 12189 protein, wherein determining the ability of the test compound to interact with a 52906, 33408, or 12189 protein includes determining the ability of the test compound to preferentially bind to 52906, 33408, or 12189 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding parters." Compounds that disrupt such interactions can be useful in regulating the activity of the target gene product. Such compounds can include, but are not limited to molecules such as antibodies, peptides, and small molecules. The preferred target genes/products for use in this embodiment are the 52906, 33408, or 12189 genes herein identified. In an alternative embodiment, the invention provides methods for determining the ability of the test compound to modulate the activity of a 52906, 33408, or 12189 protein through modulation of the activity of a downstream effector of a 52906, 33408, or 12189 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified. In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 52906, 33408, or 12189 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 52906, 33408, or 12189 ("52906, 33408, or 12189-binding proteins" or "52906, 33408, or 12189-bp") and are involved in 52906, 33408, or 12189 activity. Such 52906, 33408, or 12189-bps can be activators or inhibitors of signals by the 52906, 33408, or 12189 proteins or 52906, 33408, or 12189 targets as, for example, downstream elements of a 52906, 33408, or 12189-mediated signaling pathway.

The two-hybrid system is based on the modular nature of most transcription factors, which consist of separable DNA-binding and activation domains. Briefly, the assay utilizes two different DNA constructs. In one construct, the gene that codes for a 52906, 33408, or 12189 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 52906, 33408, or 12189 protein can be the fused to the activator domain.) If the "bait" and the "prey" proteins are able to interact, in vivo, forming a 52906, 33408, or 12189-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 52906, 33408, or 12189 protein.

In another embodiment, modulators of 52906, 33408, or 12189 expression are identified. For example, a cell or cell free mixture is contacted with a candidate compound and the expression of 52906, 33408, or 12189 mRNA or protein evaluated relative to the level of expression of 52906, 33408, or 12189 mRNA or protein in the absence of the candidate compound. When expression of 52906, 33408, or 12189 mRNA or protein is greater in the presence of the candidate compound than in its absence, the candidate compound is identified as a stimulator of 52906, 33408, or 12189 mRNA, or protein expression. Alternatively, when expression of 52906, 33408, or 12189 mRNA or protein is less (statistically significantly less) in the presence of the candidate compound than in its absence, the candidate compound is identified as an inhibitor of 52906, 33408, or 12189 mRNA or protein expression. The level of 52906, 33408, or 12189 mRNA or protein expression can be determined by methods described herein for detecting 52906, 33408, or 12189 mRNA or protein.

In another aspect, the invention pertains to a combination of two or more of the assays described herein. For example, a modulating agent can be identified using a cell-based or a cell free assay, and the ability of the agent to modulate the activity of a 52906, 33408, or 12189 protein can be confirmed in vivo, e.g., in an animal such as an animal model for a disorder characterized by abnormal ion flux such as a neurological disorder or a cardiac disorder.

This invention further pertains to novel agents identified by the above-described screening assays. Accordingly, it is within the scope of this invention to further use an agent identified as described herein (e.g., a 52906, 33408, or 12189 modulating agent, an antisense 52906, 33408, or 12189 nucleic acid molecule, a 52906, 33408, or 12189-specific antibody, or a 52906, 33408, or 12189-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 52906, 33408, or 12189 with a disease; (ii) identify an individual from a minute biological sample (tissue typing); and (iii) aid in forensic identification of a biological sample. These applications are described in the subsections below.

Chromosome Mapping

The 52906, 33408, or 12189 nucleotide sequences or portions thereof can be used to map the location of the 52906, 33408, or 12189 genes on a chromosome. This process is called chromosome mapping. Chromosome mapping is useful in correlating the 52906, 33408, or 12189 sequences with genes associated with disease.

Briefly, 52906, 33408, or 12189 genes can be mapped to chromosomes by preparing PCR primers (preferably 15–25 bp in length) from the 52906, 33408, or 12189 nucleotide sequences. These primers can then be used for PCR screening of somatic cell hybrids containing individual human chromosomes. Only those hybrids containing the human gene corresponding to the 52906, 33408, or 12189 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 52906, 33408, or 12189 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 52906, 33408, or 12189 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 52906, 33408, or 12189 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 52906, 33408, or 12189 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, or SEQ ID NO:7 can provide positive individual identification with a panel of perhaps 10 to 1,000 primers which each yield a noncoding amplified sequence of 100 bases. If predicted coding sequences, such as those in SEQ ID NO:3, SEQ ID NO:6, or SEQ ID NO:7 are used, a more appropriate number of primers for positive individual identification would be 500–2,000.

If a panel of reagents from 52906, 33408, or 12189 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 52906, 33408 or 12189 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, or SEQ ID NO:7 (e.g., fragments derived from the noncoding regions of SEQ ID NO:1, SEQ ID NO:4, or SEQ ID NO:7 having a length of at least 20 bases, preferably at least 30 bases) are particularly appropriate for this use.

The 52906, 33408, or 12189 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 52906, 33408, or 12189 probes can be used to identify tissue by species and/or by organ type.

In a similar fashion, these reagents, e.g., 52906, 33408, or 12189 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 52906, 33408, or 12189.

Such disorders include, e.g., a disorder associated with the misexpression of 52906, 33408, or 12189 gene, or a disorder characterized by abnormal ion flux such as a neurological disorder or a cardiac disorder.

The method includes one or more of the following:

detecting, in a tissue of the subject, the presence or absence of a mutation which affects the expression of the 52906, 33408, or 12189 gene, or detecting the presence or absence of a mutation in a region which controls the expression of the gene, e.g., a mutation in the 5' control region;

detecting, in a tissue of the subject, the presence or absence of a mutation which alters the structure of the 52906, 33408, or 12189 gene;

detecting, in a tissue of the subject, the misexpression of the 52906, 33408, or 12189 gene, at the mRNA level, e.g., detecting a non-wild type level of a mRNA;

detecting, in a tissue of the subject, the misexpression of the gene, at the protein level, e.g., detecting a non-wild type level of a 52906, 33408, or 12189 polypeptide.

In preferred embodiments the method includes: ascertaining the existence of at least one of: a deletion of one or more nucleotides from the 52906, 33408, or 12189 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, SEQ ID NO:4, or SEQ ID NO:7, or naturally occurring mutants thereof or 5' or 3' flanking sequences naturally associated with the 52906, 33408, or 12189 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 52906, 33408, or 12189 gene; the presence of a non-wild type splicing pattern of a messenger RNA transcript of the gene; or a non-wild type level of 52906, 33408, or 12189.

Methods of the invention can be used prenatally or to determine if a subject's offspring will be at risk for a disorder.

In preferred embodiments the method includes determining the structure of a 52906, 33408, or 12189 gene, an abnormal structure being indicative of risk for the disorder.

In preferred embodiments the method includes contacting a sample from the subject with an antibody to the 52906, 33408, or 12189 protein or a nucleic acid, which hybridizes specifically with the gene. These and other embodiments are discussed below.

Diagnostic and Progostic Assays

Diagnostic and prognostic assays of the invention include methods for assessing the expression level of 52906, 33408, or 12189 molecules and for identifying variations and mutations in the sequence of 52906, 33408, or 12189 molecules.

Expression Monitoring and Profiling

The presence, level, or absence of 52906, 33408, or 12189 protein or nucleic acid in a biological sample can be evaluated by obtaining a biological sample from a test subject and contacting the biological sample with a compound or an agent capable of detecting 52906, 33408, or 12189 protein or nucleic acid (e.g., mRNA, genomic DNA) that encodes 52906, 33408, or 12189 protein such that the presence of 52906, 33408, or 12189 protein or nucleic acid is detected in the biological sample. The term "biological sample" includes tissues, cells and biological fluids isolated from a subject, as well as tissues, cells and fluids present within a subject. A preferred biological sample is serum. The level of expression of the 52906, 33408, or 12189 gene can be measured in a number of ways, including, but not limited to: measuring the mRNA encoded by the 52906 33408, or 12189 genes; measuring the amount of protein encoded by the 52906, 33408, or 12189 genes; or measuring the activity of the protein encoded by the 52906, 33408, or 12189 genes.

The level of mRNA corresponding to the 52906, 33408, or 12189 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 52906, 33408, or 12189 nucleic acid, such as the nucleic acid of SEQ ID NO:1, SEQ ID NO:4, or SEQ ID NO:7, or a portion thereof, such as an oligonucleotide of at least 7, 15, 30, 50, 100, 250 or 500 nucleotides in length and sufficient to specifically hybridize under stringent conditions to 52906, 33408, or 12189 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 52906, 33408, or 12189 genes.

The level of mRNA in a sample that is encoded by one of 52906, 33408, or 12189 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 52906, 33408, or 12189 gene being analyzed.

In another embodiment, the methods further contacting a control sample with a compound or agent capable of detecting 52906, 33408, or 12189 mRNA, or genomic DNA, and comparing the presence of 52906, 33408, or 12189 mRNA or genomic DNA in the control sample with the presence of 52906, 33408, or 12189 mRNA or genomic DNA in the test sample. In still another embodiment, serial analysis of gene expression, as described in U.S. Pat. No. 5,695,937, is used to detect 52906, 33408, or 12189 transcript levels.

A variety of methods can be used to determine the level of protein encoded by 52906, 33408, or 12189. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 52906, 33408, or 12189 protein in a biological sample in vitro as well as in vivo. In vitro techniques for detection of 52906, 33408, or 12189 protein include enzyme linked immunosorbent assays (ELISAs), immunoprecipitations, immunofluorescence, enzyme immunoassays (EIA), radioimmunoassay (RIA), and Western blot analysis. In vivo techniques for detection of 52906, 33408, or 12189 protein include introducing into a subject a labeled anti-52906, 33408, or 12189 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-52906, 33408, or 12189 antibody positioned on an antibody array (as described below). The sample can be detected, e.g., with avidin coupled to a fluorescent label.

In another embodiment, the methods further include contacting the control sample with a compound or agent capable of detecting 52906, 33408, or 12189 protein, and comparing the presence of 52906, 33408, or 12189 protein in the control sample with the presence of 52906, 33408, or 12189 protein in the test sample.

The invention also includes kits for detecting the presence of 52906, 33408, or 12189 in a biological sample. For example, the kit can include a compound or agent capable of detecting 52906, 33408, or 12189 protein or mRNA in a biological sample; and a standard. The compound or agent can be packaged in a suitable container. The kit can further comprise instructions for using the kit to detect 52906, 33408, or 12189 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 52906, 33408, or 12189 expression or activity. As used herein, the term "unwanted" includes an unwanted phenomenon involved in a biological response such disorders characterized by abnormal ion flux such as neurological disorders or cardiac disorders.

In one embodiment, a disease or disorder associated with aberrant or unwanted 52906, 33408, or 12189 expression or activity is identified. A test sample is obtained from a subject and 52906, 33408, or 12189 protein or nucleic acid (e.g., mRNA or genomic DNA) is evaluated, wherein the level, e.g., the presence or absence, of 52906, 33408, or 12189 protein or nucleic acid is diagnostic for a subject having or at risk of developing a disease or disorder associated with aberrant or unwanted 52906, 33408, or 12189 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 52906, 33408, or 12189 expression or activity. For example, such methods can be used to determine whether a subject can be effectively treated with an agent for disorders characterized by abnormal ion flux such as neurological disorders or cardiac disorders.

In another aspect, the invention features a computer medium having a plurality of digitally encoded data records. Each data record includes a value representing the level of expression of 52906, 33408, or 12189 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 52906, 33408, or 12189 (e.g., other genes associated with a 52906, 33408, or 12189-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 52906, 33408, or 12189 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose an ion flux-related disorder in a subject wherein a modulation (increase or decrease) in 52906, 33408, or 12189 expression is an indication that the subject has or is disposed to having a disorder characterized by abnormal ion flux such as a neurological disorder or a cardiac disorder. The method can be used to monitor a treatment for an ion flux-related disorder in a subject. For example, the gene expresion profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 52906, 33408, or 12189 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 52906, 33408, or 12189 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 52906, 33408, or 12189 expression.

Arrays and Uses Thereof

In another aspect, the invention features an array that includes a substrate having a plurality of addresses. At least one address of the plurality includes a capture probe that binds specifically to a 52906, 33408, or 12189 molecule (e.g., a 52906, 33408, or 12189 nucleic acid or a 52906, 33408, or 12189 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 52906, 33408, or 12189 nucleic acid, e.g., the sense or anti-sense strand. In one preferred embodiment, a subset of addresses of the plurality of addresses has a nucleic acid capture probe for 52906, 33408, or 12189. Each address of the subset can include a capture probe that hybridizes to a different region of a 52906, 33408, or 12189 nucleic acid. In another preferred embodiment, addresses of the subset include a capture probe for a 52906, 33408, or 12189 nucleic acid. Each address of the subset is unique, overlapping, and complementary to a different variant of 52906, 33408, or 12189 (e.g., an allelic variant, or all possible hypothetical variants). The array can be used to sequence 52906, 33408, or 12189 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 52906, 33408, or 12189 polypeptide or fragment thereof. The polypeptide can be a naturally-occurring interaction partner of 52906, 33408, or 12189 polypeptide. Preferably, the polypeptide is an antibody, e.g., an antibody described herein (see "Anti-52906, 33408, or 12189 Antibodies," above), such as a monoclonal antibody or a single-chain antibody.

In another aspect, the invention features a method of analyzing the expression of 52906, 33408, or 12189. The method includes providing an array as described above; contacting the array with a sample and detecting binding of a 52906, 33408, or 12189-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 52906, 33408, or 12189. If a sufficient number of diverse samples is analyzed, clustering (e.g., hierarchical clustering, k-means clustering, Bayesian clustering and the like) can be used to identify other genes which are co-regulated with 52906, 33408, or 12189. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 52906, 33408, or 12189 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 52906, 33408, or 12189-associated disease or disorder; and processes, such as a cellular transformation associated with a 52906, 33408, or 12189-associated disease or disorder. The method can also evaluate the treatment and/or progression of a 52906, 33408, or 12189-associated disease or disorder The array is also useful for ascertaining differential expression patterns of one or more genes in normal and abnormal cells. This provides a battery of genes (e.g., including 52906, 33408, or 12189) that could serve as a molecular target for diagnosis or therapeutic intervention.

In another aspect, the invention features an array having a plurality of addresses. Each address of the plurality includes a unique polypeptide. At least one address of the plurality has disposed thereon a 52906, 33408, or 12189 polypeptide or fragment thereof. Methods of producing polypeptide arrays are described in the art, e.g., in De Wildt et al. (2000). *Nature Biotech*. 18, 989–994; Lueking et al. (1999). *Anal. Biochem*. 270, 103–111; Ge, H. (2000). *Nucleic Acids Res*. 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 52906, 33408, or 12189 polypeptide or fragment thereof. For example, multiple variants of a 52906, 33408, or 12189 polypeptide (e.g., encoded by allelic variants, site-directed mutants, random mutants, or combinatorial mutants) can be disposed at individual addresses of the plurality Addresses in addition to the address of the plurality can be disposed on the array.

The polypeptide array can be used to detect a 52906, 33408, or 12189 binding compound, e.g., an antibody in a sample from a subject with specificity for a 52906, 33408, or 12189 polypeptide or the presence of a 52906, 33408, or 12189-binding protein or ligand.

The array is also useful for ascertaining the effect of the expression of a gene on the expression of other genes in the same cell or in different cells (e.g., ascertaining the effect of 52906, 33408, or 12189 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 52906, 33408, or 12189 or from a cell or subject in which a 52906, 33408, or 12189 mediated response has been elicited, e.g., by contact of the cell with 52906, 33408, or 12189 nucleic acid or protein, or administration to the cell or subject 52906, 33408, or 12189 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 52906, 33408, or 12189 (or does not express as highly as in the case of the 52906, 33408, or 12189 positive plurality of capture probes) or from a cell or subject which in which a 52906, 33408, or 12189 mediated response has not been elicited (or has been elicited to a lesser extent than in the first sample); contacting the array with one or more inquiry probes (which is preferably other than a 52906, 33408, or 12189 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 52906, 33408, or 12189 or from a cell or subject in which a 52906, 33408, or 12189-mediated response has been elicited, e.g., by contact of the cell with 52906, 33408, or 12189 nucleic acid or protein, or administration to the cell or subject 52906, 33408, or 12189 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 52906, 33408, or 12189 (or does not express as highly as in the case of the 52906, 33408, or 12189 positive plurality of capture probes) or from a cell or subject which in which a 52906, 33408, or 12189 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 52906, 33408, or 12189, e.g., analyzing structure, function, or relatedness to other nucleic acid or amino acid sequences. The method includes: providing a 52906, 33408, or 12189 nucleic acid or amino acid sequence; comparing the 52906, 33408, or 12189 sequence with one or more preferably a plurality of sequences from a collection of sequences, e.g., a nucleic acid or protein sequence database; to thereby analyze 52906, 33408, or 12189.

Detection of Variations or Mutations

The methods of the invention can also be used to detect genetic alterations in a 52906, 33408, or 12189 gene, thereby determining if a subject with the altered gene is at risk for a disorder characterized by misregulation in 52906, 33408, or 12189 protein activity or nucleic acid expression, such as a disorder characterized by abnormal ion flux such as a neurological disorder or a cardiac disorder. In preferred embodiments, the methods include detecting, in a sample from the subject, the presence or absence of a genetic alteration characterized by at least one of an alteration affecting the integrity of a gene encoding a 52906, 33408, or 12189-protein, or the mis-expression of the 52906, 33408, or 12189 gene. For example, such genetic alterations can be detected by ascertaining the existence of at least one of 1) a deletion of one or more nucleotides from a 52906, 33408, or 12189 gene; 2) an addition of one or more nucleotides to a 52906, 33408, or 12189 gene; 3) a substitution of one or more nucleotides of a 52906, 33408, or 12189 gene, 4) a chromosomal rearrangement of a 52906, 33408, or 12189 gene; 5) an alteration in the level of a messenger RNA transcript of a 52906, 33408, or 12189 gene, 6) aberrant modification of a 52906, 33408, or 12189 gene, such as of the methylation pattern of the genomic DNA, 7) the presence of a non-wild type splicing pattern of a messenger RNA transcript of a 52906, 33408, or 12189 gene, 8) a non-wild type level of a 52906, 33408, or 12189-protein, 9) allelic loss of a 52906, 33408, or 12189 gene, and 10) inappropriate post-translational modification of a 52906, 33408, or 12189-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 52906, 33408, or 12189-gene. This method can include the steps of collecting a sample of cells from a subject, isolating nucleic acid (e.g., genomic, mRNA or both) from the sample, contacting the nucleic acid sample with one or more primers which specifically hybridize to a 52906, 33408, or 12189 gene under conditions such that hybridization and amplification of the 52906, 33408, or 12189-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 52906, 33408, or 12189 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 52906, 33408, or 12189 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 52906, 33408, or 12189 nucleic acid or a putative variant (e.g., allelic variant) thereof. A probe can have one or more mismatches to a region of a 52906, 33408, or 12189 nucleic acid (e.g., a destabilizing mismatch). The arrays can have a high density of addresses, e.g., can contain hundreds or thousands of oligonucleotides probes (Cronin, M. T. et al. (1996) *Human Mutation* 7:244–255; Kozal, M. J. et al. (1996) *Nature Medicine* 2:753–759). For example, genetic mutations in 52906, 33408, or 12189 can be identified in two-dimensional arrays containing light-generated DNA probes as described in Cronn, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 52906, 33408, or 12189 gene and detect mutations by comparing the sequence of the sample 52906, 33408, or 12189 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 52906, 33408, or 12189 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 52906, 33408, or 12189 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 52906, 33408, or 12189 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control 52906, 33408, or 12189 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 52906, 33408, or 12189 nucleic acid.

In a preferred embodiment the set includes a first and a second oligonucleotide. The first and second oligonucleotide can hybridize to the same or to different locations of SEQ ID NO:1, SEQ ID NO:4, or SEQ ID NO:7 or the complement of SEQ ID NO:1, SEQ ID NO:4, or SEQ ID NO:7. Different locations can be different but overlapping, or non-overlapping on the same strand. The first and second oligonucleotide can hybridize to sites on the same or on different strands.

The set can be useful, e.g., for identifying SNP's, or identifying specific alleles of 52906, 33408, or 12189. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 52906, 33408, or 12189 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 52906, 33408, or 12189 gene.

Use of 52906, 33408, or 12189 Molecules as Surrogate Markers

The 52906, 33408, or 12189 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 52906, 33408, or 12189 molecules of the invention may be detected, and may be correlated with one or more biological states in vivo. For example, the 52906, 33408, or 12189 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258–264; and James (1994) *AIDS Treatment News Archive* 209.

The 52906, 33408, or 12189 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharnacodynanic markers are of particular use in increasing the sensitivity of detection of drug effects, particularly when the drug is administered in low doses. Since even a small amount of a drug may be sufficient to activate multiple rounds of marker (e.g., a 52906, 33408, or 12189 marker) transcription or expression, the amplified marker may be in a quantity which is more readily detectable than the drug itself. Also, the marker may be more easily detected due to the nature of the marker itself; for example, using the methods described herein, anti-52906, 33408, or 12189 antibodies may be employed in an immune-based detection system for a 52906, 33408, or 12189 protein marker, or 52906, 33408, or 12189-specific radiolabeled probes may be used to detect a 52906, 33408, or 12189 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 52906, 33408, or 12189 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 52906, 33408, or 12189 protein or RNA) for specific tumor markers in a subject, a drug or course of treatment may be selected that is optimized for the treatment of the specific tumor likely to be present in the subject. Similarly, the presence or absence of a specific sequence mutation in 52906, 33408 or 12189 DNA may correlate 52906, 33408, or 12189 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-52906, 33408, or 12189 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 52906, 33408, or 12189 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 52906, 33408, or 12189 molecules of the present invention or 52906,33408, or 12189 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 52906, 33408, or 12189 expression or activity, by administering to the subject a 52906, 33408, or 12189 or an agent which modulates 52906, 33408, or 12189 expression or at least one 52906, 33408, or 12189 activity. Subjects at risk for a disease which is caused or contributed to by aberrant or unwanted 52906, 33408, or 12189 expression or activity can be identified by, for example, any or a combination of diagnostic or prognostic assays as described herein. Administration of a prophylactic agent can occur prior to the manifestation of symptoms characteristic of the 52906, 33408, or 12189 aberrance, such that a disease or disorder is prevented or, alternatively, delayed in its progression. Depending on the type of 52906, 33408, or 12189 aberrance, for example, a 52906, 33408, or 12189, 52906, 33408, or 12189 agonist or 52906, 33408, or 12189 antagonist agent can be used for treating the subject. The appropriate agent can be determined based on screening assays described herein.

It is possible that some 52906, 33408, or 12189 disorders can be caused, at least in part, by an abnormal level of gene product, or by the presence of a gene product exhibiting abnormal activity. As such, the reduction in the level and/or activity of such gene products would bring about the amelioration of disorder symptoms.

The 52906, 33408, or 12189 molecules can act as novel diagnostic targets and therapeutic agents for controlling one or more of cellular proliferative and/or differentiative disorders, disorders associated with bone metabolism, immune disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of 52906, 33408, or 12189 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 52906, 33408, or 12189 molecules effects in bone cells, e.g. osteoclasts and osteoblasts, that may in turn result in bone formation and degeneration. For example, 52906, 33408, or 12189 molecules may support different activities of bone resorbing osteoclasts such as the stimulation of differentiation of monocytes and mononuclear phagocytes into osteoclasts. Accordingly, 52906, 33408, or 12189 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 52906, 33408, or 12189 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 52906, 33408, or 12189 molecules may play an important role in the etiology of certain viral diseases, including but not limited to Hepatitis B, Hepatitis C and Herpes Simplex Virus (HSV). Modulators of 52906, 33408, or 12189 activity could be used to control viral diseases. The modulators can be used in the treatment and/or diagnosis of viral infected tissue or virus-associated tissue fibrosis, especially liver and liver fibrosis. Also, 52906, 33408, or 12189 modulators can be used in the treatment and/or diagnosis of virus-associated carcinoma, especially hepatocellular cancer.

Additionally, 52906, 33408, or 12189 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 52906, 33408, or 12189 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 52906, 33408, or 12189 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 52906, 33408, or 12189 expression is through the use of aptamer molecules specific for 52906, 33408, or 12189 protein. Aptamers are nucleic acid molecules having a tertiary structure which permits them to specifically bind to protein ligands (see, e.g., Osborne, et al. (1997) *Curr. Opin. Chem Biol*. 1:5–9; and Patel, D. J. (1997) *Curr Opin Chem Biol* 1:32–46). Since nucleic acid molecules may in many cases be more conveniently introduced into target cells than therapeutic protein molecules may be, aptamers offer a method by which 52906, 33408, or 12189 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 52906, 33408, or 12189 disorders. For a description of antibodies, see the Antibody section above.

In circumstances wherein injection of an animal or a human subject with a 52906, 33408, or 12189 protein or epitope for stimulating antibody production is harmful to the subject, it is possible to generate an immune response against 52906, 33408, or 12189 through the use of anti-idiotypic antibodies (see, for example, Herlyn, D. (1999) *Ann Med* 31:66–78; and Bhattacharya-Chatteijee, M., and Foon, K. A. (1998) *Cancer Treat Res*. 94:51–68). If an anti-idiotypic antibody is introduced into a mammal or human subject, it should stimulate the production of anti-idiotypic antibodies, which should be specific to the 52906, 33408, or 12189 protein. Vaccines directed to a disease characterized by 52906, 33408, or 12189 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 52906, 33408, or 12189 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 52906, 33408, or 12189 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647.

Through the use of isotope-labeling, the "free" concentration of compound which modulates the expression or activity of 52906, 33408, or 12189 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 52906, 33408, or 12189 expression or activity for therapeutic purposes. Accordingly, in an exemplary embodiment, the modulatory method of the invention involves contacting a cell with a 52906, 33408, or 12189 or agent that modulates one or more of the activities of 52906, 33408, or 12189 protein activity associated with the cell. An agent that modulates 52906, 33408, or 12189 protein activity can be an agent as described herein, such as a nucleic acid or a protein, a naturally-occurring target molecule of a 52906, 33408, or 12189 protein (e.g., a 52906, 33408, or 12189 substrate or receptor), a 52906, 33408, or 12189 antibody, a 52906, 33408, or 12189 agonist or antagonist, a peptidomimetic of a 52906, 33408, or 12189 agonist or antagonist, or other small molecule.

In one embodiment, the agent stimulates one or 52906, 33408, or 12189 activities. Examples of such stimulatory agents include active 52906, 33408, or 12189 protein and a nucleic acid molecule encoding 52906, 33408, or 12189. In another embodiment, the agent inhibits one or more 52906, 33408, or 12189 activities. Examples of such inhibitory agents include antisense 52906, 33408, or 12189 nucleic acid molecules, anti-52906, 33408, or 12189 antibodies, and 52906, 33408, or 12189 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 52906, 33408, or 12189 protein or nucleic acid molecule. In one embodiment, the method involves administering an agent (e.g., an agent identified by a screening assay described herein), or combination of agents that modulates (e.g., up regulates or down regulates) 52906, 33408, or 12189 expression or activity. In another embodiment, the method involves administering a 52906, 33408, or 12189 protein or nucleic acid molecule as therapy to compensate for reduced, aberrant, or unwanted 52906, 33408, or 12189 expression or activity.

Stimulation of 52906, 33408, or 12189 activity is desirable in situations in which 52906, 33408, or 12189 is abnormally downregulated and/or in which increased 52906, 33408, or 12189 activity is likely to have a beneficial effect. For example, stimulation of 52906, 33408, or 12189 activity is desirable in situations in which a 52906, 33408, or 12189 is downregulated and/or in which increased 52906, 33408, or 12189 activity is likely to have a beneficial effect. Likewise, inhibition of 52906, 33408, or 12189 activity is desirable in situations in which 52906, 33408, or 12189 is abnormally upregulated and/or in which decreased 52906, 33408, or 12189 activity is likely to have a beneficial effect.

Pharmacogenomics

The 52906, 33408, or 12189 molecules of the present invention, as well as agents, or modulators which have a stimulatory or inhibitory effect on 52906, 33408, or 12189 activity (e.g., 52906, 33408, or 12189 gene expression) as identified by a screening assay described herein can be administered to individuals to treat prophylactically or therapeutically) 52906, 33408, or 12189 associated disorders (e.g., a disorder characterized by abnormal ion flux such as a neurological disorder or a cardiac disorder) associated with aberrant or unwanted 52906, 33408, or 12189 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 52906, 33408, or 12189 molecule or 52906, 33408, or 12189 modulator as well as tailoring the dosage and/or therapeutic regimen of treatment with a 52906, 33408, or 12189 molecule or 52906, 33408, or 12189 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofuirans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Alternatively, a method termed the "candidate gene approach," can be utilized to identify genes that predict drug response. According to this method, if a gene that encodes a drug's target is known (e.g., a 52906, 33408, or 12189 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 52906, 33408, or 12189 molecule or 52906, 33408, or 12189 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 52906, 33408, or 12189 molecule or 52906, 33408, or 12189 modulator, such as a modulator identified by one of the exemplary screening assays described herein.

The present invention further provides methods for identifying new agents, or combinations, that are based on identifying agents that modulate the activity of one or more of the gene products encoded by one or more of the 52906, 33408, or 12189 genes of the present invention, wherein these products may be associated with resistance of the cells to a therapeutic agent. Specifically, the activity of the proteins encoded by the 52906, 33408, or 12189 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 52906, 33408, or 12189 protein can be applied in clinical trials. For example, the effectiveness of an agent determined by a screening assay as described herein to increase 52906, 33408, or 12189 gene expression, protein levels, or upregulate 52906, 33408, or 12189 activity, can be monitored in clinical trials of subjects exhibiting decreased 52906, 33408, or 12189 gene expression, protein levels, or downregulated 52906, 33408, or 12189 activity. Alternatively, the effectiveness of an agent determined by a screening assay to decrease 52906, 33408, or 12189 gene expression, protein levels, or downregulate 52906, 33408, or 12189 activity, can be monitored in clinical trials of subjects exhibiting increased 52906, 33408, or 12189 gene expression, protein levels, or upregulated 52906, 33408, or 12189 activity. In such clinical trials, the expression or activity of a 52906, 33408, or 12189 gene, and preferably, other genes that have been implicated in, for example, a 52906, 33408, or 12189-associated disorder can be used as a "read out" or markers of the phenotype of a particular cell.

52906, 33408, or 12189 Informatics

The sequence of a 52906, 33408, or 12189 molecule is provided in a variety of media to facilitate use thereof. A sequence can be provided as a manufacture, other than an isolated nucleic acid or amino acid molecule, which contains a 52906, 33408, or 12189. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 52906, 33408, or 12189 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 52906, 33408, or 12189, e.g., analyzing structure, function, or relatedness to one or more other nucleic acid or amino acid sequences. The method includes: providing a 52906, 33408, or 12189 nucleic acid or amino acid sequence; comparing the 52906, 33408, or 12189 sequence with a second sequence, e.g., one or more preferably a plurality of sequences from a collection of sequences, e.g., a nucleic acid or protein sequence database to thereby analyze 52906, 33408, or 12189. The method can be performed in a machine, e.g., a computer, or manually by a skilled artisan.

The method can include evaluating the sequence identity between a 52906, 33408, or 12189 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 52906, 33408, or 12189 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 52906, 33408, or 12189 sequence, or record, in machine-readable form; comparing a second sequence to the 52906, 33408, or 12189 sequence; thereby analyzing a sequence. Comparison can include comparing to sequences for sequence identity or determining if one sequence is included within the other, e.g., determining if the 52906, 33408, or 12189 sequence includes a sequence being compared. In a preferred embodiment the 52906, 33408, or 12189 or second sequence is stored on a first computer, e.g., at a first site and the comparison is performed, read, or recorded on a second computer, e.g., at a second site. E.g., the 52906, 33408, or 12189 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 52906, 33408, or 12189-associated disease or disorder or a pre-disposition to a 52906, 33408, or 12189-associated disease or disorder, wherein the method comprises the steps of determining 52906, 33408, or 12189 sequence information associated with the subject and based on the 52906, 33408, or 12189 sequence information, determining whether the subject has a 52906, 33408, or 12189-associated disease or disorder or a pre-disposition to a 52906, 33408, or 12189-associated disease or disorder and/or recommending a particular treatment for the disease, disorder or pre-disease condition.

The invention further provides in an electronic system and/or in a network, a method for determining whether a subject has a 52906, 33408, or 12189-associated disease or disorder or a pre-disposition to a disease associated with a 52906, 33408, or 12189 wherein the method comprises the steps of determining 52906, 33408, or 12189 sequence information associated with the subject, and based on the 52906, 33408, or 12189 sequence information, determining whether the subject has a 52906, 33408, or 12189-associated disease or disorder or a pre-disposition to a 52906, 33408, or 12189-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 52906, 33408, or 12189 sequence of the subject to the 52906, 33408, or 12189 sequences in the database to thereby determine whether the subject as a 52906, 33408, or 12189-associated disease or disorder, or a pre-disposition for such.

The present invention also provides in a network, a method for determining whether a subject has a 52906, 33408, or 12189 associated disease or disorder or a pre-disposition to a 52906, 33408, or 12189-associated disease or disorder associated with 52906, 33408, or 12189, said method comprising the steps of receiving 52906, 33408, or 12189 sequence information from the subject and/or information related thereto, receiving phenotypic information associated with the subject, acquiring information from the network corresponding to 52906, 33408, or 12189 and/or corresponding to a 52906, 33408, or 12189-associated disease or disorder (e.g., a disorder characterized by abnormal ion flux such as a neurological disorder or a cardiac disorder), and based on one or more of the phenotypic information, the 52906, 33408, or 12189 information (e.g., sequence information and/or information related thereto), and the acquired information, determining whether the subject has a 52906, 33408, or 12189-associated disease or disorder or a pre-disposition to a 52906, 33408, or 12189-associated disease or disorder. The method may further comprise the step of recommending a particular treatment for the disease, disorder or pre-disease condition.

The present invention also provides a method for determining whether a subject has a 52906, 33408, or 12189-associated disease or disorder or a pre-disposition to a 52906, 33408, or 12189-associated disease or disorder, said method comprising the steps of receiving information related to 52906, 33408, or 12189 (e.g., sequence information and/or information related thereto), receiving phenotypic information associated with the subject, acquiring information from the network related to 52906, 33408, or 12189 and/or related to a 52906, 33408, or 12189-associated disease or disorder, and based on one or more of the phenotypic information, the 52906, 33408, or 12189 information, and the acquired information, determining whether the subject has a 52906, 33408, or 12189-associated disease or disorder or a pre-disposition to a 52906, 33408, or 12189-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human 52906, 33408, and 12189 cDNAs

The human 52906 nucleic acid sequence is recited as follows:

```
GCGTCCGCAGATTCCAGAGCCTGCCGGCTGGGAAAGATCCGGTCTCGGGG
TCGGCTATGATCCCGCAGCGGCCAAGGCAGGGCTCAGGCCCCGGGATTCT
CCCCACACGCTGCTGCACTGGCGCAGCCGGTCGCCAAACTTTTTCTCCCC
AAAGCCAGTGCCCCCGCAGTTACTTGGCGGGCAGCCGGCAGCCCACTCTC
GGCGGGATGATCTGGGAGAAGCGGGCGTGGGACGAGGGGGCTGCTGTTTT
GCAGCCCTGCGAGGCGTGCAGTCGGAGAAGTGGTCGGGGTTCCACACCGT
CCCTGAGCCTGCCCCCTGGCCAAGGTGGCCCGACGTGCTGCAGTGGCTGG
CGCAGGTGATCCGGGCAGCGCGTCCGGCACTAGTCAAGGGGCAGCGGCA
CGGGAGGGAGGGGCGCCTTTCTCTTTTCTCCTCCCCCTGCAGCCCAGCTG
CACTGCGTGGGGCTCTCCATCTCCACGCAATCAGCAGGCGGAATCCCTG
CCCTGGAGCGCCCTGGCTCTGGACTGCACCCCCCTAGGGTTTGTCCTGCA
GATTCTCCTCCCCATCTTTCTCTGCCACACACGCTTCCCTAAGCCGCGCG
CGCCGCAAACTCAGTCTCGGTCCCCGCAGGTGATGTCATGCCCATTGTT
TTGGTGCGCCCAACCAATCGGACTCGCCGCCTGGATTCTACCGGAGCCGG
CATGGGCCCTTCCTCGCACCAGCAGCAGGAGTCCCCGCTCCCGACCATAA
CGCATTGCGCAGGGTGCACCACCGCTTGGTCTCCCTGCAGCTTTAACAGC
CCTGACATGGAAACCCCATTGCAGTTCCAGCGCGGCTTCTTCCCAGAGCA
GCCGCCGCCGCCGCCGCGCTCCTCACACCTGCATTGCCAGCAGCAGCAAC
AGAGCCAGGACAAGCCGTGCCCGCCCTTCGCGCCCCTCCCGCACCCTCAC
CACCACCCGCACCTCGCGCACCAGCAGCCGGCCAGCGGCGGCAGCAGCCC
ATGCCTCCGGTGCAACAGCTGCGCCTCCTCCGGTGCCCCGGCGGCGGGG
CGGGAGATAACCTGTCCCTGCTGCTCCGCACCTCCTCGCCCGGCGGCGCC
TTCCGGACCCGCACCTCCTCGCCGCTGTCGGGCTCGTCCTGCTGCTGCTG
CTGCTGCTCGTCGCGCCGGGGCAGCCAGCTCAATGTGAGCGAGCTGACGC
CGTCCAGCCATGCCAGTGCGCTCCGGCAGCAGTACGCGCAGCAGTCCGCG
CAGCAGTCGGCGTCCGCCTCCCAGTACCACCAGTGCCACAGCCTGCAGCC
CGCCGCCAGCCCCACGGGCAGCCTCGGCAGTCTGGGCTCCGGGCCCCCGC
TCTCGCACCACCACCACCACCCGCACCCGGCGCACCACCAGCACCACCAG
CCCCAGGCGCGCCGCGAGAGCAACCCCTTCACCGAAATAGCCATGAGCAG
CTGCAGGTACAACGGGGCGTCATGCGGCCGCTCAGCAACTTGAGCGCGT
CCCGCCGGAACCTGCACGAGATGGACTCAGAGGCGCAGCCCCTGCAGCCC
CCCGCGTCTGTCGGAGGAGGTGGCGGCGCGTCCTCCCCGTCTGCAGCCGC
TGCCGCCGCCGCCGCTGTTTCGTCCTCAGCCCCCGAGATCGTGGTGTCTA
AGCCCGAGCACAACAACTCCAACAACCTGGCGCTCTATGGAACCGGCGGC
GGAGGCAGCACTGGAGGAGGCGGCGGCGGTGGCGGGAGCGGGCACGGCAG
CAGCAGTGGCACCAAGTCCAGCAAAAAGAAAAACCAGAACATCGGCTACA
AGCTGGGCCACCGGCGCGCCCTGTTCGAAAAGCGCAAGCGGCTCAGCGAC
TACGCGCTCATCTTCGGCATGTTCGGCATCGTGGTCATGGTCATCGAGAC
CGAGCTGTCGTGGGGCGCCTACGACAAGGCGTCGCTGTATTCCTTAGCTC
TGAAATGCCTTATCAGTCTCTCCACGATCATCCTGCTCGGTCTGATCATC
GTGTACCACGCCAGGGAAATACAGTTGTTCATGGTGGACAATGGAGCAGA
TGACTGGAGAATAGCCATGACTTATGAGCGTATTTTCTTCATCTGCTTGG
AAATACTGGTGTGTGCTATTCATCCCATACCTGGGAATTATACATTCACA
TGGACGGCCCGGCTTGCCTTCTCCTATGCCCATCCACAACCACCGCTGA
TGTGGATATTATTTTATCTATACCAATGTTCTTAAGACTCTATCTGATTG
CCAGAGTCATGCTTTTACATAGCAAACTTTTCACTGATACCTCCTCTAGA
AGCATTGGAGCACTTAATAAGATAAACTTCAATACACGTTTTGTTATGAA
GACTTTAATGACTATATGCCCAGGAACTGTACTCTTGGTTTTTAGTATCT
CATTATGGATAATTGCCGCATGGACTGTCCGAGCTTGTGAAAGGTACCAT
GATCAACAGGATGTTACTAGCAACTTCCTTGGAGCGATGTGGTTGATATC
AATAACTTTTCTCTCCATTGGTTATGGTGACATGGTACCTAACACATACT
GTGGAAAAGGAGTCTGCTTACTTACTGGAATTATGGGTGCTGGTTGCACA
GCCCTGGTGGTAGCTGTAGTGGCAAGGAAGCTAGAACTTACCAAAGCAGA
AAAACACGTGCACAATTTCATGATGGATACTCAGCTGACTAAAAGAGTAA
AAAATGCAGCTGCCAATGTACTCAGGGAAACATGGCTAATTTACAAAAAT
```

-continued

```
ACAAAGCTAGTGAAAAAGATAGATCATGCAAAAGTAAGAAAACATCAACG

AAAATTCCTGCAAGCTATTCATCAATTAAGAAGTGTAAAAATGGAGCAGA

GGAAACTGAATGACCAAGCAAACACTTTGGTGGACTTGGCAAAGACCCAG

AACATCATGTATGATATGATTTCTGACTTAAACGAAAGGAGTGAAGACTT

CGAGAAGAGGATTGTTACCCTGGAAACAAAACTAGAGACTTTGATTGGTA

GCATCCACGCCCTCCCTGGGCTCATAAGCCAGACCATCAGGCAGCAGCAG

AGAGATTTCATTGAGGCTCAGATGGAGAGCTACGACAAGCACGTCACTTA

CAATGCTGAGCGGTCCCGGTCCTCGTCCAGGAGGCGGCGGTCCTCTTCCA

CAGCACCACCAACTTCATCAGAGAGTAGCTAGAAGAGAATAAGTTAACCA

CAAAATAAGACTTTTTGCCATCATATGGTCAATATTTTAGCTTTTATTGT

AAAGCCCCTATGGTTCTAATCAGCGTTATCCGGGTTCTGATGTCAGAATC

CTGGGAACCTGAACACTAAGTTTTAGGCCAAAATGAGTGAAAACTCTTTT

TTTTTCTTTCAGATGCACAGGGAATGCACCTATTATTGCTATATAGATTG

TTCCTCCTGTAATTTCACTAACTTTTTATTCATGCACTTCAAACAAACTT

TACTACTACATTATATGATATATAATAAAAAAAGTTAATTTCTGCAAAAA

AAAAAAAAAAAAAAAAAACGGACGGG (SEQ ID NO:1).
```

The human 52906 sequence (FIG. 1; SEQ ID NO:1) is approximately 3525 nucleotides long. The nucleic acid sequence includes an initiation codon (ATG) and a termination codon (TAG), which are underscored above. The region between and inclusive of the initiation codon and the termination codon is a methionine-initiated coding sequence of about 2544 nucleotides, including the termination codon (nucleotides indicated as "coding" of SEQ ID NO:1; SEQ ID NO:3). The coding sequence encodes a 847 amino acid protein (SEQ ID NO:2), which is recited as follows:

```
MPIVLVRPTNRTRRLDSTGAGMGPSSHQQQESPLPTITHCAGCTTAWS

PCSFNSPDMETPLQFQRGFFPEQPPPPPRSSHLHCQQQQQSQDKPCPP

FAPLPHPHHHPHLAHQQPASGGSSPCLRCNSCASSGAPAAGAGDNLSL

LLRTSSPGGAFRTRTSSPLSGSSCCCCCCSSRRGSQLNVSELTPSSHA

SALRQQYAQQSAQQSASASQYHQCHSLQPAASPTGSLGSLGSGPPLSH

HHHPHPAHHQHHQPQARRESNPFTEIAMSSCRYNGGVMRPLSNLSASR

RNLHEMDSEAQPLQPPASVGGGGGASSPSAAAAAAAAVSSSAPEIVVS

KPEHNNSNNLALYGTGGGGSTGGGGGGGSGHGSSSGTKSSKKKNQNI

GYKLGHRRALFEKRKRLSDYALIFGMFGIVVMVIETELSWGAYDKASL

YSLALKCLISLSTJIILLGLIIVYHAREIQLFMVDNGADDWRIAMTYE

RIFFICLEILVCAIHPIPGNYTFTWTARLAFSYAPSTTTADVDIILSI

PMFLRLYLIARVMLLHSKLFTDTSSRSIGALNKINFNTRFVMKTLMTI

CPGTVLLVFSISLWIIAAWTVRACERYHDQQDVTSNFLGAMWLISITF

LSIGYGDMVPNTYCGKGVCLLTGIMGAGCTALVVAVVARKLELTKAEK

HVHNFMMDTQLTKRVKNAAANVLRETWLIYKNTKLVKKIDHAKVRKHQ

RKFLQAIHQLRSVKMEQRKLNDQANTLVDLAKTQNIMYDMISDLNERS

EDFEKRIVTLETKLETLIGSIHALPGLISQTIRQQQRDFIEAQMESYD
```

-continued

```
KHVTYNAERSRSSSRRRRSSSTAPPTSSESS (SEQ ID NO:2).
```

The human 33408 nucleic acid sequence is recited as follows:

```
GACCCACGCGTCCGCTCCCCCGTGTGCGGCACCGCCACAGTCTGGGCACG

GCGGCCGGGGAGCGCTACTACCATGAACTGCCTGGTCCTCCTCCCCAGA

GCTGCTCATCCGGGTCGGGCTGGAGACACAGTCAGGGGACCCCGTCGCCG

CCGCCGCGCCCCCTCTTCTTTCGGCTCAATCTTCTCTTCCACCTTTTCCT

CCTCTTCCTCCACCTTCTTTGCCTGCATCCCCCCCTCCCCCGCCGCGGAT

CCTGGCCGCTGCTCTCCAGACCCAGGATGCCGGGGGGCAAGAGAGGGCTG

GTGGCACCGCAGAACACATTTTTGGAGAACATCGTCAGGCGCTCCAGTGA

ATCAAGTTTCTTACTGGGAAATGCCCAGATTGTGGATTGGCCTGTAGTTT

ATAGTAATGACGGTTTTTGTAAACTCTCTGGATATCATCGAGCTGACGTC

ATGCAGAAAAGCAGCACTTGCAGTTTTATGTATGGGGAATTGACTGACAA

GAAGACCATTGAGAAAGTCAGGCAAACTTTTGACAACTACGAATCAAACT

GCTTTGAAGTTCTTCTGTACAAGAAAAACAGAACCCCTGTTTGGTTTTAT

ATGCAAATTGCACCAATAAGAAATGAACATGAAAAGGTGGTCTTGTTCCT

GTGTACTTTCAAGGATATTACGTTGTTCAAACAGCCAATAGAGGATGATT

CAACAAAAGGTTGGACGAAATTTGCCCGATTGACACGGGCTTTGACAAAT

AGCCGAAGTGTTTTGCAGCAGCTCACGCCAATGAATAAAACAGAGGTGGT

CCATAAACATTCAAGACTAGCTGAAGTTCTTCAGCTGGGATCAGATATCC

TTCCTCAGTATAAACAAGAAGCGCCAAAGACGCCACCACACATTATTTTA

CATTATTGTGCTTTTAAAACTACTTGGGATTGGGTGATTTTAATTCTTAC

CTTCTACACCGCCATTATGGTTCCTTATAATGTTTCCTTCAAAACAAAGC

AGAACAACATAGCCTGGCTGGTACTGGATAGTGTGGTGGACGTTATTTTT

CTGGTTGACATCGTTTTAAATTTTCACACGACTTTCGTGGGGCCCGGTGG

AGAGGTCATTTCTGACCCTAAGCTCATAAGGATGAACTATCTGAAAACTT

GGTTTGTGATCGATCTGCTGTCTTGTTTACCTTATGACATCATCAATGCC

TTTGAAAATGTGGATGAGGGAATCAGCAGTCTCTTCAGTTCTTTAAAAGT

GGTGCGTCTCTTACGACTGGGCCGTGTGGCTAGGAAACTGGACCATTACC

TAGAATATGGAGCAGCAGTCCTCGTGCTCCTGGTGTGTGTTTGGACTG

GTGGCCCACTGGCTGGCCTGCATATGGTATAGCATCGGAGACTACGAGGT

CATTGATGAAGTCACTAACACCATCCAAATAGACAGTTGGCTCTACCAGC

TGGCTTTGAGCATTGGGACTCCATATCGCTACAATACCAGTGCTGGGATA

TGGGAAGGAGGACCCAGCAAGGATTCATTGTACGTGTCCTCTCTCTACTT

TACCATGACAAGCCTTACAACCATAGGATTTGGAAACATAGCTCCTACCA

CAGATGTGGAGAAGATGTTTTCGGTGGCTATGATGATGGTTGGCTCTCTT

CTTTATGCAACTATTTTTGGAAATGTTACAACAATTTTCCAGCAAATGTA

TGCCAACACCAACCGATACCATGAGATGCTGAATAATGTACGGGACTTCC

TAAAACTCTATCAGGTCCCAAAAGGCCTTAGTGAGCGAGTCATGGATTAT
```

-continued
```
ATTGTCTCAACATGGTCCATGTCAAAAGGCATTGATACAGAAAAGGTCCT

CTCCATCTGTCCCAAGGACATGAGAGCTGATATCTGTGTTCATCTAAACC

GGAAGGTTTTTAATGAACATCCTGCTTTTCGATTGGCCAGCGATGGGTGT

CTGCGCGCCTTGGCGGTAGAGTTCCAAACCATTCACTGTGCTCCCGGGGA

CCTCATTTACCATGCTGGAGAAAGTGTGGATGCCCTCTGCTTTGTGGTGT

CAGGATCCTTGGAAGTCATCCAGGATGATGAGGTGGTGGCTATTTTAGGG

AAGGGTGATGTATTTGGAGACATCTTCTGGAAGGAAACCACCCTTGCCCA

TGCATGTGCGAACGTCCGGGCACTGACGTACTGTGACCTACACATCATCA

AGCGGGAAGCCTTGCTCAAAGTCCTGGACTTTTATACAGCTTTTGCAAAC

TCCTTCTCAAGGAATCTCACTCTTACTTGCAATCTGAGGAAACGGATCAT

CTTTCGTAAGATCAGTGATGTGAAGAAAGAGGAGGAGGAGCGCCTCCGGC

AGAAGAATGAGGTGACCCTCAGCATTCCCGTGGACCACCCAGTCAGAAAG

CTCTTCCAGAAGTTCAAGCAGCAGAAGGAGCTGCGGAATCAGGGCTCAAC

ACAGGGTGACCCTGAGAGGAACCAACTCCAGGTAGAGAGCCGCTCCTTAC

AGAATGGAACCTCCATCACCGGAACCAGCGTGGTGACTGTGTCACAGATT

ACTCCCATTCAGACGTCTCTGGCCTATGTGAAAACCAGTGAATCCCTTAA

GCAGAACAACCGTGATGCCATGGAACTCAAGCCCAACGGCGGTGCTGACC

AAAAATGTCTCAAAGTCAACAGCCCAATAAGAATGAAGAATGGAAATGGA

AAAGGGTGGCTGCGACTCAAGAATAATATGGGAGCCCATGAGGAGAAAAA

GGAAGACTGGAATAATGTCACTAAAGCTGAGTCAATGGGGCTATTGTCTG

AGGACCCCAAGAGCAGTGATTCAGAGAACAGTGTGACCAAAAACCCACTA

AGGAAAACAGATTCTTGTGACAGTGGAATTACAAAAAGTGACCTTCGTTT

GGATAAGGCTGGGGAGGCCCGAAGTCCGCTAGAGCACAGTCCCATCCAGG

CTGATGCCAAGCACCCCTTTTATCCCATCCCCGAGCAGGCCTTACAGACC

ACACTGCAGGAAGTCAAACACGAACTCAAAGAGGACATCCAGCTGCTCAG

CTGCAGAATGACTGCCCTAGAAAAGCAGGTGGCAGAAATTTTAAAAATAC

TGTCGGAAAAAAGCGTACCCCAGGCCTCATCTCCCAAATCCCAAATGCCA

CTCCAAGTACCCCCCCAGATACCATGTCAGGATATTTTTAGTGTCTCAAG

GCCTGAATCACCTGAATCTGACAAAGATGAAATCCACTTTTAATATATAT

ACATATATATTTGTTAATATATTAAAACAGTATATACATATGTGTGTATA

TACAGTATATACATATATATATTTTCACTTGCTTTCAAGATGATGACCAC

ACATGGATTTTGATATGTAAATATTGCATGTCCAGCTGGATTCTGGCCTG

CCAAAGAAGATGATGATTAAAAACATAGATATTGCTTGTATATTATGCAG

TTGACTGCATGCACACTTTACATTTATTTATAATCTCTATTCTATAATAA

AAGAGTATGATTTTTGTTAAAAAAAAAAAAAAAAAAAAAATTCCTCGCCG

GA (SEQ ID NO:4).
```

The human 33408 sequence (FIG. 3; SEQ ID NO:4) is approximately 3553 nucleotides long. The nucleic acid sequence includes an initiation codon (ATG) and a termination codon (TAA), which are underscored above. The region between and inclusive of the initiation codon and the termination codon is a methionine-initiated coding sequence of about 2967 nucleotides, including the termination codon (nucleotides indicated as "coding" of SEQ ID NO:4; SEQ ID NO:6). The coding sequence encodes a 988 amino acid protein (SEQ ID NO:5), which is recited as follows:

```
MPGGKRGLVAPQNTFLENIVRRSSESSFLLGNAQIVDWPVVYSNDGFCK

LSGYHRADVMQKSSTCSFMYGELTDKKTIEKVRQTFDNYESNCFEVLLY

KKNRTPVWFYMQIAPIRNEHEKVVLFLCTFKDITLFKQPIEDDSTKGWT

KFARLTRALTNSRSVLQQLTPMNKTEVVHKHSRLAEVLQLGSDILPQYK

QEAPKTPPHIILLHYCAFKTTWDWVILILTFYTAIMVPYNVSFKTKQNN

IAWLVLDSVVDVIFLVDIVLNFHTTFVGPGGEVISDPKLIRMNYLKTWF

VIDLLSCLPYDIINAFENVDEGISSLFSSLKVVRLLRLGRVARKLDHYL

EYGAAVLVLLVCVFGLVAHWLACIWYSIGDYEVIDEVTNTIQIDSWLYQ

LALSIGTPYRYNTSAGIWEGGPSKDSLYVSSLYFTMTSLTTIGFGNIAP

TTDVEKMFSVAMMMVGSLLYATIFGNVTTIFQQMYANTNRYHEMLNNVR

DFLKLYQVPKGLSERVMDYIVSTWSMSKGIDTEKVLSICPKDMRADICV

HLNRKVFNEHPAFRLASDGCLRALAVEFQTIHCAPGDLIYHAGESVDAL

CFVVSGSLEVIQDDEVVAILGKGDVFGDIFWKETTLAHACANVRALTYC

DLHIIKREALLKVLDFYTAFANSFSRNLTLTCNLRKRIIFRKISDVKKE

EEERLRQKNEVTLSIPVDHPVRKJ1FQKFKQQKELRNQGSTQGDPERNQ

LQVESRSLQNGTSITGTSVVTVSQITPIQTSLAYVKTSESLKQNNRDAM

ELKPNGGADQKCLKVNSPIRMKNGNGKGWLRLKNNMGAHEEKKEDWNNV

TKAESMGLLSEDPKSSDSENSVTKNPLRKTDSCDSGITKSDLRLDKAGE

ARSPLEHSPIQADAKHPFYPIPEQALQTTLQEVKHELKEDIQLLSCRMT

ALEKQVAEILKILSEKSVPQASSPKSQMPLQVPPQIPCQDIFSVSRPES

PESDKDEIHF (SEQ ID NO:5).
```

The human 12189 nucleic acid sequence is recited as follows:

```
TGCTGCGAGCGGCTGGTGCTCAACGTGGCCGGGCTGCGCTTCGAGACGC

GGGCGCGCACGCTGGGCCGCTTCCCGGACACTCTGCTAGGGGACCCAGC

GCGCCGCGGCCGCTTCTACGACGACGCGCGCCGCGAGTATTTCTTCGAC

CGGCACCGGCCCAGCTTCGACGCCGTGCTCTACTACTACCAGTCCGGTG

GGCGGCTGCGGCGGCCGGCGCACGTGCCGCTCGACGTCTTCCTGGAAGA

GGTGGCCTTCTACGGGCTGGGCGCGGCGGCCCTGGCACGCCTGCGCGAG

GACGAGGGCTGCCCGGTGCCGCCCGAGCGCCCCCTGCCCCGCCGCGCCT

TCGCCCGCCAGCTGTGCCTGCTTTTCGAGTTTCCCGAGAGCTCTCAGGC

CGCGCGCGTGCTCGCCGTAGTCTCCGTGCTGGTCATCCTCGTCTCCATC

GTCGTCTTCTGCCTCGAGACGCTGCCTGACTTCCGCGACGACCGCGACG

GCACGGGGCTTGCTGCTGCAGCCGCAGCCGGCCCGTTCCCCGCTCCGCT

GAATGGCTCCAGCCAAATGCCTGGAAATCCACCCCGCCTGCCCTTCAAT

GACCCGTTCTTCGTGGTGGAGACGCTGTGTATTTGTTGGTTCTCCTTTG

AGCTGCTGGTACGCCTCCTGGTCTGTCCAAGCAAGGCTATCTTCTTCAA

GAACGTGATGAACCTCATCGATTTTGTGGCTATCCTTCCCTACTTTGTG
```

-continued
```
GCACTGGGCACCGAGCTGGCCCGGCAGCGAGGGGTGGGCCAGCAGGCCA

TGTCACTGGCCATCCTGAGAGTCATCCGATTGGTGCGTGTCTTCCGCAT

CTTCAAGCTGTCCCGGCACTCAAAGGGCCTGCAAATCTTGGGCCAGACG

CTTCGGGCCTCCATGCGTGAGCTGGGCCTCCTCATCTTTTTCCTCTTCA

TCGGTGTGGTCCTCTTTTCCAGCGCCGTCTACTTTGCCGAAGTTGACCG

GGTGGACTCCCATTTCACTAGCATCCCTGAGTCCTTCTGGTGGGCGGTA

GTCACCATGACTACAGTTGGCTATGGAGACATGGCACCCGTCACTGTGG

GTGGCAAGATAGTGGGCTCTCTGTGTGCCATTGCGGGCGTGCTGACTAT

TTCCCTGCCAGTGCCCGTCATTGTCTCCAATTTCAGCTACTTTTATCAC

CGGGAGACAGAGGGCGAAGAGGCTGGGATGTTCAGCCATGTGGACATGC

AGCCTTGTGGCCCACTGGAGGGCAAGGCCAATGGGGGCTGGTGGACGG

GGAGGTACCTGAGCTACCACCTCCACTCTGGGCACCCCCAGGGAAACAC

CTGGTCACCGAAGTGTGA (SEQ ID NO:7).
```

The human 12189 sequence (FIG. 5; SEQ ID NO:7) is approximately 1341 nucleotides long. The nucleic acid sequence includes a termination codon (TGA), which is underscored above. The coding sequence encodes a 446 amino acid protein (SEQ ID NO:8), which is recited as follows:

```
CCERLVLNVAGLRFETRARTLGRFPDTLLGDPARRGRFYDDARREYFFD

RHRPSFDAVLYYYQSGGRLRRPAHVPLDVFLEEVAFYGLGAAALARLRE

DEGCPVPPERPLPRRAFARQLCLLFEFPESSQAARVLAVVSVLVILVSI

VVFCLETLPDFRDDRDGTGLAAAAAAGPFPAPLNGSSQMPGNPPRLPFN

DPFFVVETLCICWFSFELLVRLLVCPSKAIFFKNVMNLIDFVAILPYFV

ALGTELARQRGVGQQAMSLAILRVIRLVRVFRIFKLSRHSKGLQILGQT

LRASMRELGLLIFFLFIGVVLFSSAVYFAEVDRVDSHFTSIPESFWWAV

VTMTTVGYGDMAPVTVGGKIVGSLCAIAGVLTISLPVPVIVSNFSYFYH

RETEGEEAGMFSHVDMQPCGPLEGKANGGLVDGEVPELPPPLWAPPGKH

LVTEV (SEQ ID NO:8).
```

Example 2

Tissue Distribution of 52906 and 33408 mRNA by TaqMan Analysis

Endogenous human 52906 and 33408 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 52906 and 33408 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 3 and 4. 52906 mRNA was detected in brain, prostate tumor, and heart samples (Table 3). 33408 expression was found in brain, heart, skin, and adipose samples (Table 4).

TABLE 3

Expression of 52906 mRNA in Human Tissues and Cell Lines

| Tissue | Relative Expression |
| --- | --- |
| Artery/normal | 0 |
| Aorta/diseased | 0 |
| Vein/normal | 0 |
| Coronary smooth muscle cells | 0 |
| Human umbilical vein endothelial cells | 0 |
| Hemangioma | 0 |
| Heart/normal | 0 |
| Heart/congestive heart failure | 0.1902 |
| Kidney | 0 |
| Skeletal muscle | 0 |
| Adipose/normal | 0 |
| Pancreas | 0 |
| Primary osteoblasts | 0 |
| Osteoclasts (differentiated) | 0 |
| Skin/normal | 0 |
| Spinal cord/normal | 0 |
| Brain Cortex/normal | 1.6367 |
| Brain Hypothalamus/normal | 0 |
| Nerve | 0 |
| Dorsal Root Ganglion | 0 |
| Breast/normal | 0 |
| Breast/tumor | 0 |
| Ovary/normal | 0 |
| Ovary/tumor | 0 |
| Prostate/normal | 0 |
| Prostate/tumor | 1.1613 |
| Salivary glands | 0 |
| Colon/normal | 0 |
| Colon/tumor | 0 |
| Lung/normal | 0 |
| Lung/tumor | 0 |
| Lung/chronic obstructive pulmonary disease | 0 |
| Colon/inflammatory bowel disease | 0 |
| Liver/normal | 0 |
| Liver fibrosis | 0 |
| Spleen/normal | 0 |
| Tonsil/normal | 0 |
| Lymph node/normal | 0 |
| Small intestine/normal | 0 |
| Macrophages | 0 |
| Synovium | 0 |
| Bone marrow/mononuclear cells | 0 |
| Activated peripheral blood mononuclear cells | 0 |
| Neutrophils | 0 |
| Megakaryocytes | 0 |
| Erythroid cells | 0 |
| positive control | 0 |

TABLE 4

Expression of 33408 mRNA in Human Tissues and Cell Lines

| Tissue | Relative Expression |
| --- | --- |
| Prostate | 0.00 |
| Osteoclasts | 0.00 |
| Liver | 0.00 |
| Breast | 0.00 |
| Breast | 0.00 |
| Skeletal Muscle | 2.60 |
| Skeletal Muscle | 0.13 |
| Brain | 33.03 |
| Colon | 0.06 |
| Colon | 0.01 |
| Heart | 30.71 |
| Heart | 0.00 |
| Ovary | 0.00 |
| Ovary | 0.00 |
| Kidney | 0.00 |
| Kidney | 0.01 |
| Lung | 0.01 |
| Lung | 0.00 |
| Vein | 0.10 |
| Vein | 0.01 |
| Adipose | 0.00 |
| Adipose | 4.26 |
| Small Intestine | 0.00 |
| Thyroid | 0.00 |
| Bone Marrow | 0.00 |
| Skin | 11.72 |
| Testes | 0.37 |
| Placenta | 0.01 |
| Fetal Liver | 0.00 |
| Fetal Liver | 0.00 |
| Fetal Heart | 0.00 |
| Fetal Heart | 0.00 |
| Osteoblasts/undifferentiated | 0.00 |
| Osteoblasts/differentiated | 0.00 |
| Osteoblasts/primary culture | 0.00 |
| Spinal Cord | 0.00 |
| Cervix | 0.00 |
| Spleen | 0.00 |
| Spinal Cord | 0.00 |
| Thymus | 0.00 |
| Tonsil | 0.00 |
| Lymph Node | 0.00 |
| Aorta | 0.00 |

Example 3

Tissue Distribution of 52906, 33408, or 12189 mRNA by Northern Analysis

Northern blot hybridizations with various RNA samples can be performed under standard conditions and washed under stringent conditions, i.e., 0.2×SSC at 65° C. A DNA probe corresponding to all or a portion of the 52906, 33408, or 12189 cDNA (SEQ ID NO:1, SEQ ID NO:4, or SEQ ID NO:7) can be used. The DNA is radioactively labeled with $^{32}$P-dCTP using the Prime-It Kit (Stratagene, La Jolla, Calif.) according to the instructions of the supplier. Filters containing, for example, mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4

Recombinant Expression of 52906 33408, or 12189 in Bacterial Cells

In this example, 52906, 33408, or 12189 is expressed as a recombinant glutathione-S-transferase (GST) fusion polypeptide in E. coli and the fusion polypeptide is isolated and characterized. Specifically, 52906,33408, or 12189 is fused to GST and this fusion polypeptide is expressed in E. coli, e.g., strain PEB199. Expression of the GST-52906, 33408, or 12189 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 52906, 33408, or 12189 Protein in COS Cells

To express the 52906, 33408, or 12189 gene in COS cells (e.g., COS-7 cells, CV-1 origin SV40 cells; Gluzman (1981) CellI23:175–182), the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 52906, 33408, or 12189 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 52906, 33408, or 12189 DNA sequence is amplified by PCR using two primers. The 5' primer contains the restriction site of interest followed by approximately twenty nucleotides of the 52906, 33408, or 12189 coding sequence starting from the initiation codon; the 3' end sequence contains complementary sequences to the other restriction site of interest, a translation stop codon, the HA tag or FLAG tag and the last 20 nucleotides of the 52906, 33408, or 12189 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 52906, 33408, or 12189 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 52906, 33408, or 12189-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) Molecular Cloning: A Laboratory Manual. 2nd, ed., Cold Spring Harbor Laboratory, Cold Spring Harbor Laboratory Press, Cold Spring Harbor, N.Y. The expression of the 52906, 33408, or 12189 polypeptide is detected by radiolabelling ($^{35}$S-methionine or $^{35}$S-cysteine available from NEN, Boston, Mass., can be used) and immunoprecipitation (Harlow, E. and Lane, D. (1988) Antibodies: A Laboratory Manual, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 52906, 33408, or 12189 coding sequence is cloned directly into the polylinker of the pcDNA/Amp vector using the appropriate restriction sites. The resulting plasmid is transfected into COS cells in the manner described above, and the expression of the 52906, 33408, or 12189 polypeptide is detected by radiolabelling and immunoprecipitation using a 52906, 33408, or 12189 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising a nucleotide sequence which is at least 95% identical to the entire length of the nucleotide sequence of SEQ ID NO:1, or a full complement thereof;
   b) a nucleic acid molecule comprising a nucleotide sequence which is at least 95%, identical to the entire length of the nucleotide sequence of SEQ ID NO:3, or a full complement thereof; and
   c) a nucleic acid molecule which encodes a polypeptide comprising an amino acid sequence at least 95% identical to the entire length of the amino acid sequence of SEQ ID NO:2;
   wherein the nucleic acid molecule encodes a polypeptide having potassium channel activity.

2. An isolated nucleic acid molecule selected from the group consisting of:
   a) a nucleic acid molecule comprising the nucleic acid sequence of SEQ ID NO:1 or SEQ ID NO:3, or a full complement thereof; and
   b) a nucleic acid molecule which encodes a polypeptide comprising the amino acid sequence of SEQ ID NO:2, or a full complement thereof.

3. An isolated nucleic acid molecule selected from the group consisting of:
   a) a nucleic acid molecule consisting of the nucleic acid sequence of SEQ ID NO:1 or SEQ ID NO:3, or a full complement thereof; and
   b) a nucleic acid molecule which encodes a polypeptide consisting of the amino acid sequence of SEQ ID NO:2, or a full complement thereof.

4. The nucleic acid molecule of claim 1, further comprising vector nucleic acid sequences.

5. The nucleic acid molecule of claim 2, further comprising vector nucleic acid sequences.

6. The nucleic acid molecule of claim 3, further comprising vector nucleic acid sequences.

7. The nucleic acid molecule of claim 1, further comprising nucleic acid sequences encoding a heterologous polypeptide.

8. The nucleic acid molecule of claim 2, further comprising nucleic acid sequences encoding a heterologous polypeptide.

9. The nucleic acid molecule of claim 3, further comprising nucleic acid sequences encoding a heterologous polypeptide.

10. The nucleic acid molecule of claim 7, further comprising vector nucleic acid sequences.

11. The nucleic acid molecule of claim 8, further comprising vector nucleic acid sequences.

12. The nucleic acid molecule of claim 9, further comprising vector nucleic acid sequences.

13. An isolated host cell which contains the nucleic acid molecule of claim 4.

14. The host cell of claim 13 which is a mammalian host cell.

15. An isolated host cell which contains the nucleic acid molecule of claim 5.

16. The host cell of claim 15 which is a mammalian host cell.

17. An isolated host cell which contains the nucleic acid molecule of claim 6.

18. The host cell of claim 17 which is a mammalian host cell.

19. An isolated host cell which contains the nucleic acid molecule of claim 10.

20. The host cell of claim 19 which is a mammalian host cell.

21. An isolated host cell which contains the nucleic acid molecule of claim 11.

22. The host cell of claim 21 which is a mammalian host cell.

23. An isolated host cell which contains the nucleic acid molecule of claim 12.

24. The host cell of claim 23 which is a mammalian host cell.

25. A method for producing a polypeptide, comprising culturing the host cell of claim 13 under conditions in which the polypeptide encoded by the nucleic acid molecule is expressed, thereby producing a polypeptide.

26. A method for producing a polypeptide, comprising culturing the host cell of claim 15 under conditions in which the polypeptide encoded by the nucleic acid molecule is expressed, thereby producing a polypeptide.

27. A method for producing a polypeptide, comprising culturing the host cell of claim 17 under conditions n which the polypeptide encoded by the nucleic acid molecule is expressed, thereby producing a polypeptide.

28. A method for producing a polypeptide, comprising culturing the host cell of claim 19 under conditions in which the polypeptide encoded by the nucleic acid molecule is expressed, thereby producing polypeptide.

29. A method for producing a polypeptide, comprising culturing the host cell of claim 21 under conditions in which the polypeptide encoded by the nucleic acid molecule is expressed, thereby producing a polypeptide.

30. A method for producing a polypeptide, comprising culturing the host cell of claim 22 under conditions in which the polypeptide encoded by the nucleic acid molecule is expressed, thereby producing a polypeptide.

* * * * *